(12) United States Patent
Derive et al.

(10) Patent No.: US 12,364,733 B1
(45) Date of Patent: Jul. 22, 2025

(54) METHOD FOR TREATING SEPTIC SHOCK

(71) Applicant: Inotrem, Vandoeuvre-les-Nancy (FR)

(72) Inventors: Marc Derive, Villers-les-Nancy (FR); Aurelie Olivier, Clairefontaine-en-Yvelines (FR); Kevin Carrasco, Dombasle-sur-Meurthe (FR); Martin Koch, Montauban (FR); Margarita Salcedo-Magguilli, Châtillon (FR); Amir Boufenzer, Villers-lés-Nancy (FR); Lucie Jolly, Bar-le-Duc (FR); Jean-Jacques Garaud, Paris (FR)

(73) Assignee: Inotrem, Vandoeuvre-les-Nancy (FR)

( * ) Notice: Subject to any disclaimer, the term of this patent is extended or adjusted under 35 U.S.C. 154(b) by 0 days.

(21) Appl. No.: 18/766,845

(22) Filed: Jul. 9, 2024

Related U.S. Application Data

(63) Continuation of application No. 17/280,358, filed as application No. PCT/EP2019/076263 on Sep. 27, 2019, now abandoned.

(30) Foreign Application Priority Data

Sep. 28, 2018 (EP) .................................... 18306277

(51) Int. Cl.
*A61K 38/10* (2006.01)
*A61P 9/02* (2006.01)

(52) U.S. Cl.
CPC ................ *A61K 38/10* (2013.01); *A61P 9/02* (2018.01)

(58) Field of Classification Search
None
See application file for complete search history.

(56) References Cited

U.S. PATENT DOCUMENTS

| | | | |
|---|---|---|---|
| 8,106,165 B2 | 1/2012 | Ruben et al. | |
| 8,114,603 B2 | 2/2012 | Margolin et al. | |
| 9,255,136 B2* | 2/2016 | Gibot | A61P 29/00 |
| 9,815,883 B2* | 11/2017 | Gibot | A61P 29/00 |
| 10,948,498 B2 | 3/2021 | Derive et al. | |
| 2004/0121343 A1* | 6/2004 | Buechler | C12Q 1/6883 |
| | | | 435/6.14 |
| 2013/0150559 A1 | 6/2013 | Colonna et al. | |
| 2013/0211050 A1 | 8/2013 | Stennicke et al. | |
| 2013/0309239 A1 | 11/2013 | Stennicke et al. | |

FOREIGN PATENT DOCUMENTS

| | | | | |
|---|---|---|---|---|
| WO | WO-2005/071408 A1 | 8/2005 | | |
| WO | WO-2009/141359 A1 | 11/2009 | | |
| WO | WO-2011124685 A1 * | 10/2011 | ............ | A61K 38/08 |
| WO | WO-2015/018936 A1 | 2/2015 | | |

OTHER PUBLICATIONS

Francois et al (Intensive Care Med. Jul. 2020;46(7):1425-1437. Epub May 28, 2020) (Year: 2020).*
Siskind et al (Front Immunol. Jun. 15, 2022;13:907387) (Year: 2022).*
Bolton et al (Malar J. Apr. 17, 2020;19(1):159) (Year: 2020).*
Gibot et al. (Annals of Internal Medicine 2004;141(1):9-15) (Year: 2004).*
Rios-Toro et al. (PLoS One. Apr. 5, 2017;12(4):e0175254) (Year: 2017).*
Horonenko et al. (Chest. Jul. 2007;132(1):58-63. Epub May 15, 2007) (Year: 2007).*
Prieto et al. (Clin Chem Lab Med 2010;48(6):835-838) (Year: 2010).*
Akamatsu et al. (2005) "Prevention of Renal Impairment by Continuous Infusion of Human Atrial Natriuretic Peptide after Liver Transplantation", Transplantation, 80, pp. 1093-1098.
Arizaga-Ballesteros et al. (2015) "Can sTREM-1 predict septic shock & death in late-onset neonatal sepsis? A pilot study", International Journal of Infectious Diseases, 30, pp. 27-32.
Baruah et al. (2015) "Identification of a Novel Splice Variant Isoform of TREM-1 in Human Neutrophil Granules", Journal of Immunology, 195, pp. 5725-5731.
Bellos et al. (2018) "Soluble TREM-1 as a predictive factor of neonatal sepsis: a metaanalysis", Inflammation Research, 67, pp. 571-578.
Bone et al. (1992) "Definitions for sepsis and organ failure and guidelines for the use of innovative therapies in sepsis. The ACCP/SCCM Consensus Conference Committee. American College of Chest Physicians/Society of Critical Care Medicine", Chest, 101(6), pp. 1644-1655.
Brenner et al. (2017) "Soluble TREM-1 as a diagnostic and prognostic biomarker in patients with septic shock—an observational clinical study", Biomarkers, 22(1):63-69, pp. 1-24.
Cao et al. (2017) "Soluble triggering receptor expressed on myeloid cell-1 (sTREM 1): a potential biomarker for the diagnosis of infectious diseases", Front Med, 11(2), pp. 169-177.
Carrasco et al. (2019) "TREM-1 multimerization is essential for its activation on monocytes and neutrophils", Cellular & Molecular Immunology, 16(5), pp. 460-472.
Charles et al. (2016) "Significance of soluble triggering receptor expressed on myeloid cells-1 elevation in patients admitted to the intensive care unit with sepsis", BMC Infectious Diseases, 16(1) 559, pp. 1-12.

(Continued)

*Primary Examiner* — Brian Gangle
*Assistant Examiner* — Andrea K McCollum
(74) *Attorney, Agent, or Firm* — Goodwin Procter LLP

(57) ABSTRACT

The present disclosure relates to a method of treating an acute inflammatory disorder such as septic shock in a subject in need thereof. The method involves administering to a subject who has a soluble TREM-1 (sTREM-1) level measured in a biological sample from the subject greater than a predetermined sTREM-1 value an amount of a TREM-1 inhibitor sufficient to treat the inflammatory disorder.

16 Claims, 15 Drawing Sheets

Specification includes a Sequence Listing.

(56) References Cited

OTHER PUBLICATIONS

Conrad et al. (2015) "Early prediction of norepinephrine dependency and refractory septic shock with a multi modal approach of vascular failure", Journal of Critical Care, 30, pp. 739-743.

Cuvier et al. (2018) "A first-in-man safety and pharmacokinetics study of nangibotide, a new modulator of innate immune response through TREM-1 receptor inhibition", British Journal of Clinical Pharmacology, 84(10), pp. 2270-2279.

De Vos et al. (1992) "Human Growth Hormone and Extracellular Domain of its Receptor: Crystal Structure of the Complex", Science, 255, 5042, pp. 306-312.

Ford et al. (2009) "TREM and TREM-like Receptors in Inflammation and Disease", Curr Opin Immunol, 21 (1), pp. 1-17.

Gamez-Nava et al. (2017) "Utility of soluble triggering receptor expressed on myeloid cells-1 (sTREM-1) as biomarker to predict therapeutic response to methotrexate in rheumatoid arthritis", Innate Immunity, 23(7), pp. 606-614.

Gattis et al. (2006) "The Structure of the Extracellular Domain of Triggering Receptor Expressed on Myeloid Cells Like Transcript-1 and Evidence for a Naturally Occurring Soluble Fragment", The Journal of Biological Chemistry, 281, 19, pp. 13396-13403.

Gibot et al. (2004) "A Soluble Form of the Triggering Receptor Expressed on Myeloid Cells-1 Modulates the Inflammatory Response in Murine Sepsis", Journal of Experimental Medicine, 200(11 ), pp. 1419-1426.

Gibot et al. (2012) "Combination Biomarkers to Diagnose Sepsis in the Critically III Patient", American Journal of Respiratory and Critical Care Medicine, 186(1), pp. 65-71.

Gibot et al. (2004) "Plasma Level of a Triggering Receptor Expressed on Myeloid Cells-1: Its Diagnostic Accuracy in Patients with Suspected Sepsis", Ann Intern Med, 141 (1), pp. 9-15.

Gibot et al. (2005) "Time-course of sTREM (soluble triggering receptor expressed on myeloid cells)-1, procalcitonin, and reactive protein plasma concentrations during sepsis", Crit Care Med, vol. 33, No. 4, pp. 792-796.

Gomez-Pina et al. (2007) "Metalloproteinases Shed TREM-1 Ectodomain from Lipopolysaccharide-Stimulated Human Monocytes", Journal of Immunology, 179(6), pp. 4065-4073.

Grover et al. (2014) "A Biomarker Panel (Bioscore) Incorporating Monocytic Surface and Soluble TREM-1 Has High Discriminative Value for Ventilator-Associated Pneumonia: A Prospective Observational Study", PLOS ONE, 9(10):e109686, pp. 1-8.

Horonenko et al. (2007) "Soluble triggering receptor expressed on myeloid cell-1 is increased in patients with ventilator-associated pneumonia: a preliminary report", Chest, 132, pp. 158-156.

Jeong et al. (2012) "Measurement of Plasma sTREM-1 in patients with severe sepsis receiving early goal-directed therapy and evaluation of its usefulness", Shock, 37, 6 pp. 574-578.

Jolly et al. (2017) "Triggering Receptor Expressed on Myeloid cells-1: a new player in platelet aggregation", Cellular Haemostasis and Platelets, Thrombosis Haemostasis, 117(9), pp. 1772-1781.

Koenig et al. (2017) "Mutational landscape of antibody variable domains reveals a switch modulating the interdomain conformational dynamics and antigen binding", PNAS, 114, 4, E486-E495.

Kunik et al. (2012) "Structural Consensus among Antibodies Defines the Antigen Binding Site", PLoS Computational Biology, 8, 2, pp. 1-12.

Marioli et al. (2014) "Early changes of the kinetics of monocyte trem-1 reflect final outcome in human sepsis", BMC Immunology, 15(585), pp. 1-8.

O'Connor (2017) "Roche Sees "New Front in Critical Care Medicine" With CDx Deal Aimed at Septic Shock", 360DX, https://www_360dx_com/business-news/roche-sees-new-front-critical-care-medicine-cdx-deal-aimed-septic-shock#Yj2KX-fMKUk, Dec. 7, 2017, 14 pages.

Ravetti et al. (2015) "sTREM-1 predicts intensive care unit and 28-day mortality in cancer patients with severe sepsis and septic shock", Journal of Critical Care, 30(2), p. 440.e7-440.e13.

Rein (2017) "Inotrem and Roche Diagnostics sign a R&D collaboration agreement in the field of septic shock to develop a companion diagnostic test", Nov. 10, 2017, https://www_inotrem_com/2017/11/10/ inotrem-roche-diagnostics-sign-rd-collaboration-agreement-field-septic-shock-develop-companion-diagnostic-test/, 2 pages.

Rios-Toro et al. (2017) "Soluble membrane receptors, interleukin 6, procalcitonin and C reactive protein as prognostic markers in patients with severe sepsis and septic shock", PLOS ONE, 12(4):e0175254, pp. 1-18.

Seymour et al. (2016) "Assessment of Clinical Criteria for Sepsis: For the Third International Consensus Definitions for Sepsis and Septic Shock (Sepsis-3)", JAMA, 315(8), pp. 1-27.

Shankar et al. (2008) "Recommendations for the validation of immunoassays used for detection of host antibodies against biotechnology products", Journal of Pharmaceutical and Biomedical Analysis, 48(5), pp. 1267-1281.

Shankar-Hari et al. (2016) "Developing a New Definition and Assessing New Clinical Criteria for Septic Shock: For the Third International Consensus Definitions for Sepsis and Septic Shock (Sepsis-3)", JAMA, 315(8), pp. 1-28.

Singer et al. (2016) "The Third International Consensus Definitions for Sepsis and Septic Shock (Sepsis-3)", JAMA, 315(8), pp. 1-23.

Su et al. (2013) "Diagnostic Value of Dynamics Serum sCD163, sTREM-1, PCT, and CRP in Differentiating Sepsis, Severity Assessment, and Prognostic Prediction", Mediators of Inflammation, vol. 2013:969875, pp. 1-9.

Su et al. (2016) "Role of sTREM-1 in predicting mortality of infection: a systematic review and meta-analysis", BMJ Open, 6(5):e010314, pp. 1-9.

Su et al. (2012) "Value of soluble TREM-1, procalcitonin, and C-reactive protein serum levels as biomarkers for detecting bacteremia among sepsis patients with new fever in intensive care units: a prospective cohort study", BMC Infectious Diseases, 12(157), pp. 1-10.

Winkler et al. (2000) "Changing the Antigen Binding Specificity by Single Point Mutations of an Anti-p24 (H IV-1) Antibody", The Journal of Immunology, 165, pp. 4505-4514.

Wu et al. (2012) "Accuracy of plasma sTREM-1 for sepsis diagnosis in systemic inflammatory patients: a systematic review and meta-analysis", Critical Care, 16(6):R229, pp. 1-11.

Zhang et al. (2011) "Dynamic changes of serum soluble triggering receptor expressed on myeloid cells-1 (sTREM-1) reflect I S.J.Ko/23 sepsis severity and can predict prognosis: a prospective study", BMC Infectious Disease, 11 :53, pp. 1-7.

International Search Report for International Patent Application No. PCT/EP2019/076263, mailed Nov. 28, 2019 (6 pages).

Written Opinion for International Patent Application No. PCT/EP2019/076263, mailed Nov. 28, 2019 (5 pages).

"Nangibotide," Proposed INN (International Nonproprietary Name): List 117, WHO Drug Information, vol. 31, No. 2, pp. 306-307, Jul. 7, 2017.

"Nangibotide," Recommended INN (International Nonproprietary Name): List 79, WHO Drug Information, vol. 32, No. 1, pp. 142-143, Mar. 9, 2018.

ClinicalTrials.gov ID NCT02393781 "Adrenodedulin and Outcome in Severe Sepsis and Septic Shock (AdrenOSS)," Sponsor: Sphingotec GmbH, Study Details, Jun. 6, 2016 (9 pages).

ClinicalTrials.gov ID NCT03158948 "Safety, Tolerability, Pharmacokinetics and Pharmacodynamics of 2 Doses of MOTREM (nangibotide) in Patients with Septic Shock," Sponsor: Inotrem, Record History, Version 8, Jul. 20, 2018 (11 pages).

Cohen et al. (2015) "Sepsis: a roadmap for future research," Lancet Infect Dis., 15(5):581-614.

Dong (2015) "Role of soluble triggering receptor on myeloid cells-1 in the diagnosis of infectious diseases," Chin. J. Health Care Med., 17(1): 72-73 (7 total pages including 5 pages of English machine translation).

Fleischmann et al. (2016) "Hospital Incidence and Mortality Rates of Sepsis," Dtsch Arztebl Int., 113(10):159-66.

Han et al. (2016) "Amelioration of sepsis by TIE2 activation-induced vascular protection," Sci Transl Med., 8(335):335ra55.

Knaus et al. (1985) "Apache II: a severity of disease classification system," Crit Care Med., 13(10):818-29.

(56) References Cited

OTHER PUBLICATIONS

Knaus et al. (1991) "The Apache III prognostic system. Risk prediction of hospital mortality for critically ill hospitalized adults," Chest., 100(6):1619-36.

Le Gall et al. (1984) "A simplified acute physiology score for ICU patients," Crit Care Med., 12(11):975-7.

Le Gall et al. (1993) "A new Simplified Acute Physiology Score (SAPS II) based on a European/North American multicenter study," JAMA., 22-29;270(24):2957-63.

Metnitz et al. (2005) "SAPS 3 Investigators. SAPS 3—From evaluation of the patient to evaluation of the intensive care unit. Part 1: Objectives, methods and cohort description," Intensive Care Med., 31(10):1336-44.

Moreno et al. (2005) "SAPS 3 Investigators. SAPS 3—From evaluation of the patient to evaluation of the intensive care unit. Part 2: Development of a prognostic model for hospital mortality at ICU admission," Intensive Care Med., 31(10):1345-55.

Thurston and Daly (2012) "The complex role of angiopoietin-2 in the angiopoietin-tie signaling pathway," Cold Spring Harb Perspect Med., 2(9):a006550.

Vincent et al. (1998) "Use of the SOFA score to assess the incidence of organ dysfunction/failure in intensive care units: results of a multicenter, prospective study," Working group on "sepsis-related problems" of the European Society of Intensive Care Medicine. Crit Care Med., 26(11):1793-800. Significance.

Wu (2015) "The detection and Signifiance of serum soluble triggering receptor expressed on myeloid cell 1, tumor necrosis factor-α and interleukin-6 in patients with chronic obstructive pulmonary disease," Master's Degree Thesis of Southern Medical University (123 total pages with English machine translation, 65 pages).

Zimmerman JE, Kramer AA, McNair DS, Malila FM 2006) "Acute Physiology and Chronic Health Evaluation (APACHE) IV: hospital mortality assessment for today's critically ill patients," Crit Care Med., 34(5):1297-310.

\* cited by examiner

Study Flow chart of sequential dose Levels tested in Stage 1
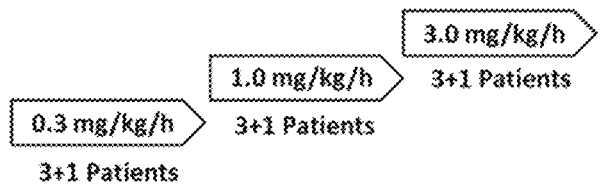
Study Flow chart Stage 1 (per cohort)
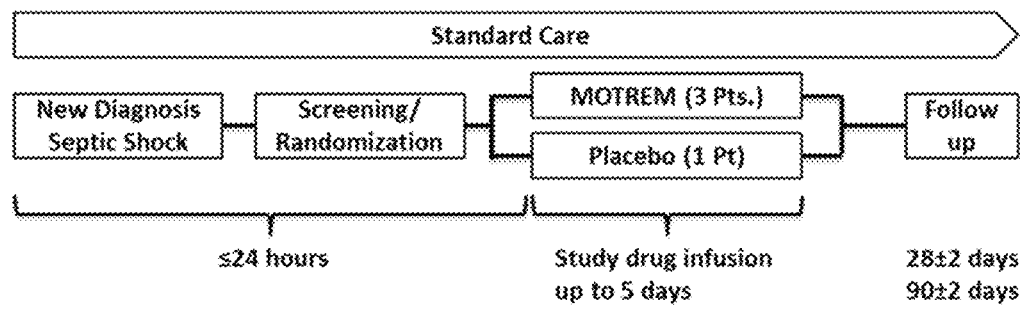
Study Flow chart Stage 2
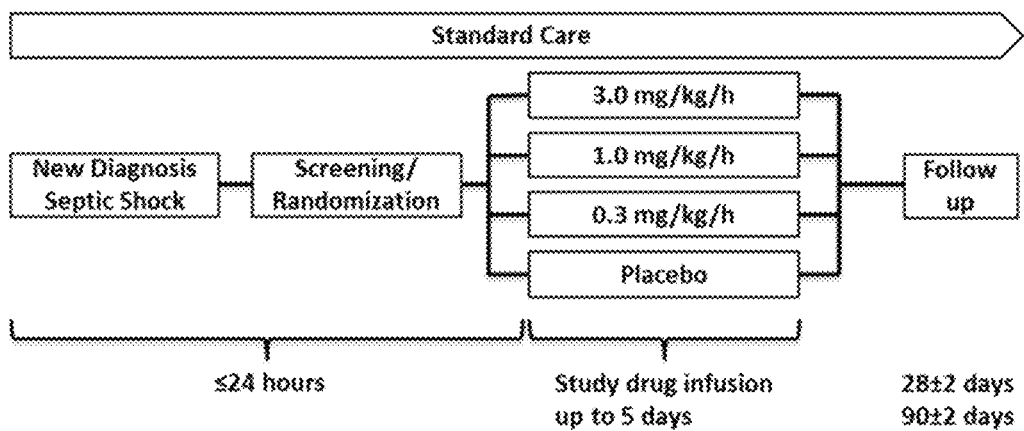
FIG. 7

```
┌─────────────────────────────────────────────────────────────┐
│                  Randomised Patients (N=50)                  │
├──────────┬──────────────┬──────────────┬──────────────────┤
│ Placebo  │ Nangibotide  │ Nangibotide  │ Nangibotide      │
│ N=12     │ 0.3mg/kg/h   │ 1.0mg/kg/h   │ 3.0mg/kg/h       │
│          │ N=13         │ N=13         │ N=12             │
└──────────┴──────────────┴──────────────┴──────────────────┘
                              │
                              ├─────→ Patient not received IMP: (N=1);
                              │        Nangibotide 1.0mg/kg/h: 04000
                              │
┌─────────────────────────────────────────────────────────────┐
│                   Treated Patients (N=49)                    │
├──────────┬──────────────┬──────────────┬──────────────────┤
│ Placebo  │ Nangibotide  │ Nangibotide  │ Nangibotide      │
│ N=12     │ 0.3mg/kg/h   │ 1.0mg/kg/h   │ 3.0mg/kg/h       │
│          │ N=13         │ N=12         │ N=12             │
└──────────┴──────────────┴──────────────┴──────────────────┘
                              │
                              ├─────→ Dead Patients (N=8):
                              │        Nangibotide 0.3mg/kg/h: 10041
                              │        Nangibotide 1.0mg/kg/h: 01008
                              │        Nangibotide 3.0mg/kg/h: 01009;
                              │         02003; 10025
                              │        Placebo: 01007; 10030; 31001
                              │
┌─────────────────────────────────────────────────────────────┐
│            Patients completed the study to D28 (N=41)       │
├──────────┬──────────────┬──────────────┬──────────────────┤
│ Placebo  │ Nangibotide  │ Nangibotide  │ Nangibotide      │
│ N=9      │ 0.3mg/kg/h   │ 1.0mg/kg/h   │ 3.0 mg/kg/h      │
│          │ N=12         │ N=11         │ N=9              │
└──────────┴──────────────┴──────────────┴──────────────────┘
                              │
                              ├─────→ Dead Patients (N=8):
                              │        Nangibotide 0.3mg/kg/h: 10005;
                              │         10027; 11027
                              │        Nangibotide 1.0mg/kg/h: 11041
                              │        Nangibotide 3.0mg/kg/h: 10040
                              │
┌─────────────────────────────────────────────────────────────┐
│            Patients completed the study to D90 (N=36)       │
├──────────┬──────────────┬──────────────┬──────────────────┤
│ Placebo  │ Nangibotide  │ Nangibotide  │ Nangibotide      │
│ N=9      │ 0.3mg/kg/h   │ 1.0mg/kg/h   │ 3.0 mg/kg/h      │
│          │ N=9          │ N=10         │ N=8              │
└──────────┴──────────────┴──────────────┴──────────────────┘
```

FIG. 8

SEQUENCE LISTING

```
Sequence total quantity: 19
SEQ ID NO: 1             moltype = AA  length = 234
FEATURE                  Location/Qualifiers
source                   1..234
                         mol_type = protein
                         organism = Homo sapiens
SEQUENCE: 1
MRKTRLWGLL WMLFVSELRA ATKLTEEKYE LKEGQTLDVK CDYTLEKFAS SQKAWQIIRD   60
GEMPKTLACT ERPSKNSHPV QVGRIILEDY HDHGLLRVRM VNLQVEDSGL YQCVIYQPPK  120
EPHMLFDRIR LVVTKGFSGT PGSNENSTQN VYKIPPTTTK ALCPLYTSPR TVTQAPPKST  180
ADVSTPDSEI NLTNVTDIIR VPVFNIVILL AGGFLSKSLV FSVLFAVTLR SFVP        234

SEQ ID NO: 2             moltype = AA  length = 150
FEATURE                  Location/Qualifiers
source                   1..150
                         mol_type = protein
                         organism = Homo sapiens
SEQUENCE: 2
MRKTRLWGLL WMLFVSELRA ATKLTEEKYE LKEGQTLDVK CDYTLEKFAS SQKAWQIIRD   60
GEMPKTLACT ERPSKNSHPV QVGRIILEDY HDHGLLRVRM VNLQVEDSGL YQCVIYQPPK  120
EPHMLFDRIR LVVTKGFRCS TLSFSWLVDS                                   150

SEQ ID NO: 3             moltype = AA  length = 225
FEATURE                  Location/Qualifiers
source                   1..225
                         mol_type = protein
                         organism = Homo sapiens
SEQUENCE: 3
MRKTRLWGLL WMLFVSELRA ATKLTEEKYE LKEGQTLDVK CDYTLEKFAS SQKAWQIIRD   60
GEMPKTLACT ERPSKNSHPV QVGRIILEDY HDHGLLRVRM VNLQVEDSGL YQCVIYQPPK  120
EPHMLFDRIR LVVTKGFSGT PGSNENSTQN VYKIPPTTTK ALCPLYTSPR TVTQAPPKST  180
ADVSTPDSEI NLTNVTDIIR YSFQVPGPLV WTLSPLFPSL CAERM                  225

SEQ ID NO: 4             moltype = AA  length = 250
FEATURE                  Location/Qualifiers
source                   1..250
                         mol_type = protein
                         organism = Homo sapiens
SEQUENCE: 4
MRKTRLWGLL WMLFVSELRA ATKLTEEKYE LKEGQTLDVK CDYTLEKFAS SQKAWQIIRD   60
GEMPKTLACT ERPSKNSHPV QVGRIILEDY HDHGLLRVRM VNLQVEDSGL YQCVIYQPPK  120
EPHMLFDRIR LVVTKGFSGT PGSNENSTQN VYKIPPTTTK ALCPLYTSPR TVTQAPPKST  180
ADVSTPDSEI NLTNVTDIIR EKSMTFGIRR LDVESHPLPP LHTGHFRISQ FFSQAGTQSL  240
HSCYKGKPTP                                                         250

SEQ ID NO: 5             moltype = AA  length = 185
FEATURE                  Location/Qualifiers
source                   1..185
                         mol_type = protein
                         organism = Homo sapiens
SEQUENCE: 5
ATKLTEEKYE LKEGQTLDVK CDYTLEKFAS SQKAWQIIRD GEMPKTLACT ERPSKNSHPV   60
QVGRIILEDY HDHGLLRVRM VNLQVEDSGL YQCVIYQPPK EPHMLFDRIR LVVTKGFSGT  120
PGSNENSTQN VYKIPPTTTK ALCPLYTSPR TVTQAPPKST ADVSTPDSEI NLTNVTDIIR  180
VPVFN                                                              185
```

```
SEQ ID NO: 6              moltype = AA  length = 175
FEATURE                   Location/Qualifiers
source                    1..175
                          mol_type = protein
                          organism = Homo sapiens
SEQUENCE: 6
LKEGQTLDVK CDYTLEKFAS SQKAWQIIRD GEMPKTLACT ERPSKNSHPV QVGRIILEDY    60
HDHGLLRVRM VNLQVEDSGL YQCVIYQPPK EPHMLFDRIR LVVTKGFSGT PGSNENSTQN   120
VYKIPPTTTK ALCPLYTSPR TVTQAPPKST ADVSTPDSEI NLTNVTDIIR VPVFN        175

SEQ ID NO: 7              moltype = AA  length = 311
FEATURE                   Location/Qualifiers
source                    1..311
                          mol_type = protein
                          organism = Homo sapiens
SEQUENCE: 7
MGLTLLLLLL LGLEGQGIVG SLPEVLQAPV GSSILVQCHY RLQDVKAQKV WCRFLPEGCQ    60
PLVSSAVDRR APAGRRTFLT DLGGGLLQVE MVTLQEEDAG EYGCMVDGAR GPQILHRVSL   120
NILPPEEEEE THKIGSLAEN AFSDPAGSAN PLEPSQDEKS IPLIWGAVLL VGLLVAAVVL   180
FAVMAKRKQG NRLGVCGRFL SSRVSGMNPS SVVHHVSDSG PAAELPLDVP HIRLDSPPSF   240
DNTTYTSLPL DSPSGKPSLP APSSLPPLPP KVLVCSKPVT YATVIFPGGN KGGGTSCGPA   300
QNPPNNQTPS S                                                       311

SEQ ID NO: 8              moltype = AA  length = 17
FEATURE                   Location/Qualifiers
REGION                    1..17
                          note = TLT-1 peptide
source                    1..17
                          mol_type = protein
                          organism = synthetic construct
SEQUENCE: 8
LQEEDAGEYG CMVDGAR                                                   17

SEQ ID NO: 9              moltype = AA  length = 12
FEATURE                   Location/Qualifiers
REGION                    1..12
                          note = TLT-1 peptide
source                    1..12
                          mol_type = protein
                          organism = synthetic construct
SEQUENCE: 9
LQEEDAGEYG CM                                                        12

SEQ ID NO: 10             moltype = AA  length = 6
FEATURE                   Location/Qualifiers
REGION                    1..6
                          note = TLT-1 peptide
source                    1..6
                          mol_type = protein
                          organism = synthetic construct
SEQUENCE: 10
LQEEDA                                                                6

SEQ ID NO: 11             moltype = AA  length = 6
FEATURE                   Location/Qualifiers
REGION                    1..6
                          note = TLT-1 peptide
source                    1..6
                          mol_type = protein
                          organism = synthetic construct
SEQUENCE: 11
EDAGEY                                                                6

SEQ ID NO: 12             moltype = AA  length = 6
FEATURE                   Location/Qualifiers
REGION                    1..6
                          note = TLT-1 peptide
source                    1..6
                          mol_type = protein
                          organism = synthetic construct
SEQUENCE: 12
GEYGCM                                                                6

SEQ ID NO: 13             moltype = DNA  length = 18
FEATURE                   Location/Qualifiers
misc_feature              1..18
                          note = primer
source                    1..18
```

```
                            mol_type = other DNA
                            organism = synthetic construct
SEQUENCE: 13
gtggtgacca aggggttc                                                    18

SEQ ID NO: 14               moltype = DNA   length = 20
FEATURE                     Location/Qualifiers
misc_feature                1..20
                            note = primer
source                      1..20
                            mol_type = other DNA
                            organism = synthetic construct
SEQUENCE: 14
agatggatgt ggctggaagt                                                  20

SEQ ID NO: 15               moltype = DNA   length = 20
FEATURE                     Location/Qualifiers
misc_feature                1..20
                            note = primer
source                      1..20
                            mol_type = other DNA
                            organism = synthetic construct
SEQUENCE: 15
gtgaccaagg gttttcagg                                                   20

SEQ ID NO: 16               moltype = DNA   length = 20
FEATURE                     Location/Qualifiers
misc_feature                1..20
                            note = primer
source                      1..20
                            mol_type = other DNA
                            organism = synthetic construct
SEQUENCE: 16
acaccggaac cctgatgata                                                  20

SEQ ID NO: 17               moltype = DNA   length = 19
FEATURE                     Location/Qualifiers
misc_feature                1..19
                            note = primer
source                      1..19
                            mol_type = other DNA
                            organism = synthetic construct
SEQUENCE: 17
aaaggcaaga acgcctgac                                                   19

SEQ ID NO: 18               moltype = DNA   length = 20
FEATURE                     Location/Qualifiers
misc_feature                1..20
                            note = primer
source                      1..20
                            mol_type = other DNA
                            organism = synthetic construct
SEQUENCE: 18
gggactttac caagagggac                                                  20

SEQ ID NO: 19               moltype = AA    length = 107
FEATURE                     Location/Qualifiers
source                      1..107
                            mol_type = protein
                            organism = Homo sapiens
SEQUENCE: 19
LKEGQTLDVK CDYTLEKFAS SQKAWQIIRD GEMPKTLACT ERPSKNSHPV QVGRIILEDY      60
HDHGLLRVRM VNLQVEDSGL YQCVIYQPPK EPHMLFDRIR LVVTKGF                   107
```

METHOD FOR TREATING SEPTIC SHOCK

CROSS-REFERENCE TO RELATED APPLICATIONS

This application is a continuation of U.S. patent application Ser. No. 17/280,358 filed Mar. 26, 2021, which is a U.S. national stage application filed under 35 U.S.C. § 371 of International Patent Application No. PCT/EP2019/076263 filed Sep. 27, 2019, which application claims priority to and the benefit of European Patent Application No. 18306277.7 filed Sep. 28, 2018.

REFERENCE TO A SEQUENCE LISTING XML

This application contains a Sequence Listing which has been submitted electronically in XML format. The Sequence Listing XML is incorporated herein by reference. Said XML file, created on Jun. 26, 2024, is named INTR-001US-_SL.xml and is 22,897 bytes in size.

FIELD OF INVENTION

The present invention relates to the treatment of an inflammatory disorder, preferably an acute inflammatory disorder, in human subjects, in particular in a subpopulation of human subjects susceptible to respond to a therapy, in particular to a TREM-1 inhibitor. The present invention thus relates to methods for identifying human subjects suffering from an inflammatory disorder, preferably an acute inflammatory disorder such as systemic inflammatory response syndrome (SIRS), sepsis or septic shock, susceptible to respond to a therapy, in particular to a TREM-1 inhibitor.

BACKGROUND OF INVENTION

Systemic inflammatory response syndrome (SIRS) is characterized by systemic inflammation and widespread tissue injury. SIRS may occur as a response to a nonspecific insult of either infectious or non-infectious origin. Examples of insults of non-infectious origin include, without being limited to, trauma, thermal injury, pancreatitis, autoimmune disorders and surgery. Examples of insults of infectious origin include bacterial infections fungal infections and viral infections.

Sepsis is defined as a life-threatening organ dysfunction caused by a dysregulated host response to infection (Singer et al., JAMA. 2016 Feb. 23; 315(8):801-10). Sepsis thus arises when the body's response to an infection injures its own tissues and organs, eventually leading to death in 30-50% of cases (Fleischmann et al., Dtsch Arztebl Int. 2016 Mar. 11; 113(10):159-66). Moreover, many survivors suffer from post-sepsis syndrome, reporting an increase in sensory, integumentary, digestive, breathing, chest pain, kidney and musculoskeletal problems after sepsis (Huang et al., Int J Qual Health Care. 2018 Jun. 19). According to the World Health Organization, it is estimated that sepsis affects more than 30 million people worldwide every year, potentially leading to 6 million deaths.

Septic shock is defined as a subset of sepsis in which particularly profound circulatory, cellular, and metabolic abnormalities are associated with a greater risk of mortality than with sepsis alone (Singer et al., JAMA. 2016 Feb. 23; 315(8):801-10). Clinically, patients with septic shock can be identified as sepsis patients (i) suffering from hypotension persisting after adequate fluid resuscitation requiring use of vasopressors to maintain mean blood pressure of 65 mm Hg or greater and (ii) having a serum lactate level greater than 2 mmol/L (Shankar-Hari et al., JAMA. 2016 Feb. 23; 315(8):775-87).

Currently, there is no specific causal treatment for sepsis or septic shock. Management of patients thus relies mainly on early recognition allowing correct therapeutic measures to be started rapidly, including administration of appropriate antibiotics, source control measures when necessary, and resuscitation with intravenous fluids and vasoactive drugs when needed (Cohen et al., Lancet Infect Dis. 2015 May; 15(5):581-614). Previous attempts to develop treatments have failed, including therapies targeting endotoxins and TLRs (Cuvier et al., Br J Clin Pharmacol. 2018 Jun. 8).

Recently, the Applicant developed a therapy which targets the TREM-1 (triggering receptor expressed on myeloid cells-1) pathway. TREM-1 is an immunoreceptor expressed by innate immune cells (monocyte/macrophages, neutrophils, platelets, dendritic cells) and endothelial cells. TREM-1 activation leads to cytokines and chemokines production along with rapid neutrophil degranulation and oxidative burst. TREM-1 function is to modulate/amplify, rather than activate/initiate, inflammation by synergizing with pathogen recognition receptors (PRRs), including Toll-like receptors (TLRs), in order to trigger an exuberant immune response. Notably, the TREM-1 pathway is involved in the pathophysiology of sepsis and septic shock. The Applicant thus showed that TREM-1 inhibitors, i.e., short TLT-1 (TREM-like transcript-1) peptides inhibiting TREM-1 activity, may be used in the treatment of inflammatory disorders, in particular acute inflammatory disorders such as systemic inflammatory response syndrome (SIRS), sepsis or septic shock (WO2011/124685). TLT-1 (Trem-Like Transcript-1) is a receptor, member of the TREM family, exclusively expressed by megakaryocytes and platelets.

However, for the TREM-1 inhibitor to provide the greatest therapeutic benefit in the treatment of an acute inflammatory disorder such as SIRS, sepsis or septic shock, there is still a need to identify the human subjects suffering from an acute inflammatory disorder susceptible to respond to a therapy, in particular to a TREM-1 inhibitor. Notably, there is still a need to identify the human subjects suffering from an acute inflammatory disorder such as SIRS, sepsis or septic shock susceptible to respond to a therapy, in particular to a TLT-1 peptide inhibiting TREM-1 activity.

SUMMARY

The Applicant now shows that measuring the level of soluble TREM-1 (sTREM-1) in a biological sample from human subjects suffering from septic shock and comparing their measured level of sTREM-1 to a predetermined sTREM-1 value allows to identify the human subjects suffering from septic shock susceptible to respond to a TREM-1 inhibitor. In particular, the Applicant shows that human subjects suffering from septic shock with a circulatory level of sTREM-1 higher than the median sTREM-1 level predetermined in a reference population of human subjects suffering from septic shock are more likely to respond to, and thus benefit from, the administration of a TLT-1 peptide inhibiting TREM-1 activity.

The present invention thus relates to an in vitro method for identifying a human subject suffering from an inflammatory disorder, preferably an acute inflammatory disorder such as SIRS, sepsis or septic shock, susceptible to respond to a therapy, in particular to a TREM-1 inhibitor, said method comprising:

a) measuring the level of soluble triggering receptors expressed on myeloid cells-1 (sTREM-1) in a biological sample from the human subject;
b) comparing the level of sTREM-1 measured at step a) to a predetermined sTREM-1 value;
c) identifying a human subject suffering from an inflammatory disorder, preferably an acute inflammatory disorder such as SIRS, sepsis or septic shock with a level of sTREM-1 measured at step a) higher than the predetermined sTREM-1 value of step b) as susceptible to respond to a therapy, in particular to a TREM-1 inhibitor.

The present invention also relates to a therapy, preferably a TREM-1 inhibitor, for use in the treatment of an inflammatory disorder, preferably an acute inflammatory disorder such as SIRS, sepsis or septic shock, in a subject in need thereof, wherein a level of sTREM-1 measured in a biological sample from the subject and higher than a predetermined sTREM-1 value indicates that the subject is susceptible to respond to the therapy, preferably to the TREM-1 inhibitor.

The present invention thus relates to an in vitro method for identifying a human subject suffering from an inflammatory disorder susceptible to respond to a therapy, preferably to a TREM-1 inhibitor, said method comprising:
a) measuring the level of soluble Triggering Receptors Expressed on Myeloid cells-1 (sTREM-1) in a biological sample from the human subject;
b) comparing the level of sTREM-1 measured at step a) to a predetermined sTREM-1 value;
c) identifying a human subject suffering from an inflammatory disorder with a level of sTREM-1 measured at step a) higher than the predetermined sTREM-1 value of step b) as susceptible to respond to a therapy, preferably to a TREM-1 inhibitor.

In one embodiment, the predetermined sTREM-1 value of step b) is obtained from a reference population. In one embodiment, the reference population is a population of human patients suffering from an inflammatory disorder, preferably systemic inflammatory response syndrome (SIRS), sepsis or septic shock.

In one embodiment, the predetermined sTREM-1 value of step b) is the sTREM-1 median in the reference population or the sTREM-1 third quartile in the reference population.

In one embodiment, the level of sTREM-1 measured at step a) is a level measured before the beginning of the therapy, preferably before the administration of a TREM-1 inhibitor. In one embodiment, the level of sTREM-1 measured at step a) is measured within the first 24 hours following the diagnosis or the hospitalization of the human subject for an inflammatory disorder.

In one embodiment, the biological sample is a blood sample, a serum sample or a plasma sample.

In one embodiment, the level of sTREM-1 measured at step a) is a protein level, preferably measured by ELISA, electrochemiluminescence (ECL) also referred as electrochemiluminescence immunoassay (ECLIA) or enzyme-linked fluorescent assay (ELFA).

In one embodiment, the therapy comprises the administration of a TREM-1 inhibitor, preferably selected from the group consisting of peptides inhibiting the function, activity or expression of TREM-1; antibodies directed to TREM-1 and/or sTREM-1, or TREM-1 and/or sTREM-1 ligand; small molecules inhibiting the function, activity or expression of TREM-1; siRNAs directed to TREM-1; shRNAs directed to TREM-1; antisense oligonucleotide directed to TREM-1; ribozymes directed to TREM-1 and aptamers directed to TREM-1. In one embodiment, the therapy comprises the administration of a TREM-1 inhibitor, said TREM-1 inhibitor being a peptide targeting sTREM-1 ligand, preferably a peptide having an amino acid sequence selected from the group consisting of SEQ ID NO: 8, SEQ ID NO: 9, SEQ ID NO: 10, SEQ ID NO: 11, and SEQ ID NO: 12. In one embodiment, the therapy comprises the administration of a TREM-1 inhibitor, said TREM-1 inhibitor being a peptide having an amino acid sequence as set forth in SEQ ID NO: 9.

In one embodiment, the therapy is a TREM-1 inhibitor, preferably selected from the group consisting of peptides inhibiting the function, activity or expression of TREM-1; antibodies directed to TREM-1 and/or sTREM-1, or TREM-1 and/or sTREM-1 ligand; small molecules inhibiting the function, activity or expression of TREM-1; siRNAs directed to TREM-1; shRNAs directed to TREM-1; antisense oligonucleotide directed to TREM-1; ribozymes directed to TREM-1 and aptamers directed to TREM-1. In one embodiment, the TREM-1 inhibitor is a peptide inhibiting the function, activity or expression of TREM-1 by targeting TREM-1 ligand, preferably a peptide having an amino acid sequence selected from the group consisting of SEQ ID NO: 8, SEQ ID NO: 9, SEQ ID NO: 10, SEQ ID NO: 11, and SEQ ID NO: 12. In one embodiment, the TREM-1 inhibitor is a peptide having an amino acid sequence as set forth in SEQ ID NO: 9.

In one embodiment, the inflammatory disorder is selected from the group comprising systemic inflammatory response syndrome (SIRS), sepsis and septic shock, preferably the inflammatory disorder is septic shock. In one embodiment, the human subject is suffering from an organ dysfunction defined as an acute change in his/her sequential organ failure assessment (SOFA) score of at least 2 points.

In one embodiment, a human subject suffering from SIRS, sepsis or septic shock susceptible to respond to a therapy, preferably to a TREM-1 inhibitor, is a human subject susceptible to have his/her sequential organ failure assessment (SOFA) score decrease following the administration of the therapy, preferably following the administration of a TREM-1 inhibitor. In one embodiment, a human subject suffering from septic shock susceptible to respond to a therapy, preferably to a TREM-1 inhibitor, is a human subject suffering from septic shock susceptible to reverse a hypotensive shock within or after the administration period of the therapy, preferably of a TREM-1 inhibitor, wherein a hypotensive shock reversal is defined as the absence of any vasopressor therapy during 24 hours.

Definitions

In the present invention, the following terms have the following meanings:
"About" preceding a figure encompasses plus or minus 10%, or less, of the value of said figure. It is to be understood that the value to which the term "about" refers is itself also specifically, and preferably, disclosed.
"APACHE II" refers to "Acute Physiology And Chronic Health Evaluation II". APACHE II is a scoring system commonly used to assess the severity of disease in adult patients admitted in intensive care units and determine their prognostic. APACHE II uses a point score ranging from 0 to 71 that is based upon the initial values of 12 routine physiologic measurements (i.e., variables), age, and previous health status to provide a general measure of severity of disease (Knaus et al., Crit Care Med. 1985 October; 13(10):818-29).

"APACHE III" refers to "Acute Physiology And Chronic Health Evaluation III". APACHE III is a scoring system that was redefined from the APACHE II scoring system in order to more accurately predict hospital mortality risk for critically ill hospitalized adults (Knaus et al., Chest. 1991 December; 100(6):1619-36). The APACHE III scoring system is similar to the APACHE II scoring system, except that several variables have been added to those used in the APACHE II scoring system so that 17 variables are computed into a point score ranging from 0 to 299.

"APACHE IV" refers to "Acute Physiology And Chronic Health Evaluation IV". APACHE IV is an improved and updated model for estimating the risk of short-term mortality as well as predicting the length of intensive care unit (ICU) stay (Zimmerman et al., Crit Care Med. 2006 May; 34(5):1297-310). In the APACHE IV scoring system, a greater number of variables are considered, notably mechanical ventilation, thrombolysis, impact of sedation on Glasgow Coma Scale, rescaled Glasgow Coma Scale, $PaO_2/FiO_2$ ratio and disease-specific subgroups. APACHE IV uses a point score ranging from 0 to 286.

"Electrochemiluminescence immunoassay (ECLIA)" refers to an immunoassay wherein the detection of the signal is based on electrochemiluminescence, i.e., a form of chemiluminescence in which the light-emitting chemiluminescent reaction is preceded by an electrochemical reaction.

"Fluid therapy" refers to a therapy aiming at restoring and/or maintaining the volume and composition of the body fluids to normal, in particular with respect to the water-electrolyte balance. Fluid therapy thus aims at correcting and/or preventing volume and/or electrolyte deficit.

"Immunodeficient" refers to a subject whose ability to develop a normal immune response, for example to fight an infectious disease or a cancer, is compromised or entirely absent. Similarly, "immunocompromised" refers to a subject whose ability to develop a normal immune response, for example to fight an infectious disease or a cancer, is compromised. "Immunosuppressed" refers to a subject in whom the activation or efficacy of the immune system is reduced, notably through the administration of an immunosuppressive therapy. For example, immunosuppression in a subject may be assessed through the measure of PD-1 level, the measure of circulatory IL-7 level, or the measure of HLA-DR.

"Measuring" or "measurement", or alternatively "detecting" or "detection", means assessing the presence, absence, quantity, or amount (which can be an effective amount) of a given substance, i.e., sTREM-1, within a biological sample from a human subject. "Measuring" or "measurement", or alternatively "detecting" or "detection" as used herein include the derivation of the qualitative or quantitative concentration of said substance, i.e., sTREM-1, within the biological sample and within the human subject (e.g., blood concentration or plasma concentration).

"Organ dysfunction score" or "organ dysfunction scoring system" as used herein refers to a score used to assess organ dysfunction in a human subject, notably in a human subject suffering from SIRS, sepsis or septic shock, upon hospitalization, in particular upon admission in ICU or emergency unit. Examples of organ dysfunction scores include, without being limited to, the SOFA score, the qSOFA score, the MODS (Multiple Organ Dysfunction Score), the P-MODS (Pediatric Multiple Organ Dysfunction Score) and the LODS (Logistic Organ Dysfunction System).

"qSOFA score" refers to the quick SOFA score (also known as quickSOFA). The qSOFA scoring system relies on three criteria: respiratory rate ≥22 breaths/min; altered mentation (Glasgow coma scale <15); and systolic blood pressure ≥100 mm Hg (Seymour et al., JAMA. 2016 Feb. 23; 315(8):762-74).

"Quantile(s)" refers to (a) cut-off value(s) dividing the observations/measures made in a population into equal-sized groups, each group comprising an equal percentage of said observations/measures. As used herein, "quantile(s)" thus refer to cut-off sTREM-1 value(s) dividing the sTREM-1 level measured in a biological sample from each of the human subjects of a reference population into equal-sized groups each comprising an equal percentage of said measures of sTREM-1 level. In other words, "quantile(s)" refers to cut-off sTREM-1 value(s) below or above which lies a determined percentage of the sTREM-1 levels measured in a reference population. For example, as used herein, "quartiles" refer to the three cut-off sTREM-1 values dividing the sTREM-1 level measured in a reference population into four groups, each comprising 25% of the sTREM-1 levels measured in the reference population. It should be noted that "quantiles" may also sometimes refer to the groups so defined by said cut-off value. For example, "quartiles" may also sometimes refer to the four groups defined by the three cut-off sTREM-1 values so dividing the sTREM-1 level measured in a reference population. However, as used herein and unless otherwise specified, the term "quantile" refers to a cut-off value.

"SAPS" refers to "Simplified Acute Physiology Score". SAPS is a scoring system reflecting the risk of death in ICU patients. SAPS relies on 14 biological and clinical variables (Le Gall et al., Crit Care Med. 1984 November; 12(11):975-7).

"SAPS II" refers to "Simplified Acute Physiology Score II". SAPS II is a scoring system for estimating in-hospital mortality in adult patients admitted to the intensive care unit (ICU). SAPS II include 17 variables: 12 physiology variables, age, type of admission, and 3 variables regarding underlying diseases (Le Gall et al., JAMA. 1993 Dec. 22-29; 270(24):2957-63). SAPS II uses a point score ranging from 0 to 163.

"SAPS 3" refers to "Simplified Acute Physiology Score III". SAPS 3 is a scoring system for predicting hospital mortality of patients admitted to the intensive care unit (ICU) (Metnitz et al., Intensive Care Med. 2005 October; 31(10): 1336-1344 and Moreno et al., Intensive Care Med. 2005 October; 31(10):1345-55). SAPS 3 is based on 20 different variables.

"Severity score" or "severity scoring system" as used herein refer to a score used to assess the severity of the disease and/or the prognosis of human subjects, notably of human subjects suffering from SIRS, sepsis or septic shock, upon admission in ICU or emergency unit. Examples of severity scores include, without being limited to, the APACHE II score, the APACHE III score, the APACHE IV score, the SAPS score, the SAPS II score and the SAPS 3 score.

"SIRS, sepsis or septic shock therapy" as used herein refers to a therapy administered to a subject in need thereof for the treatment of SIRS, sepsis or septic shock. In one embodiment, the SIRS, sepsis or septic shock therapy is an immunomodulatory or an anti-inflammatory therapy. Examples of immunomodulatory or an anti-inflammatory therapies include, without being limited to, checkpoint inhibitors such as anti-PD-1, anti-PD-L1 and anti-CTLA4; TLR (Toll-like receptors) inhibitors; cytokine inhibitors such as anti-cytokine or anti-cytokine receptors (for example IL-1RA for interleukin-1 receptor antagonist); G-CSF (granulocyte-colony stimulating factor); IL-7 (interleukin-7); inhibitors of immunostimulants such as CD28 antagonist peptides and antibodies, in particular monoclonal antibodies, against CD28; and cellular therapies such as adoptive cell therapies. In one embodiment, the SIRS, sepsis or septic shock therapy is an angiogenesis inhibitor, in particular an angiopoietin-2 (Ang-2 or Ang2) inhibitor. In one embodiment, the SIRS, sepsis or septic shock therapy is a TREM-1 inhibitor. In one embodiment, the TREM-1 inhibitor is a peptide targeting TREM-1 ligand, preferably a peptide having an amino acid sequence selected from the group consisting of SEQ ID NO: 8, SEQ ID NO: 9, SEQ ID NO: 10, SEQ ID NO: 11, and SEQ ID NO: 12.

"Shock" or "hypotensive shock" or "distributive shock" refer to a diminished or insufficient perfusion that impairs organ function and is generally associated with decreased arterial blood pressure. A hypotensive shock may be unresponsive to fluid resuscitation and require a vasopressor therapy to increase the arterial blood pressure, restore effective tissue perfusion and normalize cellular metabolism.

"Shock reversal" or "hypotensive shock reversal" as used herein are defined as the absence of any vasopressor therapy during at least 24 hours (i.e., not requiring to restart a vasopressor therapy in the 24 hours following the end of a vasopressor therapy). In one embodiment, shock reversal may occur within the administration period of the SIRS, sepsis or septic shock therapy. In one embodiment, shock reversal may occur 6, 12, 18, 24, 30, 36, 42, 48, 54, 60, 66 or 72 hours following the start of the administration of the SIRS, sepsis or septic shock therapy. In one embodiment, shock reversal may occur after the administration period of the SIRS, sepsis or septic shock therapy. In one embodiment, shock reversal may occur 6, 12, 18, 24, 30, 36, 42, 48, 54, 60, 66 or 72 hours following the end of the administration of the SIRS, sepsis or septic shock therapy.

"SOFA score" refers to the Sequential Organ Failure Assessment (SOFA) score (originally referred to as the Sepsis-related Organ Failure Assessment) which is commonly used to assess the presence of organ dysfunction. The SOFA scoring system (Vincent et al., Crit Care Med. 1998 November; 26(11):1793-800) relies on the assessment of the respiratory system (i.e., PaO2/FiO2 (mmHg)); of the nervous system (i.e., Glasgow coma scale); of the cardiovascular system (i.e., mean arterial pressure or administration of vasopressors required); of the liver function (i.e., bilirubin (mg/dL or µmol/L)); of coagulation (i.e., platelet count); and of the kidney function (i.e., creatinine (mg/dL or µmol/L) or urine output (mL/d)).

"Standard of care" refers to the care routinely provided to a patient suffering from an inflammatory disorder, in particular systemic inflammatory response syndrome (SIRS), sepsis or septic shock. In one embodiment, the patient is suffering from a septic shock and the standard of care includes at least one of antimicrobial therapy, fluid therapy, vasopressor therapy, cardiovascular support, respiratory support, renal support, and sedation.

"TREM-1" refers to "triggering receptors expressed on myeloid cells-1". TREM-1 is a membrane-bound glycoprotein receptor belonging to the Ig superfamily that is notably expressed on myeloid cells. TREM-1 activates downstream signaling pathways with the help of an adapter protein called DAP12. TREM-1 comprises three distinct domains: an Ig-like structure (mostly responsible for ligand binding), a transmembrane part and a cytoplasmic tail with associates with DAP12. Unless specified otherwise, the TREM-1 protein has an amino acid sequence as set forth in SEQ ID NO: 1, corresponding to UniProtKB/Swiss-Prot accession number Q9NP99-1, last modified on Oct. 1, 2000 and to UniProtKB accession number Q38L15-1, last modified on Nov. 22, 2005. Several transcripts are known for TREM-1. The transcript commonly referred to as TREM1-201 (transcript ID ensembl ENST00000244709.8) encodes an amino acid sequence as set forth in SEQ ID NO: 1. The transcript commonly referred to as TREM1-202, also known as TREM-1 isoform 2 (ensembl transcript ID ENST00000334475.10) encodes an amino acid sequence as set forth in SEQ ID NO: 2 (corresponding to UniProtKB/Swiss-Prot accession number Q9NP99-2). The transcript commonly referred to as TREM1-207, also known as TREM-1 isoform 3 (ensembl transcript ID ENST00000591620.1) encodes an amino acid sequence as set forth in SEQ ID NO: 3 (corresponding to UniProtKB/Swiss-Prot accession number Q9NP99-3). The transcript commonly referred to as TREM1-204 (ensembl transcript ID ENST00000589614.5) encodes an amino acid sequence as set forth in SEQ ID NO: 4 (corresponding to UniProtKB/Swiss-Prot accession number K7EKM5-1, last modified Jan. 9, 2013).

"sTREM-1", for "soluble triggering receptors expressed on myeloid cells-1", refers to a soluble form of TREM-1 lacking the transmembrane and intracellular domains of TREM-1. In one embodiment, sTREM-1 thus corresponds to the soluble form of the extracellular domain of TREM-1. The soluble TREM-1 may be generated by proteolytic cleavage of TREM-1 Ig-like ectodomain from the membrane-anchored TREM-1 by matrix metalloproteinases (Gomez-Pina et al., J Immunol. 2007 Sep. 15; 179(6):4065-73). In one embodiment, sTREM-1 thus corresponds to a truncated TREM-1 shed from the membrane of myeloid cells, in particular from activated myeloid cells. It was also suggested that sTREM-1 results from an alternative splicing of TREM-1 mRNA. A TREM-1 splice variant was characterized in 2015 by Baruah et al. (J Immunol. 2015 Dec. 15; 195(12):5725-31), and was found to be secreted from primary and secondary human neutrophil granules In one embodiment, sTREM-1 thus corresponds to a TREM-1 splice variant, in particular to the TREM-1 transcript commonly referred to as TREM1-202, also known as TREM-1 isoform 2, encoding an amino acid sequence as set forth in SEQ ID NO: 2.

"sTREM-1 median" as used herein refers to a predetermined sTREM-1 value obtained from a reference population dividing the sTREM-1 levels measured in said reference population into two groups, each comprising 50% of the sTREM-1 levels measured in said reference population.

"sTREM-1 terciles" as used herein refers to predetermined sTREM-1 values obtained from a reference population dividing the sTREM-1 levels measured in said reference population into three groups, each comprising a third of the sTREM-1 levels measured in said reference population. In one embodiment, the sTREM-1 tercile is the last sTREM-1 tercile (i.e., the sTREM-1 second tercile), corresponding to the sTREM-1 value below which two thirds of the sTREM-1 levels measured in the reference population lie and above which one third of the sTREM-1 levels measured in the reference population lie.

"sTREM-1 quartiles" as used herein refers to predetermined sTREM-1 values obtained from a reference population dividing the sTREM-1 levels measured in said reference population into four groups, each comprising 25% of the sTREM-1 levels measured in said reference population. In one embodiment, the sTREM-1 quartile is the last sTREM-1 quartile (i.e., the sTREM-1 third quartile also referred to as Q3), corresponding to the sTREM-1 value below which 75% of the sTREM-1 levels measured in the reference population lie and above which 25% of the sTREM-1 levels measured in the reference population lie.

"sTREM-1 quintiles" as used herein refers to predetermined sTREM-1 values obtained from a reference population dividing the sTREM-1 levels measured in said reference population into five groups, each comprising 20% of the sTREM-1 levels measured in said reference population. In one embodiment, the sTREM-1 quintile is the last sTREM-1 quintile (i.e., the sTREM-1 fourth quintile), corresponding to the sTREM-1 value below which 80% of the sTREM-1 levels measured in the reference population lie and above which 20% of the sTREM-1 levels measured in the reference population lie.

"sTREM-1 deciles" as used herein refers to predetermined sTREM-1 values obtained from a reference population dividing the sTREM-1 levels measured in said reference population into ten groups, each comprising 10% of the sTREM-1 levels measured in said reference population. In one embodiment, the sTREM-1 decile is the last sTREM-1 decile (i.e., the sTREM-1 ninth decile), corresponding to the sTREM-1 value below which 90% of the sTREM-1 levels measured in the reference population lie and above which 10% of the sTREM-1 levels measured in the reference population lie.

"sTREM-1 percentiles" as used herein refers to a predetermined sTREM-1 value obtained from a reference population dividing the sTREM-1 levels measured in said reference population into groups corresponding to a given percentage of the sTREM-1 levels measured in the reference population. As used herein, a sTREM-1 percentile is thus a predetermined sTREM-1 value obtained from a reference population below which a given percentage of the sTREM-1 levels measured in said reference population lies. For example, the 40th percentile is the sTREM-1 value obtained from a reference population below which 40% of the sTREM-1 levels measured in said reference population lie.

"Therapeutically effective amount" or "therapeutically effective dose" refer to the amount or dose of therapy, preferably a TREM-1 inhibitor, that is aimed at, without causing significant negative or adverse side effects to the human subject, (1) delaying or preventing the onset of an inflammatory disorder, preferably SIRS, sepsis or septic shock, in the human subject; (2) reducing the severity or incidence of an inflammatory disorder, preferably SIRS, sepsis or septic shock; (3) slowing down or stopping the progression, aggravation, or deterioration of one or more symptoms of an inflammatory disorder, preferably SIRS, sepsis or septic shock, affecting the human subject; (4) bringing about ameliorations of the symptoms of an inflammatory disorder, preferably SIRS, sepsis or septic shock, affecting the human subject; or (5) curing an inflammatory disorder, preferably SIRS, sepsis or septic shock, affecting the human subject. In one embodiment, the administration of a therapeutically effective dose (or amount) of a therapy, preferably of TREM-1 inhibitor, to a human subject suffering from an inflammatory disorder, preferably SIRS, sepsis or septic shock, aims at inducing in said subject at least one of the following:

a reversal of a hypotensive shock, preferably within or after the administration period of the therapy, preferably a TREM-1 inhibitor, for example over the 6, 12, 18 or 24 hours following the end of said administration, wherein a hypotensive shock reversal is defined as the absence of any vasopressor therapy during at least 24 hours (i.e., not requiring to restart a vasopressor therapy in the 24 hours following the end of a vasopressor therapy);

a decrease of a severity score used to assess the severity of the disease and/or the prognosis of subjects suffering from an inflammatory disorder, preferably SIRS, sepsis or septic shock, upon admission in ICU or emergency unit, such as the APACHE II score, the APACHE III score, the APACHE IV score, the SAPS score, the SAPS II score or the SAPS 3 score;

a decrease of an organ dysfunction score used to assess the presence of organ dysfunction in a human subject suffering from an inflammatory disorder, preferably SIRS, sepsis or septic shock, upon admission in ICU or emergency unit, such as the SOFA score, the qSOFA score, the MODS (Multiple Organ Dysfunction Score), the P-MODS (Pediatric Multiple Organ Dysfunction Score) or the LODS (Logistic Organ Dysfunction System);

a decrease of the SOFA score and/or of the qSOFA score, in particular over the 1, 2, 3, 4, 5, 6 or 7 day(s) following the start of the administration of the therapy, preferably a TREM-1 inhibitor, preferably with reference to the SOFA score and/or the qSOFA score assessed upon admission in ICU or emergency unit or before the start of the administration of the therapy; in one embodiment, said decrease of the SOFA score is a decrease of at least 1 point (also referred as a delta of −1 point or ΔSOFA of −1 point), preferably of at least 1.5 point, in particular at day 3 or at day 5 following the start of the administration of the therapy, preferably with reference to the SOFA score and/or the qSOFA score assessed upon admission in ICU or emergency unit or before the start of the administration of the therapy;

a decrease in the requirement for cardiovascular support, for example a decrease in the use of vasopressor therapy, in particular over the 1, 2, 3, 4, 5, 6 or 7 day(s) following the start of the administration of the therapy, preferably a TREM-1 inhibitor, preferably with reference to the requirement for cardiovascular support upon admission in ICU or emergency unit or before the start of the administration of the therapy;

a decrease in the requirement for respiratory support, for example a decrease in the use of invasive mechanical ventilation (IMV), in particular over the 1, 2, 3, 4, 5, 6 or 7 day(s) following the start of the administration of the therapy, preferably a TREM-1 inhibitor, preferably with reference to the requirement for respiratory support upon admission in ICU or emergency unit or before the start of the administration of the therapy;

a decrease in the requirement for renal support, for example a decrease in the use of continuous or discontinuous renal replacement therapy also referred to as RRT (e.g., dialysis), in particular over the 1, 2, 3, 4, 5, 6 or 7 day(s) following the start of the administration of the therapy, preferably a TREM-1 inhibitor, preferably with reference to the requirement for renal support upon admission in ICU or emergency unit or before the start of the administration of the therapy;

a decrease in the risk of reinfection, in particular a decrease in the risk of reinfection in the 28, 90 or 365 days following the initial inflammatory disorder, in particular the initial infection responsible for an inflammatory disorder;

an absence of reinfection, in particular an absence of reinfection in the 28, 90 or 365 days following the initial inflammatory disorder, in particular the initial infection responsible for an inflammatory disorder;

a decrease in the risk of rehospitalization, in particular a decrease in the risk of rehospitalization in the 28, 90 or 365 days following the initial inflammatory disorder, in particular the initial infection responsible for an inflammatory disorder;

an absence of rehospitalization, in particular an absence of rehospitalization in the 28, 90 or 365 days following the first hospitalization;

an increase in the chance of survival, in particular 1-year, 2-year, 3-year, 4-year, 5-year, 6-year, 7-year, 8-year, 9-year or 10-year survival, following the start of the administration of the therapy, preferably a TREM-1 inhibitor; in one embodiment the chance of survival, in particular in a subject with multiple comorbidities, is assessed with the Charlson Comorbidity Index (CCI) and an increase in the chance of 10-year survival corresponds to a decrease of the Charlson Comorbidity Index, preferably with reference to CCI assessed upon admission in ICU or emergency unit or before the start of the administration of the therapy;

a decrease in the risk of sepsis-related death, in particular at day 5, day 28, day 90 or day 365 following the start of the administration of the therapy, preferably a TREM-1 inhibitor;

a decrease in the risk of the all-cause death, in particular at day 5, day 28, day 90 or day 365 following the start of the administration of the therapy, preferably a TREM-1 inhibitor;

a decrease in the risk of post-sepsis or post-shock morbidity, in particular at day 5, day 28, day 90 or day 365 following the start of the administration of the therapy, preferably a TREM-1 inhibitor;

an increase in the quality of life, in particular in the post-sepsis or post-shock quality of life that may be assessed for example through an evaluation of survival and quality-adjusted life years (QALYs), estimated from the EuroQoL Quality of Life Scale commonly known as EQ5D. For example, health-related quality of life (HRQoL) scores from the EQ 5D 5L (5-level EQ-5D version) may be calculated and converted to utility scores, in particular at 3 months, 6 months, 9 months, 12 months, 18 months, 24 months or 36 months following the start of the administration of the therapy.

a decrease in the level of an inflammatory marker, such as, for example, CRP or IL6, IL-8, IL-10, MCP-1 and TNF-α), in particular over the 1, 2, 3, 4, 5, 6 or 7 day(s) following the start of the administration of the therapy, preferably a TREM-1 inhibitor, preferably with reference to the level assessed upon admission in ICU or emergency unit or before the start of the administration of the therapy; or a decrease in the level of an endothelial injury marker, such as, for example, Ang-2, VCAM-1, VGEFR-1 and E-selectin, in particular over the 1, 2, 3, 4, 5, 6 or 7 day(s) following the start of the administration of the therapy, preferably a TREM-1 inhibitor, preferably with reference to the level assessed upon admission in ICU or emergency unit or before the start of the administration of the therapy.

A therapeutically effective amount of a therapy, preferably a TREM-1 inhibitor, may be administered for a prophylactic or preventive action prior to the onset of an inflammatory disorder, preferably SIRS, sepsis or septic shock; prior to the diagnosis of an inflammatory disorder, preferably SIRS, sepsis or septic shock; prior to the admission to ICU or emergency unit; or prior to the start of vasopressor therapy. Alternatively, or additionally, a therapeutically effective amount of a therapy, preferably a TREM-1 inhibitor, may be administered for a therapeutic action after the onset of an inflammatory disorder, preferably SIRS, sepsis or septic shock; after the diagnosis of an inflammatory disorder, preferably SIRS, sepsis or septic shock; after the admission to ICU or emergency unit; or after start of vasopressor therapy.

"TLT-1" refers to TREM-like transcript-1. TLT-1 is a receptor, member of the TREM family, exclusively expressed by megakaryocytes and platelets. TLT-1 contains a v-set Ig type-extracellular domain, a transmembrane region and a cytoplasmic tail that comprises an immunoreceptor tyrosine based inhibitory motif (ITIM) and a polyproline-rich domain.

"Treating" or "treatment" refers to therapeutic treatment, to prophylactic or preventative measures, or to both, wherein the object is to prevent, slow down (lessen) or cure the targeted pathologic condition or disorder, i.e., an inflammatory disorder, preferably SIRS, sepsis or septic shock. In one embodiment of the present invention, "treating" or "treatment" refers to a therapeutic treatment. In another embodiment of the present invention, "treating" or "treatment" refers to a prophylactic or preventive treatment. In yet another embodiment of the present invention, "treating" or "treatment" refers to both a prophylactic (or preventive) treatment and a therapeutic treatment. Those in need of treatment include those already suffering from an inflammatory disorder, preferably SIRS, sepsis or septic shock, as well as those prone to develop an inflammatory disorder, preferably SIRS, sepsis or septic shock, or those in whom an inflammatory disorder, preferably SIRS, sepsis or septic shock is to be prevented. A human subject suffering from an inflammatory disorder, preferably SIRS, sepsis or septic shock, is successfully "treated"

if, after being administered a therapeutically effective amount of a therapy, preferably a TREM-1 inhibitor, the human subject shows at least one of the following:

a reversal of a hypotensive shock, preferably within or after the administration period of the therapy, preferably a TREM-1 inhibitor, for example over the 6, 12, 18 or 24 hours following the end of said administration, wherein a hypotensive shock reversal is defined as the absence of any vasopressor therapy during at least 24 hours (i.e., not requiring to restart a vasopressor therapy in the 24 hours following the end of a vasopressor therapy);

a decrease of a severity score used to assess the severity of the disease and/or the prognosis of subjects suffering from an inflammatory disorder, preferably SIRS, sepsis or septic shock upon admission in ICU or emergency unit, such as the APACHE II score, the APACHE III score, the APACHE IV score, the SAPS II score or the SAPS 3 score;

a decrease of an organ dysfunction score used to assess the presence of organ dysfunction in a human subject suffering from an inflammatory disorder, preferably SIRS, sepsis or septic shock upon admission in ICU or emergency unit, such as the SOFA score, the qSOFA score, the MODS (Multiple Organ Dysfunction Score), the P-MODS (Pediatric Multiple Organ Dysfunction Score) or the LODS (Logistic Organ Dysfunction System);

a decrease of the SOFA score and/or of the qSOFA score, in particular over the 1, 2, 3, 4, 5, 6 or 7 day(s) following the start of the administration of therapy, preferably a TREM-1 inhibitor, preferably with reference to the SOFA score and/or the qSOFA score assessed upon admission in ICU or emergency unit or before the start of the administration of the therapy; in one embodiment, said decrease of the SOFA score is a decrease of at least 1 point (also referred as a delta of −1 point or ΔSOFA of −1 point), preferably of at least 1.5 point, in particular at day 3 or at day 5 following the start of the administration of the therapy, preferably with reference to the SOFA score and/or the qSOFA score assessed upon admission in ICU or emergency unit or before the start of the administration of the therapy;

a decrease in the requirement for cardiovascular support, for example a decrease in the use of vasopressor therapy, in particular over the 1, 2, 3, 4, 5, 6 or 7 day(s) following the start of the administration of the therapy, preferably a TREM-1 inhibitor, preferably with reference to the requirement for cardiovascular support upon admission in ICU or emergency unit or before the start of the administration of the therapy;

a decrease in the requirement for respiratory support, for example a decrease in the use of invasive mechanical ventilation (IMV), in particular over the 1, 2, 3, 4, 5, 6 or 7 day(s) following the start of the administration of the therapy, preferably a TREM-1 inhibitor, preferably with reference to the requirement for respiratory support upon admission in ICU or emergency unit or before the start of the administration of the therapy;

a decrease in the requirement for renal support, for example a decrease in the use of continuous or discontinuous renal replacement therapy also referred to as RRT (e.g., dialysis), in particular over the 1, 2, 3, 4, 5, 6 or 7 day(s) following the start of the administration of the therapy, preferably a TREM-1 inhibitor, preferably with reference to the requirement for renal support upon admission in ICU or emergency unit or before the start of the administration of the therapy;

a decrease in the risk of reinfection, in particular a decrease in the risk of reinfection in the 28, 90 or 365 days following the initial inflammatory disorder, in particular the initial infection responsible for an inflammatory disorder;

an absence of reinfection, in particular an absence of reinfection in the 28, 90 or 365 days following the initial inflammatory disorder, in particular the initial infection responsible for an inflammatory disorder;

a decrease in the risk of rehospitalization, in particular a decrease in the risk of reinfection in the 28, 90 or 365 days following the initial inflammatory disorder, in particular the initial infection responsible for an inflammatory disorder;

an absence of rehospitalization, in particular an absence of rehospitalization in the 28, 90 or 365 days following the first hospitalization;

an increase in the chance of survival, in particular 1-year, 2-year, 3-year, 4-year, 5-year, 6-year, 7-year, 8-year, 9-year or 10-year survival, following the start of the administration of the therapy, preferably a TREM-1 inhibitor; in one embodiment the chance of survival, in particular in a subject with multiple comorbidities, is assessed with the Charlson Comorbidity Index (CCI) and an increase in the chance of 10-year survival corresponds to a decrease of the Charlson Comorbidity Index, preferably with reference to CCI assessed upon admission in ICU or emergency unit or before the start of the administration of the therapy;

a decrease in the risk of sepsis-related death, in particular at day 5, day 28, day 90 or day 365 following the start of the administration of the therapy, preferably a TREM-1 inhibitor;

a decrease in the risk of the all-cause death, in particular at day 5, day 28, day 90 or day 365 following the start of the administration of the therapy, preferably a TREM-1 inhibitor;

a decrease in the risk of post-sepsis or post-shock morbidity, in particular at day 5, day 28, day 90 or day 365 following the start of the administration of the therapy, preferably a TREM-1 inhibitor;

an increase in the quality of life, in particular in the post-sepsis or post-shock quality of life, that may be assessed for example through an evaluation of survival and quality-adjusted life years (QALYs), estimated from the EQ5D. For example, health-related quality of life (HRQoL) scores from the EQ 5D 5L may be calculated and converted to utility scores, in particular at 3 months, 6 months, 9 months, 12 months, 18 months, 24 months or 36 months following the start of the administration of the therapy;

a decrease in the level of an inflammatory marker, such as, for example, CRP or IL6, IL-8, IL-10, MCP-1 and TNF-α), in particular over the 1, 2, 3, 4, 5, 6 or 7 day(s) following the start of the administration of the therapy, preferably a TREM-1 inhibitor, preferably with reference to the level assessed upon admission in ICU or emergency unit or before the start of the administration of the therapy; or a decrease in the level of an endothelial injury marker, such as, for example, Ang-2, VCAM-1, VGEFR-1 and E-selectin, in particular over the 1, 2, 3, 4, 5, 6 or 7 day(s) following the start of the administration of the therapy, preferably a TREM-1 inhibitor, preferably with reference to the level assessed upon admission in ICU or emergency unit or before the start of the administration of the therapy.

The above parameters for assessing successful treatment and improvement in the disease are readily measurable by routine procedures familiar to a physician.

"TREM-1 inhibitor" refers to an active agent able to inhibit TREM-1 function, activity or expression. Example of TREM-1 inhibitors include, without begin limited to, peptides inhibiting the function, activity or expression of TREM-1; antibodies directed to TREM-1 and/or sTREM-1, or TREM-1 and/or sTREM-1 ligand; small molecules inhibiting the function, activity or expression of TREM-1; siRNAs directed to TREM-1; shRNAs directed to TREM-1; antisense oligonucleotide directed to TREM-1; ribozymes directed to TREM-1 and aptamers directed to TREM-1.

"Vasopressor therapy" refers to a therapy used in the treatment of shock, i.e., hypotensive shock, defined as a diminished or insufficient perfusion that impairs organ function and is generally associated with decreased arterial blood pressure. In particular, vasopressor therapy is required when the hypotension is unresponsive to fluid resuscitation. Vasopressor therapy aims at increasing the arterial blood pressure and maintaining an adequate blood pressure, restoring effective tissue perfusion and normalizing cellular metabolism. Examples of vasopressor therapies include, without limitation, the administration of vasoactive catecholamine hormones such as norepinephrine, dopamine, epinephrine; vasopressin; and/or phenylephrine.

BRIEF DESCRIPTION OF THE DRAWINGS

FIG. 1A is a graph showing TREM-1 expression by flow cytometry on U937 (grey) and U937-vitD cells (dark-grey) compared to isotype control (light-grey). FIG. 1B is a set of photographs showing TREM-1 expression and cell nuclei staining by confocal microscopy. White arrows indicate the clustering and dimerization of TREM-1 at the membrane of U937-vitD cells after incubation with LPS. FIG. 1C is a graph showing sTREM-1 concentration in the supernatant of U937 and U937-vitD cells after 30 minutes incubation in resting conditions or with APMA, Pro-MMP9, Act-MMP9 or LPS (100 ng/mL as indicated. LOQ: Limit of Quantification.

FIG. 7 is a scheme depicting the two stages of the phase IIa clinical trial assessing the administration of nangibotide (also known as motrem) to septic shock patients (NCT03158948).

FIG. 8 is a scheme depicting patient randomization in each treatment group.

FIG. 9A depicts nangibotide kinetics in each group (i.e., patients who received 0.3 mg/kg/h, patients who received 1.0 mg/kg/h and patients who received 3.0 mg/kg/h) from the start of the infusion (day 0) to the end of infusion (day 5) and FIG. 9B depicts nangibotide kinetics in each group (i.e., patients who received 0.3 mg/kg/h, patients who received 1.0 mg/kg/h and patients who received 3.0 mg/kg/h) after the end of the infusion. Circles: 0.3 mg/kg/h; squares: 1 mg/kg/h; triangles: 3 mg/kg/h.

FIG. 14A depicts the sTREM-1 change at day 5/EOI (end of infusion) from baseline in all population, in the subgroup G1 (patients with sTREM-1 baseline below the median) and in the subgroup G2 (patients with sTREM-1 baseline above the median). FIG. 14B depicts the association between delta SOFA at day 5 (delta between day 5/EOI and baseline).

DETAILED DESCRIPTION

Figure 1A:
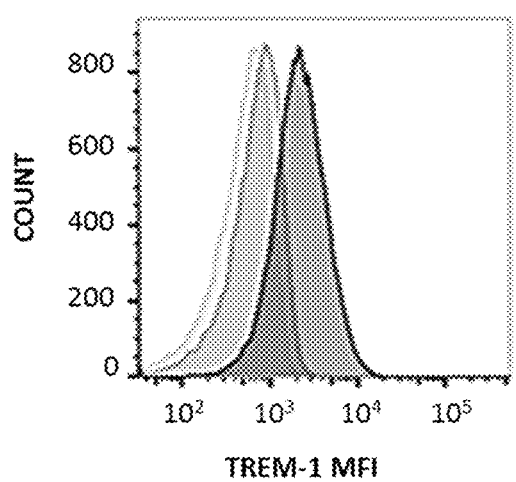
FIGS. 1A-1C show that sTREM-1 release depends on TREM-1 dimerization.

The present invention relates to an in vitro method for identifying a human subject suffering from an inflammatory disorder susceptible to respond to a therapy, said method comprising:

a) measuring the level of soluble triggering receptors expressed on myeloid cells-1 (sTREM-1) in a biological sample from the human subject;
b) comparing the level of sTREM-1 measured at step a) to a predetermined sTREM-1 value;
c) identifying a human subject suffering from an inflammatory disorder with a level of sTREM-1 measured at step a) higher than the predetermined sTREM-1 value of step b) as susceptible to respond to a therapy.

In other words, the present invention relates to an in vitro method for identifying a human subject suffering from an inflammatory disorder susceptible to respond to a therapy, wherein a level of soluble Triggering Receptors Expressed on Myeloid cells-1 (sTREM-1) measured in a biological sample from the human subject higher than a predetermined sTREM-1 value indicates that the human subject is susceptible to respond to a therapy.

The present invention also relates to an in vitro method for selecting a human subject suffering from an inflammatory disorder, for treatment with a therapy, preferably a TREM-1 inhibitor, said method comprising:
a) measuring the level of soluble triggering receptors expressed on myeloid cells-1 (sTREM-1) in a biological sample from the human subject;
b) comparing the level of sTREM-1 measured at step a) to a predetermined sTREM-1 value;
c) selecting a human subject suffering from an inflammatory disorder with a level of sTREM-1 measured at step a) higher than the predetermined sTREM-1 value of step b) for treatment with a therapy, preferably a TREM-1 inhibitor.

Another object of the invention is a therapy, preferably a TREM-1 inhibitor, for use in the treatment of an inflammatory disorder in a subject in need thereof, wherein a level of sTREM-1 measured in a biological sample from the subject and higher than a predetermined sTREM-1 value indicates that the subject is susceptible to respond to the therapy, preferably to the TREM-1 inhibitor.

Thus, the present invention also relates to a method for treating an inflammatory disorder in a human subject identified as susceptible to respond to a therapy, preferably to a TREM-1 inhibitor, said method comprising:
identifying a human subject suffering from an inflammatory disorder susceptible to respond to a therapy, preferably to a TREM-1 inhibitor by:
a) obtaining a biological sample from the human subject and measuring the level of soluble triggering receptors expressed on myeloid cells-1 (sTREM-1) in said biological sample;
b) comparing the level of sTREM-1 measured at step a) to a predetermined sTREM-1 value; and
c) identifying a human subject suffering from an inflammatory disorder with a level of sTREM-1 measured at step a) higher than the predetermined sTREM-1 value of step b) as susceptible to respond to a therapy, preferably to a TREM-1 inhibitor;
administering a therapy, preferably a TREM-1 inhibitor, to the subject suffering from an inflammatory disorder identified as susceptible to respond to a therapy, preferably to a TREM-1 inhibitor, thereby treating an inflammatory disorder in a human subject identified as susceptible to respond to a therapy, preferably to a TREM-1 inhibitor.

TREM-1 (triggering receptor expressed on myeloid cells-1) is a glycoprotein receptor belonging to the Ig superfamily that is expressed notably on myeloid cells. sTREM-1 is a soluble form of TREM-1 lacking the transmembrane and intracellular domains of TREM-1. Without wishing to be bound to a theory, the Applicant suggest that PRRs (Pathogen Recognition Receptors) engagement, including Nod-like receptors (NLRs) and Toll-like receptors (TLRs), induces the upregulation of TREM-1 expression and/or its mobilization and clustering at the cell membrane, which lead to its dimerization and multimerization. Said NLRs and TLRs activation can occur by linking DAMPs (Danger Associated Molecular Patterns) or PAMPs (Pathogen Associated Molecular Patterns). In particular said NLRs and TLRs activation can occur under sterile inflammatory conditions by linking DAMPs (Danger Associated Molecular Patterns) and/or alarmins, or under infectious conditions by linking PAMPs (Pathogen Associated Molecular Patterns). This activation of NLRs and TLRs induces the upregulation of proteases, in particular of metalloproteinases, which in turn, among a number of targets, will induce the liberation of a soluble TREM-1 through proteolytic cleavage of membrane-anchored TREM-1 (Gomez-Pina et al., J Immunol. 2007 Sep. 15; 179(6):4065-73). Said proteolytic cleavage depends on the dimerization of the TREM-1 receptor. sTREM-1 is thus shed from the membrane of myeloid cells, in particular from activated myeloid cells and sTREM-1 release is a marker of TREM-1 activation. In one embodiment, sTREM-1 corresponds to the soluble form of the extracellular domain of TREM-1. In one embodiment, sTREM-1 corresponds to a truncated TREM-1 shed from the membrane of myeloid cells, in particular from activated myeloid cells.

sTREM-1 may also results from an alternative splicing of TREM-1 mRNA. A TREM-1 splice variant was characterized in 2015 by Baruah et al., (J Immunol. 2015 Dec. 15; 195(12):5725-31) and was found to be secreted from primary and secondary human neutrophil granules. In one embodiment, sTREM-1 corresponds to a TREM-1 splice variant. In one embodiment, sTREM-1 corresponds to the TREM-1 transcript commonly referred to as TREM1-202, also known as TREM-1 isoform 2, encoding an amino acid sequence as set forth in SEQ ID NO: 2. In one embodiment, sTREM-1 thus has an amino acid sequence as set forth in SEQ ID NO: 2

(MRKTRLWGLLWMLFVSELRAATKLTEEKYELKEGQTLDVKCDYTLEKFA

SSQKAWQIIRDGEMPKTLACTERPSKNSHPVQVGRIILEDYHDHGLLRVR

MVNLQVEDSGLYQCVIYQPPKEPHMLFDRIRLVVTKGFRCSTLSFSWLVD

S).

In one embodiment, sTREM-1 has an amino acid sequence as set forth in SEQ ID NO: 5

(ATKLTEEKYELKEGQTLDVKCDYTLEKFASSQKAWQIIRDGEMPKTLAC

TERPSKNSHPVQVGRIILEDYHDHGLLRVRMVNLQVEDSGLYQCVIYQPP

KEPHMLFDRIRLVVTKGFSGTPGSNENSTQNVYKIPPTTTKALCPLYTSP

RTVTQAPPKSTADVSTPDSEINLTNVTDIIRVPVFN), corresponding to amino acids 21 to 205 of SEQ ID NO: 1.

In another embodiment, sTREM-1 has an amino acid sequence as set forth in SEQ ID NO: 6

(LKEGQTLDVKCDYTLEKFASSQKAWQIIRDGEMPKTLACTERPSKNSHP
VQVGRIILEDYHDHGLLRVRMVNLQVEDSGLYQCVIYQPPKEPHMLFDRI
RLVVTKGFSGTPGSNENSTQNVYKIPPTTTKALCPLYTSPRTVTQAPPKS
TADVSTPDSEINLTNVTDIIRVPVFN), corresponding to amino acids 31 to 205 of SEQ ID NO: 1.

In another embodiment, sTREM-1 comprises an amino sequence as set forth in SEQ ID NO: 19

(LKEGQTLDVKCDYTLEKFASSQKAWQIIRDGEMPKTLACTERPSKNSHP
VQVGRIILEDYHDHGLLRVRMVNLQVEDSGLYQCVIYQPPKEPHMLFDRI
RLVVTKGF), corresponding to amino acids 31 to 137 of SEQ ID NO: 1, and has a length of 200 amino acids or less, preferably of 185 amino acids or less.

In another embodiment, sTREM-1 has an amino acid sequence as set forth in SEQ ID NO: 2, SEQ ID NO: 5 or SEQ ID NO: 6. In another embodiment, sTREM-1 has an amino acid sequence as set forth in SEQ ID NO: 5 or in SEQ ID NO: 6.

In one embodiment, sTREM-1 is a variant of SEQ ID NO: 2, a variant of SEQ ID NO: 5 or a variant of SEQ ID NO: 6. In one embodiment, sTREM-1 is a variant of SEQ ID NO: 5 or a variant of SEQ ID NO: 6.

In one embodiment, a variant of SEQ ID NO: 2, SEQ ID NO: 5 or SEQ ID NO: 6 is an amino acid sequence comprising at least 25 contiguous amino acids, preferably at least 50, 60, 70, 80, 90, 100, 110, 120, 130, 140, 150, 160, 165, 170, 175, 180 or 185 contiguous amino acids of the amino acid sequence of SEQ ID NO: 2, SEQ ID NO: 5 or SEQ ID NO: 6, respectively.

In another embodiment, a variant of SEQ ID NO: 2, SEQ ID NO: 5 or SEQ ID NO: 6 is an amino acid sequence comprising the amino acid sequence of SEQ ID NO: 2, SEQ ID NO: 5 or SEQ ID NO: 6, respectively, and additional amino acids in C-term or in N-term of SEQ ID NO: 2, SEQ ID NO: 5 or SEQ ID NO: 6, wherein the number of additional amino acids ranges from 1 to 50, preferably from 1 to 20, more preferably from 1 to 10 amino acids, such as, for example, 1, 2, 3, 4, 5, 6, 7, 8, 9 or 10 amino acids in C-term and/or 1, 2, 3, 4, 5, 6, 7, 8, 9 or 10 amino acids in N-term.

In another embodiment, a variant of SEQ ID NO: 2, SEQ ID NO: 5 or SEQ ID NO: 6 is an amino acid sequence that typically differs from the amino acid sequence of SEQ ID NO: 2, SEQ ID NO: 5 or SEQ ID NO: 6 through one or more amino acid substitution(s), deletion(s), addition(s) and/or insertion(s). In one embodiment, said substitution(s), deletion(s), addition(s) and/or insertion(s) may affect 1, 2, 3, 4, 5, 6, 7, 8, 9, or 10 amino acids.

In another embodiment, a variant of SEQ ID NO: 2, SEQ ID NO: 5 or SEQ ID NO: 6 is an amino acid sequence of at least 25 amino acids, preferably of at least 50, 60, 70, 80, 90, 100, 110, 120, 130, 140, 150, 160, 165, 170, 175, 180 or 185 amino acids having at least 60%, 65%, 70%, 75%, 80%, 90%, 95%, or at least 96%, 97%, 98%, 99% or more identity with the amino acid sequence of SEQ ID NO: 2, SEQ ID NO: 5 or SEQ ID NO: 6, respectively.

The term "identity" or "identical", when used in a relationship between the sequences of two or more polypeptides, refers to the degree of sequence relatedness between polypeptides, as determined by the number of matches between strings of two or more amino acid residues. "Identity" measures the percent of identical matches between the smaller of two or more sequences with gap alignments (if any) addressed by a particular mathematical model or computer program (i.e., "algorithms"). Identity of related polypeptides can be readily calculated by known methods. Such methods include, but are not limited to, those described in Computational Molecular Biology, Lesk, A. M., ed., Oxford University Press, New York, 1988; Biocomputing: Informatics and Genome Projects, Smith, D. W., ed., Academic Press, New York, 1993; Computer Analysis of Sequence Data, Part 1, Griffin, A. M., and Griffin, H. G., eds., Humana Press, New Jersey, 1994; Sequence Analysis in Molecular Biology, von Heinje, G., Academic Press, 1987; Sequence Analysis Primer, Gribskov, M. and Devereux, J., eds., M. Stockton Press, New York, 1991; and Carillo et al., SIAM J. Applied Math. 48, 1073 (1988). Preferred methods for determining identity are designed to give the largest match between the sequences tested. Methods of determining identity are described in publicly available computer programs. Preferred computer program methods for determining identity between two sequences include the GCG program package, including GAP (Devereux et al., Nucl. Acid. Res. 2, 387 (1984); Genetics Computer Group, University of Wisconsin, Madison, Wis.), BLASTP, BLASTN, and FASTA (Altschul et al., J. Mol. Biol. 215, 403-410 (1990)). The BLASTX program is publicly available from the National Center for Biotechnology Information (NCBI) and other sources (BLAST Manual, Altschul et al. NCB/NLM/NIH Bethesda, Md. 20894; Altschul et al., supra). The well-known Smith Waterman algorithm may also be used to determine identity.

In one embodiment, the variant of SEQ ID NO: 2, SEQ ID NO: 5 or SEQ ID NO: 6 is not SEQ ID NO: 1.

In one embodiment, sTREM-1 is a fragment of SEQ ID NO: 2, a fragment of SEQ ID NO: 5 or a fragment of SEQ ID NO: 6. In one embodiment, sTREM-1 is a fragment of SEQ ID NO: 5 or a fragment of SEQ ID NO: 6.

In one embodiment, a fragment of SEQ ID NO: 2, SEQ ID NO: 5 or SEQ ID NO: 6 is an amino acid sequence comprising at least 25 contiguous amino acids, preferably of at least 50, 60, 70, 80, 90, 100, 110, 120, 130, 140, 150, 160, 165, 170, 175, 180 or 185 contiguous amino acids of the amino acid sequence of SEQ ID NO: 2, SEQ ID NO: 5 or SEQ ID NO: 6, respectively.

In one embodiment, sTREM-1 corresponds to the extracellular fragment generated by cleavage of the membrane-bound TREM-1 having an amino acid sequence as set forth in SEQ ID NO: 1 by a protease, preferably a matrix metallopeptidase, more preferably by the matrix metalloproteinase 9 (MMP9).

As used herein, "biological sample" refers to a biological sample isolated from a human subject and can include, by way of example and not limitation, bodily fluids, cell samples and/or tissue extracts such as homogenates or solubilized tissue obtained from a human subject.

In one embodiment, the method of the invention does not comprise obtaining a biological sample from a subject. In one embodiment, the biological sample from the human subject is a biological sample previously obtained from the human subject. Said biological sample may be conserved in adequate conditions before being used in the method of the invention.

In one embodiment, the biological sample from the human subject is a body fluid sample. Examples of body fluids include, without being limited to, blood, plasma, serum, lymph, urine, bronchioalveolar lavage fluid, cerebrospinal fluid, sweat or any other bodily secretion or derivative thereof.

As used herein, "blood" includes whole blood, plasma, serum, circulating epithelial cells, constituents, or any other derivative of blood.

In one embodiment, the biological sample from the human subject is a blood sample. In one embodiment, the biological sample from the human subject is a whole blood sample or a plasma sample. Methods for obtaining a plasma sample are routinely used in clinical laboratories. In one embodiment, the whole blood sample or the plasma sample from the human subject is processed to obtain a serum sample. Methods for obtaining a serum sample from a whole blood sample or a plasma sample are routinely used in clinical laboratories.

In another embodiment, the biological sample from the human subject is a tissue extract. Tissue extracts are obtained routinely from tissue biopsy and autopsy material.

According to the present invention, the term "level" as used herein refers to the expression level of sTREM-1. It can refer alternatively to the transcription level of sTREM-1 or to the translation level of sTREM-1. The expression level may be detected intracellularly or extracellularly.

The level of TREM-1 may be measured with a point-of-care testing (POCT) or bedside testing; with a near-to-patient testing; or with a central laboratory assay.

Methods for measuring the expression level such as a transcription level or a translation level are well-known to the skilled artisan and include, but are not limited to, RT-PCR, RT-qPCR, Northern Blot, hybridization techniques such as, for example, use of microarrays, and combination thereof including but not limited to, hybridization of amplicons obtained by RT-PCR, sequencing such as, for example, next-generation DNA sequencing (NGS) or RNA-seq (also known as "Whole Transcriptome Shotgun Sequencing") and the like, immunohistochemistry, Multiplex methods (such as Luminex), western blot, enzyme-linked immunosorbent assay (ELISA), sandwich ELISA, multiplex ELISA, electrochemiluminescence (ECL) also referred as electrochemiluminescence immunoassay (ECLIA) (such as Elecsys®, Roche Diagnostics), enzyme-linked fluorescent assay (ELFA) (such as VIDAS®, Biomerieux), fluorescent-linked immunosorbent assay (FLISA), enzyme immunoassay (EIA), radioimmunoassay (RIA), flow cytometry (FACS), surface plasmon resonance (SPR), biolayer interferometry (BLI), immunochromatographic assay (ICA) (such as NEXUS IB10, Sphingotech) and mass spectrometry-based approaches.

According to one embodiment, the term "level" as used herein refers to the quantity, amount or concentration of sTREM-1. Thus, the level of sTREM-1 measured in a biological sample from a human subject refers to the quantity, amount or concentration of sTREM-1 in said biological sample.

According to one embodiment, the level of sTREM-1 refers to a protein level, a protein quantity, a protein amount or a protein concentration.

In one embodiment, the level of sTREM-1 refers to the level of the amino acid sequences as set forth in SEQ ID NO: 2, SEQ ID NO: 5 and/or SEQ ID NO: 6, and/or fragments and/or variants thereof as described hereinabove. In one embodiment, the level of sTREM-1 refers to the level of the amino acid sequences as set forth in SEQ ID NO: 5 and/or SEQ ID NO: 6, and/or fragments and/or variants thereof as described hereinabove.

In one embodiment, the biological sample from a human subject is a blood sample and the level of sTREM-1 measured in said biological sample corresponds to the blood concentration of sTREM-1 of said human subject.

In one embodiment, the biological sample from a human subject is a plasma sample and the level of sTREM-1 measured in said biological sample corresponds to the plasma concentration of sTREM-1 of said human subject.

In one embodiment, the biological sample from a human subject is a serum sample and the level of sTREM-1 measured in said biological sample corresponds to the serum concentration of sTREM-1 of said human subject.

According to the invention, the level of sTREM-1 may be measured by any known method in the art.

Methods for measuring the level of sTREM-1, in particular a sTREM-1 protein level, in a biological sample as described hereinabove are well-known to the skilled artisan and include, without being limited to, immunohistochemistry, Multiplex methods (such as Luminex), western blot, enzyme-linked immunosorbent assay (ELISA), sandwich ELISA, multiplex ELISA, electrochemiluminescence immunoassay (ECLIA) (such as Elecsys®, Roche Diagnostics), enzyme-linked fluorescent assay (ELFA) (such as VIDAS®, Biomerieux), fluorescent-linked immunosorbent assay (FLISA), enzyme immunoassay (EIA), radioimmunoassay (RIA), flow cytometry (FACS) surface plasmon resonance (SPR), biolayer interferometry (BLI), immunochromatographic assay (ICA) (such as NEXUS IB10, Sphingotech) and mass spectrometry-based approaches.

Typically, measuring the level of sTREM-1 in a biological sample as described hereinabove may comprise contacting the biological sample with a binding partner capable of selectively interacting with sTREM-1 in the biological sample. In one embodiment, the binding partner is an antibody, such as, for example, a monoclonal antibody or an aptamer.

In one embodiment, measuring the level of sTREM-1 in a biological sample as described hereinabove comprises the use of an antibody, such as a polyclonal or monoclonal antibody.

Examples of antibodies allowing the detection of sTREM-1 include, without being limited to, the polyclonal antibody raised against Met1-Arg200 amino acids of human TREM-1 (reference AF1278 from R&D Systems), the monoclonal antibody raised against Ala21-Asn205 of human TREM-1 (reference MAB1278 from R&D Systems), the purified anti-human CD354 (TREM-1) antibody (clone TREM-26, reference 314902 from BioLegend), the purified anti-human CD354 (TREM-1) antibody (clone TREM-37, reference 316102 from BioLegend), the monoclonal mouse anti-human sTREM1 (clone 15G7, reference 298099 from USBio), the mouse anti-human TREM1 (clone 2E2, reference 134704 from USBio). Other non-limitative examples of antibodies allowing the detection of sTREM-1 include sTREM-1 and/or TREM-1 antibodies described in the following patents or patent applications: US2013/150559, US 2013/211050, US 2013/309239, WO2013/120553 and U.S. Pat. No. 8,106,165.

Some of the aforementioned assays for measuring the level of sTREM-1 in a biological sample (such as, for example, western blot, ELISA, or sandwich ELISA) generally involve the binding of the partner (i.e., an antibody or an aptamer) to a solid support. Solid supports which can be used in the practice of the method of the invention include, without being limited to, supports such as nitrocellulose (e.g., nitrocellulose membranes or nitrocellulose microtiter plates); polyvinylchloride (e.g., polyvinylchloride sheets, polyvinylchloride membranes or polyvinylchloride microtiter plates); polystyrene latex (e.g., polystyrene latex beads or polystyrene latex microtiter plates); polyvinylidene difluoride or PVDF (e.g., PVDF membranes); diazotized paper; nylon membranes; activated beads, and magnetically responsive beads.

The level of sTREM-1 may be measured by using standard immunodiagnostic techniques, including immunoassays such as competition, direct reaction, or sandwich type assays. Such assays include, but are not limited to, agglutination tests; enzyme-labelled and mediated immunoassays, such as ELISAs; biotin/avidin type assays; radioimmunoassays; immuno-electrophoresis; immuno-precipitation. Immunoassays thus include, without being limited to, enzyme-labelled and mediated immunoassays, such as ELISAs or enzyme-linked fluorescent assays (ELFA); biotin/avidin type assays; radioimmunoassays; immuno-electrophoresis; immuno-precipitation; electrochemiluminescence immunoassay (ECLIA).

An exemplary biochemical test for identifying specific proteins employs a standardized test format, such as ELISA test, although the information provided herein may apply to the development of other biochemical tests and is not limited to the development of an ELISA test (see for example Molecular Immunology: A Textbook, edited by Atassi et al. Marcel Dekker Inc., New York and Basel 1984, for a description of ELISA tests). It is understood that commercial assay enzyme-linked immunosorbent assay (ELISA) kits for various plasma constituents are available.

Therefore, the ELISA method may be used for measuring the level of sTREM-1 in a biological sample, wherein the wells of a microtiter plate are coated with at least one antibody which recognizes sTREM-1. A biological sample containing or suspected of containing sTREM-1 is then added to the coated wells. After a period of incubation sufficient to allow the formation of antibody-sTREM-1 complexes, the plate(s) can be washed to remove unbound moieties and a detectably labelled secondary binding molecule added. The secondary binding molecule is allowed to react with any captured antibody-sTREM-1 complexes, the plate washed and the presence of the secondary binding molecule detected using methods well-known in the art.

In one embodiment, measuring the level of sTREM-1 in a biological sample as described hereinabove comprises the use of an enzyme-linked immunosorbent assay (ELISA), an electrochemiluminescence immunoassay (ECLIA) (such as Elecsys® Roche Diagnostics) or an enzyme-linked fluorescent assay (ELFA).

Examples of ELISA assays include, without being limited to, the TREM-1 Quantikine ELISA kit (reference DTRM10C from R&D Systems); the human TREM-1 DuoSet (references DY1278B and DY1278BE from R&D Systems), the sTREM-1 ELISA (reference sTREM-1 ELISA from iQProducts).

Examples of electrochemiluminescence immunoassays (ECLIAs) include Elecsys® (Roche Diagnostics).

Examples of enzyme-linked fluorescent assays (ELFAs) include VIDAS® (Biomerieux).

Typically, the level of sTREM-1 in a biological sample may be measured by an immunometric assay on the basis of a double-antibody "sandwich" technique, with a monoclonal antibody specific for sTREM-1. Thus, in one embodiment, measuring the level of sTREM-1 in a biological sample as described hereinabove comprises the use sandwich ELISA.

According to one embodiment, measuring the level of sTREM-1 (with or without immunoassay-based methods) may also include separation of the compounds present in the biological sample (i.e., separation of sTREM-1): centrifugation based on the compound's molecular weight; electrophoresis based on mass and charge; HPLC based on hydrophobicity; size exclusion chromatography based on size; and solid-phase affinity based on the compound's affinity for the particular solid-phase that is used.

Once separated, said compounds (i.e., sTREM-1) may be identified based on the known "separation profile", e.g., retention time, for that compound and measured using standard techniques. Alternatively, the separated compounds (i.e., sTREM-1) may be detected and measured by, for example, a mass spectrometer.

According to one embodiment, the level of sTREM-1 refers to a nucleic acid level, a nucleic acid quantity, a nucleic acid amount or a nucleic acid concentration. In one embodiment, the nucleic acid is an RNA, preferably an mRNA, or a cDNA.

Methods for measuring the expression level, in particular a sTREM-1 nucleic acid level, in a biological sample as described hereinabove are well-known to the skilled artisan and include, without being limited to, PCR, qPCR, RT-PCR, RT-qPCR, Northern Blot, hybridization techniques such as, for example, use of microarrays, and combination thereof including but not limited to, hybridization of amplicons obtained by RT-PCR, sequencing such as, for example, next-generation DNA sequencing (NGS) or RNA-seq (also known as "Whole Transcriptome Shotgun Sequencing").

In one embodiment, the sTREM-1 nucleic acid level is measured using the forward and reverse primers having a nucleotide sequence has set forth in SEQ ID NO: 13 (GTGGTGACCAAGGGGTTC) and SEQ ID NO: 14 (AGATGGATGTGGCTG GAAGT), respectively.

In one embodiment, the sTREM-1 nucleic acid level is measured using the forward and reverse primers having a nucleotide sequence has set forth in SEQ ID NO: 15 (GTGACCAAGGGTrTTCAGG) and SEQ ID NO: 16 (ACACCGGAACCCTGAT GATA), respectively.

In one embodiment, the sTREM-1 nucleic acid level is measured using the forward and reverse primers having a nucleotide sequence has set forth in SEQ ID NO: 17 (AAAGGCAAGAACGCCTGAC) and SEQ ID NO: 18 (GGGACTTTACCAAGAGG GAC), respectively In one embodiment, the level of sTREM-1 measured in a biological sample as described hereinabove is a baseline level. In other words, the level of sTREM-1 is measured in a biological sample as described hereinabove obtained from the human subject suffering from an inflammatory disorder before the beginning of an administration of a therapy, preferably of a TREM-1 inhibitor.

In one embodiment, the level of sTREM-1 is measured in a biological sample as described hereinabove obtained from the human subject between the first 2 hours and the first 48 hours, preferably between the first 2 hours and the first 12 hours, between the first 12 hours and the first 24 hours or between the first 24 hours and the first 48 hours, following the onset of an inflammatory disorder, preferably SIRS, sepsis or septic shock; following the diagnosis of the human subject with an inflammatory disorder, preferably SIRS, sepsis or septic shock; following the hospitalization, in particular the admission in ICU or emergency unit, of the human subject for an inflammatory disorder, preferably SIRS, sepsis or septic shock; or following the start of vasopressor therapy.

In one embodiment, the level of sTREM-1 is measured in a biological sample as described hereinabove obtained from the human subject within the first 2, 3, 6, 9, 12, 15, 18, 21, 24, 30, 36, 42 or 48 hours following the onset of an inflammatory disorder, preferably SIRS, sepsis or septic shock; following the diagnosis of the human subject with an inflammatory disorder, preferably SIRS, sepsis or septic shock; following the hospitalization, in particular the admission in ICU or emergency unit, of the human subject for an inflammatory disorder, preferably SIRS, sepsis or septic shock; or following the start of vasopressor therapy.

In one embodiment, the level of sTREM-1 is measured in a biological sample as described hereinabove between the first 2 hours and the first 48 hours, preferably between the first 2 hours and the first 12 hours, between the first 12 hours and the first 24 hours or between the first 24 hours and the first 48 hours, following the onset of an inflammatory disorder, preferably SIRS, sepsis or septic shock; following the diagnosis of the human subject with an inflammatory disorder, preferably SIRS, sepsis or septic shock; following the hospitalization, in particular the admission in ICU or emergency unit, of the human subject for an inflammatory disorder, preferably SIRS, sepsis or septic shock; or following the start of vasopressor therapy.

In one embodiment, the level of sTREM-1 is measured in a biological sample as described hereinabove within the first 2, 3, 6, 9, 12, 15, 18, 21, 24, 30, 36, 42 or 48 hours following the onset of an inflammatory disorder, preferably SIRS, sepsis or septic shock; following the diagnosis of the human subject with an inflammatory disorder, preferably SIRS, sepsis or septic shock; following the hospitalization, in particular the admission in ICU or emergency unit, of the human subject for an inflammatory disorder, preferably SIRS, sepsis or septic shock; or following the start of vasopressor therapy.

In one embodiment, the level of sTREM-1 is measured in a biological sample as described hereinabove obtained from the human subject between the first 2 hours and the first 48 hours, preferably between the first 2 hours and the first 12 hours, between the first 12 hours and the first 24 hours or between the first 24 hours and the first 48 hours, following a reinfection of the human subject suffering from an inflammatory disorder, preferably SIRS, sepsis or septic shock.

In one embodiment, the level of sTREM-1 is measured in a biological sample as described hereinabove obtained from the human subject within the first 2, 3, 6, 9, 12, 15, 18, 21, 24, 30, 36, 42 or 48 hours following a reinfection of the human subject suffering from an inflammatory disorder, preferably SIRS, sepsis or septic shock.

In one embodiment, the level of sTREM-1 is measured in a biological sample as described hereinabove between the first 2 hours and the first 48 hours, preferably between the first 2 hours and the first 12 hours, between the first 12 hours and the first 24 hours or between the first 24 hours and the first 48 hours, following a reinfection of the human subject suffering from an inflammatory disorder, preferably SIRS, sepsis or septic shock.

In one embodiment, the level of sTREM-1 is measured in a biological sample as described hereinabove within the first 2, 3, 6, 9, 12, 15, 18, 21, 24, 30, 36, 42 or 48 hours following a reinfection of the human subject suffering from an inflammatory disorder, preferably SIRS, sepsis or septic shock.

In one embodiment, the level of sTREM-1 is measured in a biological sample as described hereinabove obtained from the human subject between the first 2 hours and the first 48 hours, preferably between the first 2 hours and the first 12 hours, between the first 12 hours and the first 24 hours or between the first 24 hours and the first 48 hours, following a rehospitalization, in particular a readmission to ICU or emergency unit, of the human subject suffering from an inflammatory disorder, preferably SIRS, sepsis or septic shock.

In one embodiment, the level of sTREM-1 is measured in a biological sample as described hereinabove obtained from the human subject within the first 2, 3, 6, 9, 12, 15, 18, 21, 24, 30, 36, 42 or 48 hours following a rehospitalization, in particular a readmission to ICU or emergency unit, of the human subject suffering from an inflammatory disorder, preferably SIRS, sepsis or septic shock.

In one embodiment, the level of sTREM-1 is measured in a biological sample as described hereinabove between the first 2 hours and the first 48 hours, preferably between the first 2 hours and the first 12 hours, between the first 12 hours and the first 24 hours or between the first 24 hours and the first 48 hours, following a rehospitalization, in particular a readmission to ICU or emergency unit, of the human subject suffering from an inflammatory disorder, preferably SIRS, sepsis or septic shock.

In one embodiment, the level of sTREM-1 is measured in a biological sample as described hereinabove within the first 2, 3, 6, 9, 12, 15, 18, 21, 24, 30, 36, 42 or 48 hours following a rehospitalization, in particular a readmission to ICU or emergency unit, of the human subject suffering from an inflammatory disorder, preferably SIRS, sepsis or septic shock.

In one embodiment, the level of sTREM-1 is measured in a biological sample as described hereinabove obtained from the human subject between the first 2 hours and the first 48 hours, preferably between the first 2 hours and the first 12 hours, between the first 12 hours and the first 24 hours or between the first 24 hours and the first 48 hours following the onset of septic shock; following the diagnosis of the human subject for septic shock; following the hospitalization, in particular the admission to ICU or emergency unit, of the human subject for septic shock; or following the start of vasopressor therapy.

In one embodiment, the level of sTREM-1 is measured in a biological sample as described hereinabove obtained from the human subject within the first 2, 3, 6, 9, 12, 15, 18, 21, 24, 30, 36, 42 or 48 hours following the onset of septic shock; following the diagnosis of the human subject for septic shock; following the hospitalization, in particular the admission to ICU or emergency unit, of the human subject for septic shock; or following the start of vasopressor therapy.

In one embodiment, the level of sTREM-1 is measured in a biological sample as described hereinabove between the first 2 hours and the first 12 hours, the first 12 hours and the first 24 hours or between the first 24 hours and the first 48 hours following the onset of septic shock; following the diagnosis of the human subject for septic shock; following the hospitalization, in particular the admission to ICU or emergency unit, of the human subject for septic shock; or following the start of vasopressor therapy.

In one embodiment, the level of sTREM-1 is measured in a biological sample as described hereinabove within the first 2, 3, 6, 9, 12, 15, 18, 21, 24, 30, 36, 42 or 48 hours following the onset of septic shock; following the diagnosis of the human subject for septic shock; following the hospitalization, in particular the admission to ICU or emergency unit, of the human subject for septic shock; or following the start of vasopressor therapy.

In one embodiment, the predetermined sTREM-1 value is a personalized reference value, i.e., the predetermined sTREM-1 value is obtained using a biological sample obtained from the human subject.

In one embodiment, the predetermined value of sTREM-1 is an index value or is derived from one or more risk prediction algorithms or computed indices for an inflammatory disorder, preferably SIRS, sepsis or septic shock.

In one embodiment, the predetermined value of sTREM-1 is obtained from a reference population.

According to the present invention, the predetermined sTREM-1 value can be derived from population studies, including, for example, subjects having a similar age range, subjects in the same or similar ethnic group, subjects having a chronic medical condition linked with an increased risk of an inflammatory disorder, preferably SIRS, sepsis or septic shock (such as atrial fibrillation, cancer, chronic kidney disease, chronic lung disease, cirrhosis, coronary artery disease, deep vein thrombosis, diabetes, dyslipidemia, endocarditis, hypertension, influenza, malaria or any other protozoan parasitic disease, myocardial infarction, neurological disease, non-alcoholic fatty liver disease (NAFLD), non-alcoholic steatohepatitis (NASH), peripheral artery disease, pulmonary fibrosis, severe obesity and stroke) or subjects with a history of an inflammatory disorder such as SIRS, sepsis or septic shock.

According to one embodiment, the predetermined value of sTREM-1 is derived from the measure of the sTREM-1 level in a biological sample from one or more human subjects who are substantially healthy. As used herein, a "substantially healthy subject" is a human subject who has not been previously diagnosed or identified as having or suffering from an inflammatory disorder, preferably SIRS, sepsis or septic shock. Thus, according to one embodiment, the predetermined sTREM-1 value is obtained from a reference population of human subjects who are substantially healthy.

In one embodiment, a "substantially healthy subject" is a human subject who does not suffer from an infection.

According to one embodiment, the predetermined value of sTREM-1 obtained from a reference population of human subjects who are substantially healthy is a sTREM-1 level, preferably a blood, plasma or serum level, ranging from about 50 pg/mL to about 250 pg/mL.

In one embodiment, the predetermined value of sTREM-1 obtained from a reference population of human subjects who are substantially healthy is a sTREM-1 level, preferably a blood, plasma or serum level, of about 50, 75, 100, 125, 150, 175, 200, 225 or 250 pg/mL.

In one embodiment, the predetermined value of sTREM-1 obtained from a reference population of human subjects who are substantially healthy is a sTREM-1 level, preferably a blood, plasma or serum level, ranging from about 50 pg/mL to about 150 pg/mL, in particular as determined using an enzyme-linked immunosorbent assay (ELISA).

In one embodiment, the predetermined value of sTREM-1 obtained from a reference population of human subjects who are substantially healthy is a sTREM-1 level, preferably a blood, plasma or serum level, of about 50, 75, 100, 125 or 150 pg/mL, in particular as determined using an enzyme-linked immunosorbent assay (ELISA).

In one embodiment, the predetermined value of sTREM-1 obtained from a reference population of human subjects who are substantially healthy is a sTREM-1 level, preferably a blood, plasma or serum level, ranging from about 150 pg/mL to about 250 pg/mL, in particular as determined using an electrochemiluminescence immunoassay (ECLIA).

In one embodiment, the predetermined value of sTREM-1 obtained from a reference population of human subjects who are substantially healthy is a sTREM-1 level, preferably a blood, plasma or serum level, of about 150, 175, 200, 225 or 250 pg/mL, in particular as determined using an electrochemiluminescence immunoassay (ECLIA).

According to another embodiment, the predetermined value of sTREM-1 is derived from the measure of the sTREM-1 level in a biological sample from one or more human subjects diagnosed or identified as suffering, or having suffered, from an inflammatory disorder, preferably SIRS, sepsis or septic shock. Thus, according to one embodiment, the predetermined sTREM-1 value is obtained from a reference population of human subjects diagnosed or identified as suffering, or having suffered, from an inflammatory disorder, preferably SIRS, sepsis or septic shock.

In one embodiment, the predetermined value of sTREM-1 is derived from the measure of the sTREM-1 level in a biological sample from one or more human subjects diagnosed or identified as suffering from sepsis. Thus, in one embodiment, the predetermined sTREM-1 value is obtained from a reference population of human subjects diagnosed or identified as suffering from sepsis.

In one embodiment, the in vitro method of the invention is for identifying a human subject suffering from sepsis susceptible to respond to an administration of a therapy, in particular of a TREM-1 inhibitor, and the predetermined value of sTREM-1 is derived from the measure of the sTREM-1 level in a biological sample from one or more human subjects diagnosed or identified as suffering from sepsis. In other words, in one embodiment, the in vitro method of the invention is for identifying a human subject suffering from sepsis susceptible to respond to an administration of a therapy, in particular of a TREM-1 inhibitor, and the predetermined sTREM-1 value is obtained from a reference population of human subjects diagnosed or identified as suffering from sepsis.

In one embodiment, the predetermined value of sTREM-1 is derived from the measure of the sTREM-1 level in a biological sample from one or more human subjects diagnosed or identified as suffering from septic shock. Thus, in one embodiment, the predetermined sTREM-1 value is obtained from a reference population of human subjects diagnosed or identified as suffering from septic shock.

In one embodiment, the in vitro method of the invention is for identifying a human subject suffering from septic shock susceptible to respond to an administration of a therapy, in particular of a TREM-1 inhibitor, and the predetermined value of sTREM-1 is derived from the measure of the sTREM-1 level in a biological sample from one or more human subjects diagnosed or identified as suffering from septic shock. In other words, in one embodiment, the in vitro method of the invention is for identifying a human subject suffering from septic shock susceptible to respond to an administration of a therapy, in particular of a TREM-1 inhibitor, and the predetermined sTREM-1 value is obtained from a reference population of human subjects diagnosed or identified as suffering from septic shock.

In one embodiment, the predetermined value of sTREM-1 is derived from the measure of the sTREM-1 level in a biological sample from one or more human subjects who have previously been diagnosed or identified as suffering from an inflammatory disorder, preferably SIRS, sepsis or septic shock.

In one embodiment, the predetermined value of sTREM-1 is derived from the measure of the sTREM-1 level in a biological sample from one or more human subjects suffering from an infection who are at high risk of developing an inflammatory disorder, preferably SIRS, sepsis or septic shock.

According to the present invention, the predetermined sTREM-1 value can be derived from statistical analyses and/or risk prediction data of a reference population as described hereinabove obtained from mathematical algorithms and computed indices of an inflammatory disorder, preferably SIRS, sepsis or septic shock.

According to one embodiment, the predetermined value of sTREM-1 is obtained from a reference population as described hereinabove using a method of statistical and/or structural classification.

According to one embodiment, the predetermined sTREM-1 value, preferably the predetermined sTREM-1 value obtained from a reference population as described hereinabove, is a sTREM-1 level, preferably a blood, plasma or serum level.

In one embodiment, a human subject suffering from an inflammatory disorder susceptible to respond to a therapy is a human subject with a level of sTREM-1 measured as described hereinabove higher than at least 1.5 times, 2 times, 2.5 times, 3 times, 3.5 times, 4 times, 4.5 times, 5 times, 5.5 times, 6 times, 6.5 times, 7 times, 7.5 times, 8 times, 8.5 times, 9 times, 9.5 times or 10 times the predetermined sTREM-1, preferably the predetermined sTREM-1 obtained from a reference population of human subjects who are substantially healthy, as described hereinabove.

In one embodiment, a human subject suffering from an inflammatory disorder susceptible to respond to a therapy is a human subject with a level of sTREM-1 measured as described hereinabove higher than at least 1.6 times, 1.8 times, 2 times, 2.2 times, 2.4 times, 2.6 times, 2.8 times, 3 times, 3.2 times, 3.4 times, 3.6 times, 3.8 times, 4 times, 4.2 times, 4.4 times, 4.6 times, 4.8 times, 5 times, 5.2 times, 5.4 times, 5.6 times, 5.8 times or 6 times the predetermined sTREM-1, preferably the predetermined sTREM-1 obtained from a reference population of human subjects who are substantially healthy, as described hereinabove.

In one embodiment, a human subject suffering from an inflammatory disorder susceptible to respond to a therapy is a human subject with a level of sTREM-1 measured as described hereinabove higher than at least 2 times, 2.1 times, 2.2 times, 2.3 times, 2.4 times, 2.5 times, 2.6 times, 2.7 times, 2.8 times, 2.9 times, 3 times, 3.1 times, 3.2 times, 3.3 times, 3.4 times, 3.5 times, 3.6 times, 3.7 times, 3.8 times, 3.9 times or 4 times the predetermined sTREM-1, preferably the predetermined sTREM-1 obtained from a reference population of human subjects who are substantially healthy, as described hereinabove.

In another embodiment, a human subject suffering from an inflammatory disorder susceptible to respond to a therapy is a human subject with a level of sTREM-1 measured as described hereinabove higher than at least 1.1 times, 1.2 times, 1.3 times, 1.4 times, 1.5 times, 1.6 times, 1.7 times, 1.8 times, 1.9 times, 2 times, 2.1 times, 2.2 times, 2.3 times, 2.4 times or 2.5 times the predetermined sTREM-1, preferably the predetermined sTREM-1 obtained from a reference population of human subjects diagnosed or identified as suffering, or having suffered, from an inflammatory disorder, preferably SIRS, sepsis or septic shock.

In one embodiment, the predetermined sTREM-1 value obtained from a reference population as described hereinabove, is the average sTREM-1 level, preferably the average blood, plasma or serum level, of said reference population. In another embodiment, the predetermined sTREM-1 value obtained from a reference population as described hereinabove, is the median sTREM-1 level, preferably the average blood, plasma or serum level, of said reference population.

According to one embodiment, the predetermined sTREM-1 value is obtained from a reference population as described hereinabove, wherein the sTREM-1 levels measured in a biological sample from each of the human subjects of the reference population (i.e., the sTREM-1 levels measured in the reference population) are divided into equal-sized groups by cut-off values referred to as "quantiles", each group corresponding to a determined percentage of the sTREM-1 levels measured in the reference population. Examples of quantiles include, without being limited to, the median (defining 2 groups each comprising 50% of the sTREM-1 levels measured in the reference population), the terciles or tertiles (defining 3 groups each comprising a third of the sTREM-1 levels measured in the reference population), the quartiles (defining 4 groups each comprising 25% of the sTREM-1 levels measured in the reference population), the quintiles (defining 5 groups each comprising 20% of the sTREM-1 levels measured in the reference population) and the deciles (defining 10 groups each comprising 10% of the sTREM-1 levels measured in the reference population).

According to the present invention, "quantiles" refer to the cut-off sTREM-1 values below or above which lies a determined percentage of the sTREM-1 levels measured in the reference population. Therefore, the human subjects with a measured sTREM-1 level below the first quantile are the human subjects with the lowest sTREM-1 levels, while the human subjects with a measured sTREM-1 level above the last quantile are the human subjects with the highest sTREM-1 levels. For example, the 1' decile is the sTREM-1 value below which 10% of the sTREM-1 levels measured in the reference population lie and above which 90% of the sTREM-1 levels measured in the reference population lie.

Additionally, the term "quantiles" may also sometimes refer to the group so defined by said cut-off value. Thus, applied to the present invention, the term "quantiles" may also refer to the groups of sTREM-1 levels measured in the reference population defined by the cut-off sTREM-1 value. For example, the $1^{st}$ decile may refer to the group of sTREM-1 levels measured in the reference population corresponding to the lowest 10% of sTREM-1 levels measured in the reference population. Accordingly, the $10^{th}$ decile refers to the group of sTREM-1 levels measured in the reference population corresponding to the highest 10% of sTREM-1 levels measured in the reference population. It follows that a sTREM-1 value that is in the 1' decile is a sTREM-1 value comprised in the lowest 10% of sTREM-1 levels measured in the reference population and that a sTREM-1 value that is in the $10^{th}$ decile is a sTREM-1 value comprised in the highest 10% of sTREM-1 levels measured in the reference population.

In one embodiment, the predetermined sTREM-1 value is obtained from a reference population as described hereinabove, wherein the sTREM-1 levels measured in the reference population are divided into two equal-sized groups each corresponding to 50% of the sTREM-1 levels measured in the reference population.

According to this embodiment of the present invention the sTREM-1 median corresponds to the sTREM-1 value below which 50% of the sTREM-1 levels measured in the reference population lie and above which 50% of the sTREM-1 levels measured in the reference population lie.

Thus, in one embodiment, the predetermined sTREM-1 value is the sTREM-1 median of a reference population as described hereinabove.

Accordingly, in one embodiment, the present invention relates to an in vitro method for identifying a human subject suffering from an inflammatory disorder, preferably SIRS, sepsis or septic shock, susceptible to respond to an administration of a therapy, in particular of a TREM-1 inhibitor, said method comprising:

a) measuring the level of soluble Triggering Receptors Expressed on Myeloid cells-1 (sTREM-1) in a biological sample from the human subject;
b) comparing the level of sTREM-1 measured at step a) to a predetermined sTREM-1 value obtained from a reference population sTREM-1, said predetermined sTREM-1 value being the median of said reference population;
c) identifying a human subject suffering from an inflammatory disorder, preferably SIRS, sepsis or septic shock with a level of sTREM-1 measured at step a) higher than the median of step b) as susceptible to respond to an administration of a therapy, in particular of a TREM-1 inhibitor.

In one embodiment, the predetermined sTREM-1 value is obtained from a reference population as described hereinabove, wherein the sTREM-1 levels measured in the reference population are divided into three equal-sized groups each corresponding to a third of the sTREM-1 levels measured in the reference population. As mentioned above, the cut-off values ("quantiles") so dividing the sTREM-1 levels measured in the reference population are called "terciles" (or "tertiles"). Thus, in one embodiment, the predetermined sTREM-1 value is a sTREM-1 tercile (or tertile) of a reference population as described hereinabove.

According to this embodiment of the present invention:
the sTREM-1 first tercile (or tertile) corresponds to the sTREM-1 value below which a third of the sTREM-1 levels measured in the reference population lie and above which two thirds of the sTREM-1 levels measured in the reference population lie; and
the sTREM-1 second tercile (or tertile) corresponds to the sTREM-1 value below which two thirds of the sTREM-1 levels measured in the reference population lie and above which one third of the sTREM-1 levels measured in the reference population lie.

In one embodiment, the predetermined sTREM-1 value is the second sTREM-1 tercile (i.e., the last sTREM-1 tercile) of a reference population as described hereinabove.

In one embodiment, the predetermined sTREM-1 value is obtained from a reference population as described hereinabove, wherein the sTREM-1 levels measured in the reference population are divided into four equal-sized groups each corresponding 25% of the sTREM-1 levels measured in the reference population. As mentioned above, the cut-off values ("quantiles") so dividing the sTREM-1 levels measured in the reference population are called "quartiles". Thus, in one embodiment, the predetermined sTREM-1 value is a sTREM-1 quartile of a reference population as described hereinabove.

According to this embodiment of the present invention:
the sTREM-1 first quartile (or Q1) corresponds to the sTREM-1 value below which 25% of the sTREM-1 levels measured in the reference population lie and above which 75% of the sTREM-1 levels measured in the reference population lie;
the sTREM-1 second quartile corresponds to the sTREM-1 value below which 50% of the sTREM-1 levels measured in the reference population lie and above which 50% of the sTREM-1 levels measured in the reference population lie (the second quartile is thus equivalent to the median);
the sTREM-1 third quartile (or Q3) corresponds to the sTREM-1 value below which 75% of the sTREM-1 levels measured in the reference population lie and above which 25% of the sTREM-1 levels measured in the reference population lie.

In one embodiment, the predetermined sTREM-1 value is the first sTREM-1 quartile also referred to as sTREM-1 Q1 of a reference population as described hereinabove.

In one embodiment, the predetermined sTREM-1 value is the third sTREM-1 quartile also referred to as sTREM-1 Q3 (i.e., the last sTREM-1 quartile) of a reference population as described hereinabove.

Accordingly, in one embodiment, the present invention relates to an in vitro method for identifying a human subject suffering from an inflammatory disorder, preferably SIRS, sepsis or septic shock, susceptible to respond to an administration of a therapy, in particular of a TREM-1 inhibitor, said method comprising:

a) measuring the level of soluble Triggering Receptors Expressed on Myeloid cells-1 (sTREM-1) in a biological sample from the human subject;
b) comparing the level of sTREM-1 measured at step a) to a predetermined sTREM-1 value obtained from a reference population sTREM-1, said predetermined sTREM-1 value being the third quartile of said reference population;
c) identifying a human subject suffering from an inflammatory disorder, preferably SIRS, sepsis or septic shock with a level of sTREM-1 measured at step a) higher than the third quartile of step b) as susceptible to respond to an administration of a therapy, in particular of a TREM-1 inhibitor.

In one embodiment, the predetermined sTREM-1 value is obtained from a reference population as described hereinabove, wherein the sTREM-1 levels measured in the reference population are divided into five equal-sized groups each corresponding to 20% of the sTREM-1 levels measured in the reference population. As mentioned above, the cut-off values ("quantiles") so dividing the sTREM-1 levels measured in the reference population are called "quintiles". Thus, in one embodiment, the predetermined sTREM-1 value is a sTREM-1 quintile of a reference population as described hereinabove.

According to this embodiment of the present invention:
the sTREM-1 first quintile corresponds to the sTREM-1 value below which 20% of the sTREM-1 levels measured in the reference population lie and above which 80% of the sTREM-1 levels measured in the reference population lie;
the sTREM-1 second quintile corresponds to the sTREM-1 value below which 40% of the sTREM-1 levels measured in the reference population lie and above which 60% of the sTREM-1 levels measured in the reference population lie;
the sTREM-1 third quintile corresponds to the sTREM-1 value below which 60% of the sTREM-1 levels measured in the reference population lie and above which 40% of the sTREM-1 levels measured in the reference population lie; and
the sTREM-1 fourth quintile corresponds to the sTREM-1 value below which 80% of the sTREM-1 levels measured in the reference population lie and above which 20% of the sTREM-1 levels measured in the reference population lie.

In one embodiment, the predetermined sTREM-1 value is the second sTREM-1 quintile of a reference population as described hereinabove.

In one embodiment, the predetermined sTREM-1 value is the third sTREM-1 quintile (i.e., the penultimate sTREM-1 quintile) of a reference population as described hereinabove.

In one embodiment, the predetermined sTREM-1 value is the fourth sTREM-1 quintile (i.e., the last sTREM-1 quintile) of a reference population as described hereinabove.

In one embodiment, the predetermined sTREM-1 value is obtained from a reference population as described hereinabove, wherein the sTREM-1 levels measured in the reference population are divided into ten equal-sized groups each corresponding to 10% of the sTREM-1 levels measured in the reference population. As mentioned above, the cut-off values ("quantiles") so dividing the sTREM-1 levels measured in the reference population are called "deciles". Thus, in one embodiment, the predetermined sTREM-1 value is a sTREM-1 decile of a reference population as described hereinabove.

According to this embodiment of the present invention:
- the sTREM-1 first decile corresponds to the sTREM-1 value below which 10% of the sTREM-1 levels measured in the reference population lie and above which 90% of the sTREM-1 levels measured in the reference population lie;
- the sTREM-1 second decile corresponds to the sTREM-1 value below which 20% of the sTREM-1 levels measured in the reference population lie and above which 80% of the sTREM-1 levels measured in the reference population lie;
- the sTREM-1 third decile corresponds to the sTREM-1 value below which 30% of the sTREM-1 levels measured in the reference population lie and above which 70% of the sTREM-1 levels measured in the reference population lie;
- the sTREM-1 fourth decile corresponds to the sTREM-1 value below which 40% of the sTREM-1 levels measured in the reference population lie and above which 60% of the sTREM-1 levels measured in the reference population lie;
- the sTREM-1 fifth decile corresponds to the sTREM-1 value below which 50% of the sTREM-1 levels measured in the reference population lie and above which 50% of the sTREM-1 levels measured in the reference population lie;
- the sTREM-1 sixth decile corresponds to the sTREM-1 value below which 60% of the sTREM-1 levels measured in the reference population lie and above which 40% of the sTREM-1 levels measured in the reference population lie;
- the sTREM-1 seventh decile corresponds to the sTREM-1 value below which 70% of the sTREM-1 levels measured in the reference population lie and above which 30% of the sTREM-1 levels measured in the reference population lie;
- the sTREM-1 eight decile corresponds to the sTREM-1 value below which 80% of the sTREM-1 levels measured in the reference population lie and above which 20% of the sTREM-1 levels measured in the reference population lie;
- the sTREM-1 ninth decile corresponds to the sTREM-1 value below which 90% of the sTREM-1 levels measured in the reference population lie and above which 10% of the sTREM-1 levels measured in the reference population lie;

In one embodiment, the predetermined sTREM-1 value is the sixth sTREM-1 decile of a reference population as described hereinabove. In one embodiment, the predetermined sTREM-1 value is the seventh sTREM-1 decile of a reference population as described hereinabove. In one embodiment, the predetermined sTREM-1 value is the eight sTREM-1 decile (i.e., the penultimate sTREM-1 decile) of a reference population as described hereinabove.

In one embodiment, the predetermined sTREM-1 value is the ninth sTREM-1 decile (i.e., the last sTREM-1 decile) of a reference population as described hereinabove.

In one embodiment, the predetermined sTREM-1 value is obtained from a reference population as described hereinabove, wherein the sTREM-1 levels measured in the reference population are divided into groups corresponding to a given percentage of the sTREM-1 levels measured in the reference population. As mentioned above, the cut-off values ("quantiles") so dividing the sTREM-1 levels measured in the reference population are called "percentiles". Thus, in one embodiment, the predetermined sTREM-1 value is a sTREM-1 percentile of a reference population as described hereinabove.

According to one embodiment, the predetermined sTREM-1 value is obtained from a reference population as described hereinabove, wherein said value is associated with a predicted mortality rate in the reference population of 20%, 25%, 30%, 35%, 40%, 45%, 50%, 55%, 60%, 65%, 70%, 75%, 80%, 85%, 90%, or 95%.

For example, a predetermined sTREM-1 value associated with a predicted mortality rate in the reference population of 50% means that for subjects of the reference population having a sTREM-1 level higher than said value, the mortality rate is of 50%.

According to one embodiment, the predetermined sTREM-1 value is obtained from a reference population as described hereinabove and comprising patients affected with SIRS, sepsis or septic shock, wherein, in said reference population, more than 20%, 25%, 30%, 35%, 40%, 45%, 50%/a, 55%, 60%, 65%, 70%, 75%, 80%, 85%, 90%, or 95% of the subjects dying in the 28, 90 or 365 days following the first infection or the first hospitalization present a value higher than said the predetermined sTREM-1 value.

According to one embodiment, the predetermined sTREM-1 value, preferably the predetermined sTREM-1 value obtained from a reference population as described hereinabove, is a sTREM-1 level, preferably a blood, plasma or serum level, ranging from about 20 pg/mL to about 6000 pg/mL.

In one embodiment the predetermined sTREM-1 value, preferably the predetermined sTREM-1 value obtained from a reference population as described hereinabove, is a sTREM-1 level, preferably a blood, plasma or serum level, of about 20, 50, 100, 150, 200, 250, 300, 350, 400, 450, 500, 550, 600, 650, 700, 750, 800, 850, 900, 950, 1000, 1050, 1100, 1150, 1200, 1250, 1300, 1350, 1400, 1450, 1500, 1550, 1600, 1650, 1700, 1750, 1800, 1850, 1900, 1950, 2000, 2050, 2100, 2150, 2200, 2250, 2300, 2350, 2400, 2450, 2500, 2550, 2600, 2650, 2700, 2750, 2800, 2850, 2900, 2950, 3000, 3050, 3100, 3150, 3200, 3250, 3300, 3350, 3400, 3450, 3500, 3550, 3600, 3650, 3700, 3750, 3800, 3850, 3900, 3950, 4000, 4050, 4100, 4150, 4200, 4250, 4300, 4350, 4400, 4450, 4500, 4550, 4600, 4650, 4700, 4750, 4800, 4850, 4900, 4950, 5000, 5050, 5100, 5150, 5200, 5250, 5300, 5350, 5400, 5450, 5500, 5550, 5600, 5650, 5700, 5750, 5800, 5850, 5900, 5950 or 6000 pg/mL.

According to one embodiment, the predetermined sTREM-1 value, preferably the predetermined sTREM-1 value obtained from a reference population as described hereinabove, is a sTREM-1 level, preferably a blood, plasma or serum level, ranging from about 30 pg/mL to about 2000 pg/mL.

In one embodiment the predetermined sTREM-1 value, preferably the predetermined sTREM-1 value obtained from a reference population as described hereinabove, is a sTREM-1 level, preferably a blood, plasma or serum level, of about 30, 50, 100, 150, 200, 250, 300, 350, 400, 450, 500, 550, 600, 650, 700, 750, 800, 850, 900, 950, 1000, 1050, 1100, 1150, 1200, 1250, 1300, 1350, 1400, 1450, 1500, 1550, 1600, 1650, 1700, 1750, 1800, 1850, 1900, 1950 or 2000 pg/mL.

According to one embodiment, the predetermined sTREM-1 value, preferably the predetermined sTREM-1 value obtained from a reference population as described hereinabove, is a sTREM-1 level, preferably a blood, plasma or serum level, ranging from about 50 pg/mL to about 1000 pg/mL.

In one embodiment the predetermined sTREM-1 value, preferably the predetermined sTREM-1 value obtained from a reference population as described hereinabove, is a sTREM-1 level, preferably a blood, plasma or serum level, of about 50, 75, 100, 125, 150, 175, 200, 210, 220, 230, 240, 250, 260, 270, 280, 290, 300, 310, 320, 330, 340, 350, 360, 370, 380, 390, 400, 410, 420, 430, 440, 450, 460, 470, 480, 490, 500, 520, 540, 560, 580, 600, 620, 640, 660, 680, 700, 720, 740, 760, 780, 800, 820, 840, 860, 880, 900, 920, 940, 960, 980 or 1000 pg/mL.

According to another embodiment, the predetermined sTREM-1 value, preferably the predetermined sTREM-1 value obtained from a reference population as described hereinabove, is a sTREM-1 level, preferably a blood, plasma or serum level, ranging from about 250 pg/mL to about 400 pg/mL.

In one embodiment, the predetermined sTREM-1 value, preferably the predetermined sTREM-1 value obtained from a reference population as described hereinabove, is a sTREM-1 level, preferably a blood, plasma or serum level, of about 250, 255, 260, 265, 270, 275, 280, 285, 290, 295, 300, 305, 310, 315, 320, 325, 330, 335, 340, 345, 350, 355, 360, 365, 370, 375, 380, 385, 390, 395 or 400 pg/mL.

According to another embodiment, the predetermined sTREM-1 value, preferably the predetermined sTREM-1 value obtained from a reference population as described hereinabove, is a sTREM-1 level, preferably a blood, plasma or serum level, ranging from about 300 pg/mL to about 800 pg/mL.

In one embodiment, the predetermined sTREM-1 value, preferably the predetermined sTREM-1 value obtained from a reference population as described hereinabove, is a sTREM-1 level, preferably a blood, plasma or serum level, of about 300, 305, 310, 315, 320, 325, 330, 335, 340, 345, 350, 355, 360, 365, 370, 375, 380, 385, 390, 395, 400, 405, 410, 415, 420, 425, 430, 435, 440, 445, 450, 455, 460, 465, 470, 475, 480, 485, 490, 495, 500, 505, 510, 515, 520, 525, 530, 535, 540, 545, 550, 555, 560, 565, 570, 575, 580, 585, 590, 595, 600, 605, 610, 615, 620, 625, 630, 635, 640, 645, 650, 655, 660, 665, 670, 675, 680, 685, 690, 695, 700, 705, 710, 715, 720, 725, 730, 735, 740, 745, 750, 755, 760, 765, 770, 775, 780, 785, 790, 795 or 800 pg/mL.

According to another embodiment, the predetermined sTREM-1 value, preferably the predetermined sTREM-1 value obtained from a reference population as described hereinabove, is a sTREM-1 level, preferably a blood, plasma or serum level, ranging from about 350 pg/mL to about 600 pg/mL.

In one embodiment, the predetermined sTREM-1 value, preferably the predetermined sTREM-1 value obtained from a reference population as described hereinabove, is a sTREM-1 level, preferably a blood, plasma or serum level, of about 350, 355, 360, 365, 370, 375, 380, 385, 390, 395, 400, 405, 410, 415, 420, 425, 430, 435, 440, 445, 450, 455, 460, 465, 470, 475, 480, 485, 490, 495, 500, 505, 510, 515, 520, 525, 530, 535, 540, 545, 550, 555, 560, 565, 570, 575, 580, 585, 590, 595 or 600 pg/mL.

According to another embodiment, the predetermined sTREM-1 value, preferably the predetermined sTREM-1 value obtained from a reference population as described hereinabove, is a sTREM-1 level, preferably a blood, plasma or serum level, ranging from about 400 pg/mL to about 500 pg/mL.

In one embodiment, the predetermined sTREM-1 value, preferably the predetermined sTREM-1 value obtained from a reference population as described hereinabove, is a sTREM-1 level, preferably a blood, plasma or serum level, of about 400, 405, 410, 415, 420, 425, 430, 435, 440, 445, 450, 455, 460, 465, 470, 475, 480, 485, 490, 495 or 500 pg/mL.

According to another embodiment, the predetermined sTREM-1 value, preferably the predetermined sTREM-1 value obtained from a reference population as described hereinabove, is a sTREM-1 level, preferably a blood, plasma or serum level, ranging from about 500 pg/mL to about 600 pg/mL.

In one embodiment, the predetermined sTREM-1 value, preferably the predetermined sTREM-1 value obtained from a reference population as described hereinabove, is a sTREM-1 level, preferably a blood, plasma or serum level, of about 500, 505, 510, 515, 520, 525, 530, 535, 540, 545, 550, 555, 560, 565, 570, 575, 580, 585, 590, 595 or 600 pg/mL.

According to one embodiment, the predetermined sTREM-1 value, preferably the predetermined sTREM-1 value obtained from a reference population as described hereinabove, is a sTREM-1 level, preferably a blood, plasma or serum level, determined with an enzyme-linked immunosorbent assay (ELISA).

As indicated above, examples of ELISA assays include, without being limited to, the TREM-1 Quantikine ELISA kit (reference DTRM10C from R&D Systems); the human TREM-1 DuoSet (references DY1278B and DY1278BE from R&D Systems), the sTREM-1 ELISA (reference sTREM-1 ELISA from iQProducts).

In one embodiment, the enzyme-linked immunosorbent assay (ELISA) is the TREM-1 Quantikine ELISA kit (reference DTRM10C from R&D Systems).

In one embodiment, the predetermined sTREM-1 value, preferably the predetermined sTREM-1 value obtained from a reference population as described hereinabove, is a sTREM-1 level, preferably a blood, plasma or serum level, ranging from about 50 pg/mL to about 1000 pg/mL as determined using an ELISA, or a corresponding sTREM-1 level, preferably a blood, plasma or serum level as determined using another immunoassay, such as an electrochemiluminescence immunoassay (ECLIA) or an enzyme-linked fluorescence assay (ELFA).

In one embodiment, the predetermined sTREM-1 value, preferably the predetermined sTREM-1 value obtained from a reference population as described hereinabove, is a sTREM-1 level, preferably a blood, plasma or serum level, of about 50, 75, 100, 125, 150, 175, 200, 210, 220, 230, 240, 250, 260, 270, 280, 290, 300, 310, 320, 330, 340, 350, 360, 370, 380, 390, 400, 410, 420, 430, 440, 450, 460, 470, 480, 490, 500, 520, 540, 560, 580, 600, 620, 640, 660, 680, 700, 720, 740, 760, 780, 800, 820, 840, 860, 880, 900, 920, 940, 960, 980 or 1000 pg/mL, as determined using an ELISA, or a corresponding sTREM-1 level, preferably a blood, plasma or serum level as determined using another immunoassay, such as an ECLIA or an ELFA.

In one embodiment, the predetermined sTREM-1 value, preferably the predetermined sTREM-1 value obtained from a reference population as described hereinabove, is a sTREM-1 level, preferably a blood, plasma or serum level, ranging from about 300 pg/mL to about 800 pg/mL as determined using an ELISA, or a corresponding sTREM-1 level, preferably a blood, plasma or serum level as determined using another immunoassay, such as an ECLIA or an ELFA.

In one embodiment, the predetermined sTREM-1 value, preferably the predetermined sTREM-1 value obtained from a reference population as described hereinabove, is a sTREM-1 level, preferably a blood, plasma or serum level, of about 300, 305, 310, 315, 320, 325, 330, 335, 340, 345, 350, 355, 360, 365, 370, 375, 380, 385, 390, 395, 400, 405, 410, 415, 420, 425, 430, 435, 440, 445, 450, 455, 460, 465, 470, 475, 480, 485, 490, 495, 500, 505, 510, 515, 520, 525, 530, 535, 540, 545, 550, 555, 560, 565, 570, 575, 580, 585, 590, 595, 600, 605, 610, 615, 620, 625, 630, 635, 640, 645, 650, 655, 660, 665, 670, 675, 680, 685, 690, 695, 700, 705, 710, 715, 720, 725, 730, 735, 740, 745, 750, 755, 760, 765, 770, 775, 780, 785, 790, 795 or 800 pg/mL as determined using an ELISA, or a corresponding sTREM-1 level, preferably a blood, plasma or serum level as determined using another immunoassay, such as an ECLIA or an ELFA.

In one embodiment, the predetermined sTREM-1 value, preferably the predetermined sTREM-1 value obtained from a reference population as described hereinabove, is a sTREM-1 level, preferably a blood, plasma or serum level, ranging from about 350 pg/mL to about 600 pg/mL as determined using an ELISA, or a corresponding sTREM-1 level, preferably a blood, plasma or serum level as determined using another immunoassay, such as an ECLIA or an ELFA.

In one embodiment, the predetermined sTREM-1 value, preferably the predetermined sTREM-1 value obtained from a reference population as described hereinabove, is a sTREM-1 level, preferably a blood, plasma or serum level, of about 350, 355, 360, 365, 370, 375, 380, 385, 390, 395, 400, 405, 410, 415, 420, 425, 430, 435, 440, 445, 450, 455, 460, 465, 470, 475, 480, 485, 490, 495, 500, 505, 510, 515, 520, 525, 530, 535, 540, 545, 550, 555, 560, 565, 570, 575, 580, 585, 590, 595 or 600 pg/mL as determined using an ELISA, or a corresponding sTREM-1 level, preferably a blood, plasma or serum level as determined using another immunoassay, such as an ECLIA or an ELFA.

In one embodiment, the predetermined sTREM-1 value, preferably the predetermined sTREM-1 value obtained from a reference population as described hereinabove, is a sTREM-1 level, preferably a blood, plasma or serum level, ranging from about 400 pg/mL to about 500 pg/mL as determined using an ELISA, or a corresponding sTREM-1 level, preferably a blood, plasma or serum level as determined using another immunoassay, such as an ECLIA or an ELFA.

In one embodiment, the predetermined sTREM-1 value, preferably the predetermined sTREM-1 value obtained from a reference population as described hereinabove, is a sTREM-1 level, preferably a blood, plasma or serum level, of about 400, 405, 410, 415, 420, 425, 430, 435, 440, 445, 450, 455, 460, 465, 470, 475, 480, 485, 490, 495 or 500 pg/mL as determined using an ELISA, or a corresponding sTREM-1 level, preferably a blood, plasma or serum level as determined using another immunoassay, such as an ECLIA or an ELFA.

In one embodiment, the predetermined sTREM-1 value, preferably the predetermined sTREM-1 value obtained from a reference population as described hereinabove, is a sTREM-1 level, preferably a blood, plasma or serum level, ranging from about 500 pg/mL to about 600 pg/mL as determined using an ELISA, or a corresponding sTREM-1 level, preferably a blood, plasma or serum level as determined using another immunoassay, such as an ECLIA or an ELFA.

In one embodiment, the predetermined sTREM-1 value, preferably the predetermined sTREM-1 value obtained from a reference population as described hereinabove, is a sTREM-1 level, preferably a blood, plasma or serum level, of about 500, 505, 510, 515, 520, 525, 530, 535, 540, 545, 550, 555, 560, 565, 570, 575, 580, 585, 590, 595 or 600 pg/mL as determined using an enzyme-linked immunosorbent assay (ELISA), or a corresponding sTREM-1 level, preferably a blood, plasma or serum level as determined using another immunoassay, such as an ECLIA or an ELFA.

According to one embodiment, the predetermined sTREM-1 value, preferably the predetermined sTREM-1 value obtained from a reference population as described hereinabove, is a sTREM-1 level, preferably a blood, plasma or serum level, determined with an electrochemiluminescence immunoassay (ECLIA).

As indicated above, examples of electrochemiluminescence immunoassays (ECLIAs) include Elecsys® (Roche Diagnostics).

In one embodiment, the predetermined sTREM-1 value, preferably the predetermined sTREM-1 value obtained from a reference population as described hereinabove, is a sTREM-1 level, preferably a blood, plasma or serum level, ranging from about 20 pg/mL to about 6000 pg/mL as determined using an electrochemiluminescence immunoassay (ECLIA), or a corresponding sTREM-1 level, preferably a blood, plasma or serum level as determined using another immunoassay, such as an enzyme-linked immunosorbent assay (ELISA) or an enzyme-linked fluorescence assay (ELFA).

In one embodiment the predetermined sTREM-1 value, preferably the predetermined sTREM-1 value obtained from a reference population as described hereinabove, is a sTREM-1 level, preferably a blood, plasma or serum level, of about 20, 50, 100, 150, 200, 250, 300, 350, 400, 450, 500, 550, 600, 650, 700, 750, 800, 850, 900, 950, 1000, 1050, 1100, 1150, 1200, 1250, 1300, 1350, 1400, 1450, 1500, 1550, 1600, 1650, 1700, 1750, 1800, 1850, 1900, 1950, 2000, 2050, 2100, 2150, 2200, 2250, 2300, 2350, 2400, 2450, 2500, 2550, 2600, 2650, 2700, 2750, 2800, 2850, 2900, 2950, 3000, 3050, 3100, 3150, 3200, 3250, 3300, 3350, 3400, 3450, 3500, 3550, 3600, 3650, 3700, 3750, 3800, 3850, 3900, 3950, 4000, 4050, 4100, 4150, 4200, 4250, 4300, 4350, 4400, 4450, 4500, 4550, 4600, 4650, 4700, 4750, 4800, 4850, 4900, 4950, 5000, 5050, 5100, 5150, 5200, 5250, 5300, 5350, 5400, 5450, 5500, 5550, 5600, 5650, 5700, 5750, 5800, 5850, 5900, 5950 or 6000 pg/mL as determined using an ECLIA, or a corresponding sTREM-1 level, preferably a blood, plasma or serum level as determined using another immunoassay, such as an ELISA or an ELFA.

In one embodiment, the predetermined sTREM-1 value, preferably the predetermined sTREM-1 value obtained from a reference population as described hereinabove, is a sTREM-1 level, preferably a blood, plasma or serum level, ranging from about 30 pg/mL to about 3000 pg/mL as determined using an ECLIA, or a corresponding sTREM-1 level, preferably a blood, plasma or serum level as determined using another immunoassay, such as an ELISA or an ELFA.

In one embodiment the predetermined sTREM-1 value, preferably the predetermined sTREM-1 value obtained from a reference population as described hereinabove, is a sTREM-1 level, preferably a blood, plasma or serum level, of about 30, 50, 100, 150, 200, 250, 300, 350, 400, 450, 500, 550, 600, 650, 700, 750, 800, 850, 900, 950, 1000, 1050, 1100, 1150, 1200, 1250, 1300, 1350, 1400, 1450, 1500, 1550, 1600, 1650, 1700, 1750, 1800, 1850, 1900, 1950, 2000, 2050, 2100, 2150, 2200, 2250, 2300, 2350, 2400, 2450, 2500, 2550, 2600, 2650, 2700, 2750, 2800, 2850, 2900, 2950 or 3000 pg/mL as determined using an ECLIA, or a corresponding sTREM-1 level, preferably a blood, plasma or serum level as determined using another immunoassay, such as an ELISA or an ELFA.

In one embodiment, the predetermined sTREM-1 value, preferably the predetermined sTREM-1 value obtained from a reference population as described hereinabove, is a sTREM-1 level, preferably a blood, plasma or serum level, ranging from about 500 pg/mL to about 1500 pg/mL, preferably from about 800 pg/mL to about 1200 pg/mL, as determined using an ECLIA, or a corresponding sTREM-1 level, preferably a blood, plasma or serum level as determined using another immunoassay, such as an ELISA or an ELFA.

In one embodiment, the predetermined sTREM-1 value, preferably the predetermined sTREM-1 value obtained from a reference population as described hereinabove, is a sTREM-1 level, preferably a blood, plasma or serum level, ranging from about 500 pg/mL to about 600 pg/mL, from about 600 pg/mL to about 700 pg/mL, from about 700 pg/mL to about 800 pg/mL, from about 800 pg/mL to about 900 pg/mL or from about 900 pg/mL to about 1000 pg/mL as determined using an ECLIA, or a corresponding sTREM-1 level, preferably a blood, plasma or serum level as determined using another immunoassay, such as an ELISA or an ELFA.

In one embodiment the predetermined sTREM-1 value, preferably the predetermined sTREM-1 value obtained from a reference population as described hereinabove, is a sTREM-1 level, preferably a blood, plasma or serum level, of about 500, 520, 540, 560, 580, 600, 620, 640, 660, 680, 700, 720, 740, 760, 780, 800, 820, 840, 860, 880, 900, 920, 940, 960, 980, 1000, 1020, 1040, 1060, 1080, 1100, 1120, 1140, 1160, 1180, 1200, 1220, 1240, 1260, 1280, 1300, 1320, 1340, 1360, 1380, 1400, 1420, 1440, 1460, 1480 or 1500 pg/mL as determined using an ECLIA, or a corresponding sTREM-1 level, preferably a blood, plasma or serum level as determined using another immunoassay, such as an ELISA or an ELFA.

In one embodiment, the predetermined sTREM-1 value, preferably the predetermined sTREM-1 value obtained from a reference population as described hereinabove, is a sTREM-1 level, preferably a blood, plasma or serum level, ranging from about 1000 pg/mL to about 2000 pg/mL, preferably from about 1200 pg/mL to about 1600 pg/mL, as determined using an ECLIA, or a corresponding sTREM-1 level, preferably a blood, plasma or serum level as determined using another immunoassay, such as an ELISA or an ELFA.

In one embodiment, the predetermined sTREM-1 value, preferably the predetermined sTREM-1 value obtained from a reference population as described hereinabove, is a sTREM-1 level, preferably a blood, plasma or serum level, ranging from about 1000 pg/mL to about 1100 pg/mL, from about 1100 pg/mL to about 1200 pg/mL, from about 1200 pg/mL to about 1300 pg/mL, from about 1300 pg/mL to about 1400 pg/mL, from about 1400 pg/mL to about 1500 pg/mL, from about 1500 pg/mL to about 1600 pg/mL, from about 1600 pg/mL to about 1700 pg/mL, from about 1700 pg/mL to about 1800 pg/mL, from about 1800 pg/mL to about 1900 pg/mL or from about 1900 pg/mL to about 2000 pg/mL as determined using an ECLIA, or a corresponding sTREM-1 level, preferably a blood, plasma or serum level as determined using another immunoassay, such as an ELISA or an ELFA.

In one embodiment the predetermined sTREM-1 value, preferably the predetermined sTREM-1 value obtained from a reference population as described hereinabove, is a sTREM-1 level, preferably a blood, plasma or serum level, of about 1000, 1020, 1040, 1060, 1080, 1100, 1120, 1140, 1160, 1180, 1200, 1220, 1240, 1260, 1280, 1300, 1320, 1340, 1360, 1380, 1400, 1420, 1440, 1460, 1480, 1500, 1520, 1540, 1560, 1580, 1600, 1620, 1640, 1660, 1680, 1700, 1720, 1740, 1760, 1780, 1800, 1820, 1840, 1860, 1880, 1900, 1920, 1940, 1960, 1980 or 2000 pg/mL as determined using an ECLIA, or a corresponding sTREM-1 level, preferably a blood, plasma or serum level as determined using another immunoassay, such as an ELISA or an ELFA.

According to one embodiment, the predetermined sTREM-1 value, preferably the predetermined sTREM-1 value obtained from a reference population as described hereinabove, is a sTREM-1 level, preferably a blood, plasma or serum level, determined with an enzyme-linked fluorescent assay (ELFA).

As indicated above, examples of enzyme-linked fluorescent assays (ELFA) include VIDAS® (Biomerieux).

In one embodiment, the predetermined sTREM-1 value, preferably the predetermined sTREM-1 value obtained from a reference population as described hereinabove, is a sTREM-1 level, preferably a blood, plasma or serum level, ranging from about 30 pg/mL to about 3000 pg/mL, preferably from about 300 pg/mL to about 2000 pg/mL, as determined using an ELFA, or a corresponding sTREM-1 level, preferably a blood, plasma or serum level as determined using another immunoassay, such as enzyme-linked immunosorbent assay (ELISA) or an electrochemiluminescence immunoassay (ECLIA).

In one embodiment the predetermined sTREM-1 value, preferably the predetermined sTREM-1 value obtained from a reference population as described hereinabove, is a sTREM-1 level, preferably a blood, plasma or serum level, of about 30, 50, 100, 150, 200, 250, 300, 325, 350, 375, 400, 425, 450, 475, 500, 525, 550, 575, 600, 625, 650, 675, 700, 725, 750, 775, 800, 825, 850, 875, 900, 925, 950, 975, 1000, 1025, 1050, 1075, 1100, 1125, 1150, 1175, 1200, 1225, 1250, 1275, 1300, 1325, 1350, 1375, 1400, 1425, 1450, 1475, 1500, 1525, 1550, 1575, 1600, 1625, 1650, 1675, 1700, 1725, 1750, 1775, 1800, 1825, 1850, 1875, 1900, 1925, 1950, 1975, 2000, 2050, 2100, 2150, 2200, 2250, 2300, 2350, 2400, 2450, 2500, 2550, 2600, 2650, 2700, 2750, 2800, 2850, 2900, 2950 or 3000 pg/mL as determined using an ELFA, or a corresponding sTREM-1 level, preferably a blood, plasma or serum level as determined using another immunoassay, such as an ELISA or an ECLIA.

In one embodiment, the predetermined sTREM-1 value, preferably the predetermined sTREM-1 value obtained from a reference population as described hereinabove, is a sTREM-1 level, preferably a blood, plasma or serum level, ranging from about 500 pg/mL to about 1500 pg/mL, preferably from about 800 pg/mL to about 1200 pg/mL, as determined using an ELFA, or a corresponding sTREM-1 level, preferably a blood, plasma or serum level as determined using another immunoassay, such as an ELISA or an ECLIA.

In one embodiment, the predetermined sTREM-1 value, preferably the predetermined sTREM-1 value obtained from a reference population as described hereinabove, is a sTREM-1 level, preferably a blood, plasma or serum level, ranging from about 500 pg/mL to about 600 pg/mL, from about 600 pg/mL to about 700 pg/mL, from about 700 pg/mL to about 800 pg/mL, from about 800 pg/mL to about 900 pg/mL or from about 900 pg/mL to about 1000 pg/mL as determined using an ELFA, or a corresponding sTREM-1 level, preferably a blood, plasma or serum level as determined using another immunoassay, such as an ELISA or an ECLIA.

In one embodiment the predetermined sTREM-1 value, preferably the predetermined sTREM-1 value obtained from a reference population as described hereinabove, is a sTREM-1 level, preferably a blood, plasma or serum level, of about 500, 520, 540, 560, 580, 600, 620, 640, 660, 680, 700, 720, 740, 760, 780, 800, 820, 840, 860, 880, 900, 920, 940, 960, 980, 1000, 1020, 1040, 1060, 1080, 1100, 1120, 1140, 1160, 1180, 1200, 1220, 1240, 1260, 1280, 1300, 1320, 1340, 1360, 1380, 1400, 1420, 1440, 1460, 1480 or 1500 pg/mL as determined using an ELFA, or a corresponding sTREM-1 level, preferably a blood, plasma or serum level as determined using another immunoassay, such as an ELISA or an ECLIA.

In one embodiment, the predetermined sTREM-1 value, preferably the predetermined sTREM-1 value obtained from a reference population as described hereinabove, is a sTREM-1 level, preferably a blood, plasma or serum level, ranging from about 1000 pg/mL to about 2000 pg/mL, preferably from about 1200 pg/mL to about 1600 pg/mL, as determined using an ELFA, or a corresponding sTREM-1 level, preferably a blood, plasma or serum level as determined using another immunoassay, such as an ELISA or an ECLIA.

In one embodiment, the predetermined sTREM-1 value, preferably the predetermined sTREM-1 value obtained from a reference population as described hereinabove, is a sTREM-1 level, preferably a blood, plasma or serum level, ranging from about 1000 pg/mL to about 1100 pg/mL, from about 1100 pg/mL to about 1200 pg/mL, from about 1200 pg/mL to about 1300 pg/mL, from about 1300 pg/mL to about 1400 pg/mL, from about 1400 pg/mL to about 1500 pg/mL, from about 1500 pg/mL to about 1600 pg/mL, from about 1600 pg/mL to about 1700 pg/mL, from about 1700 pg/mL to about 1800 pg/mL, from about 1800 pg/mL to about 1900 pg/mL or from about 1900 pg/mL to about 2000 pg/mL as determined using an ELFA, or a corresponding sTREM-1 level, preferably a blood, plasma or serum level as determined using another immunoassay, such as an ELISA or an ECLIA.

In one embodiment the predetermined sTREM-1 value, preferably the predetermined sTREM-1 value obtained from a reference population as described hereinabove, is a sTREM-1 level, preferably a blood, plasma or serum level, of about 1000, 1020, 1040, 1060, 1080, 1100, 1120, 1140, 1160, 1180, 1200, 1220, 1240, 1260, 1280, 1300, 1320, 1340, 1360, 1380, 1400, 1420, 1440, 1460, 1480, 1500, 1520, 1540, 1560, 1580, 1600, 1620, 1640, 1660, 1680, 1700, 1720, 1740, 1760, 1780, 1800, 1820, 1840, 1860, 1880, 1900, 1920, 1940, 1960, 1980 or 2000 pg/mL as determined using an ELFA, or a corresponding sTREM-1 level, preferably a blood, plasma or serum level as determined using another immunoassay, such as an ELISA or an ECLIA.

Accordingly, in one embodiment, the present invention relates to an in vitro method for identifying a human subject suffering from an inflammatory disorder, preferably SIRS, sepsis or septic shock, susceptible to respond to an administration of a therapy, in particular of a TREM-1 inhibitor, said method comprising:
  a) measuring the level of soluble Triggering Receptors Expressed on Myeloid cells-1 (sTREM-1) in a biological sample from the human subject;
  b) comparing the level of sTREM-1 measured at step a) to a predetermined sTREM-1 value, preferably obtained from a reference population sTREM-1, said predetermined sTREM-1 value being a blood sTREM-1 level ranging from about 350 pg/mL to about 600 pg/mL;
  c) identifying a human subject suffering from an inflammatory disorder, preferably SIRS, sepsis or septic shock, with a level of sTREM-1 measured at step a) higher than the predetermined sTREM-1 value of step b) as susceptible to respond to an administration of a therapy, in particular of a TREM-1 inhibitor.

In another embodiment, the present invention relates to an in vitro method for identifying a human subject suffering from an inflammatory disorder, preferably SIRS, sepsis or septic shock, susceptible to respond to an administration of a therapy, in particular of a TREM-1 inhibitor, said method comprising:
  a) measuring the level of soluble Triggering Receptors Expressed on Myeloid cells-1 (sTREM-1) in a biological sample from the human subject;
  b) comparing the level of sTREM-1 measured at step a) to a predetermined sTREM-1 value, preferably obtained from a reference population sTREM-1, said predetermined sTREM-1 value being a blood sTREM-1 level ranging from about 300 pg/mL to about 800 pg/mL, preferably from about 350 pg/mL to about 600 pg/mL, as determined using an enzyme-linked immunosorbent assay (ELISA), or a corresponding blood sTREM-1 level as determined using another immunoassay, such as an ECLIA or an ELFA;
  c) identifying a human subject suffering from an inflammatory disorder, preferably SIRS, sepsis or septic shock, with a level of sTREM-1 measured at step a) higher than the predetermined sTREM-1 value of step b) as susceptible to respond to an administration of a therapy, in particular of a TREM-1 inhibitor.

In another embodiment, the present invention relates to an in vitro method for identifying a human subject suffering from an inflammatory disorder, preferably SIRS, sepsis or septic shock, susceptible to respond to an administration of a therapy, in particular of a TREM-1 inhibitor, said method comprising:
  a) measuring the level of soluble Triggering Receptors Expressed on Myeloid cells-1 (sTREM-1) in a biological sample from the human subject;
  b) comparing the level of sTREM-1 measured at step a) to a predetermined sTREM-1 value, preferably obtained from a reference population sTREM-1, said predetermined sTREM-1 value being a blood sTREM-1 level ranging from about 20 pg/mL to about 6000 pg/mL, preferably from about 30 pg/mL to about 3000 pg/mL, as determined using an electrochemiluminescence immunoassay (ECLIA), or a corresponding blood sTREM-1 level as determined using another immunoassay, such as an ELISA or an ELFA;

c) identifying a human subject suffering from an inflammatory disorder, preferably SIRS, sepsis or septic shock, with a level of sTREM-1 measured at step a) higher than the predetermined sTREM-1 value of step b) as susceptible to respond to an administration of a therapy, in particular of a TREM-1 inhibitor.

In another embodiment, the present invention relates to an in vitro method for identifying a human subject suffering from an inflammatory disorder, preferably SIRS, sepsis or septic shock, susceptible to respond to an administration of a therapy, in particular of a TREM-1 inhibitor, said method comprising:

a) measuring the level of soluble Triggering Receptors Expressed on Myeloid cells-1 (sTREM-1) in a biological sample from the human subject;

b) comparing the level of sTREM-1 measured at step a) to a predetermined sTREM-1 value, preferably obtained from a reference population sTREM-1, said predetermined sTREM-1 value being a blood sTREM-1 level ranging from about 30 pg/mL to about 3000 pg/mL, preferably from about 300 pg/mL to about 2000 pg/mL, as determined using an enzyme-linked fluorescent assay (ELFA), or a corresponding blood sTREM-1 level as determined using another immunoassay, such as an ELISA or an ECLIA;

c) identifying a human subject suffering from an inflammatory disorder, preferably SIRS, sepsis or septic shock, with a level of sTREM-1 measured at step a) higher than the predetermined sTREM-1 value of step b) as susceptible to respond to an administration of a therapy, in particular of a TREM-1 inhibitor.

According to one embodiment, the therapy is an immunomodulatory therapy or an anti-inflammatory therapy.

Examples of immunomodulatory therapies or anti-inflammatory therapies include, without being limited to, checkpoint inhibitors such as anti-PD-1, anti-PD-L1 and anti-CTLA4; TLR (Toll-like receptors) inhibitors; cytokine inhibitors such as anti-cytokine or anti-cytokine receptors (for example IL-1RA for interleukin-1 receptor antagonist); G-CSF (granulocyte-colony stimulating factor); GM-CSF (granulocyte-macrophage colony-stimulating factor); IL-7 (interleukin-7); inhibitors of immunostimulants such as CD28 antagonist peptides and antibodies, in particular monoclonal antibodies, against CD28; and cellular therapies such as adoptive cell therapies.

In one embodiment, the therapy is selected from the group consisting of checkpoint inhibitors; TLR (Toll-like receptors) inhibitors; cytokine inhibitors including anti-cytokine or anti-cytokine receptors; G-CSF (granulocyte-colony stimulating factor); IL-7 (interleukin-7); inhibitors of immunostimulants; and cellular therapies. In other words, in one embodiment, the therapy comprises or consists in the administration of at least one of a checkpoint inhibitor; a TLR (Toll-like receptors) inhibitor; a cytokine inhibitor; G-CSF (granulocyte-colony stimulating factor); IL-7 (interleukin-7); GM-CSF (granulocyte-macrophage colony-stimulating factor); an inhibitor of immunostimulants; or a cellular therapy.

As used herein, checkpoint inhibitors (CPI, that may also be referred to as immune checkpoint inhibitors or ICI) refer to compounds that block the interactions between inhibitory receptors expressed on T cells and their ligands. Checkpoint inhibitors include antibodies, in particular monoclonal antibodies, and non-antibody inhibitors such as small molecule inhibitors.

Examples of checkpoint inhibitors include, without being limited to, inhibitors of the cell surface receptor PD-1 (programmed cell death protein 1), also known as CD279 (cluster differentiation 279); inhibitors of the ligand PD-L1 (programmed death-ligand 1), also known as CD274 (cluster of differentiation 274) or B7-H1 (B7 homolog 1); inhibitors of the cell surface receptor CTLA4 or CTLA-4 (cytotoxic T-lymphocyte-associated protein 4), also known as CD152 (cluster of differentiation 152); inhibitors of LAG-3 (lymphocyte-activation gene 3), also known as CD223 (cluster differentiation 223); inhibitors of TIM-3 (T-cell immunoglobulin and mucin-domain containing-3), also known as HAVCR2 (hepatitis A virus cellular receptor 2) or CD366 (cluster differentiation 366); inhibitors of TIGIT (T cell immunoreceptor with Ig and ITIM domains), also known as VSIG9 (V-Set And Immunoglobulin Domain-Containing Protein 9) or VSTM3 (V-Set And Transmembrane Domain-Containing Protein 3); inhibitors of BTLA (B and T lymphocyte attenuator), also known as CD272 (cluster differentiation 272); inhibitors of CEACAM-1 (carcinoembryonic antigen-related cell adhesion molecule 1) also known as CD66a (cluster differentiation 66a).

As used herein, TLR inhibitors (sometimes also referred to as TLR antagonists) refer to compounds that block TLR signaling. TLR inhibitors may act by blocking the binding of TLR ligands to the receptor or by blocking the intracellular signaling pathways to stop the signal transduction (Gao et al., Front Physiol. 2017; 8: 508). TLR inhibitors include, without being limited to, small molecule inhibitors; antibodies, in particular monoclonal antibodies; oligonucleotides; lipid-A analogs; microRNAs; and nano-inhibitors.

As used herein, cytokine inhibitors refer to compound that decrease the synthesis of cytokines, decrease their concentration in free active form, block their interaction with specific receptors or interfere with the signaling of cytokine receptors. Cytokine inhibitors include, without being limited to, antibodies, in particular monoclonal antibodies against cytokines (i.e., anti-cytokine antibodies); antibodies, in particular monoclonal antibodies against cytokine receptors (i.e., anti-cytokine receptor antibodies); cytokine receptor antagonists; and soluble receptors acting as decoy receptors.

According to one embodiment, the therapy is a therapy seeking to inhibit or remove endotoxins, also referred to herein as anti-endotoxin therapy.

Examples of anti-endotoxin therapies include, without being limited to, endotoxin inhibitors such as anti-endotoxin antibodies, in particular anti-endotoxin monoclonal antibodies; recombinant alkaline phosphatase, such as, for example, human recombinant AP (recAP); and hemoperfusion which allows for the removal of a toxin by direct contact of the blood in an extracorporeal circulation with a material that adsorbs the toxin, such as, for example, polymyxin B immobilized fiber cartridge (PMX-DHP).

According to one embodiment, the therapy is a vasopressor therapy. In other words, according to one embodiment, the therapy comprises or consists in the administration of a vasopressor.

Examples of vasopressor therapies include, without limitation, the administration of vasoactive catecholamine hormones such as norepinephrine, dopamine, epinephrine; vasopressin; and/or phenylephrine.

According to one embodiment, the therapy is an angiogenesis inhibitor, in particular an angiopoietin-2 (Ang-2 or Ang2) inhibitor. In other words, according to one embodiment, the therapy comprises or consists in the administration of an angiogenesis inhibitor, in particular an angiopoietin-2 (Ang-2 or Ang2) inhibitor.

The angiopoietin-Tie signaling system, comprising notably angiopoetin-1 (Ang-1) and Tie 2, is a vascular-specific receptor tyrosine kinase pathway that is essential for normal vascular development. Initially Ang-2 was identified as an antagonist of Ang-1, inhibiting the activation of Tie2 by Ang-1. However, it remains unclear whether Ang-2 is an antagonist or agonist of Tie2 in settings of vascular remodeling. A number of studies indicate that Ang-2 plays a role in inflammation-induced vascular remodeling and in tumor angiogenesis and growth (Thurston & Daly, Cold Spring Harb Perspect Med. 2012 Sep. 1; 2(9):a006550).

As used herein, Ang-2 inhibitors (sometimes also referred to as Ang2 antagonists) refer to compounds that block Ang-2 signaling, notably that block Ang-2 and Tie2 interaction. According to the invention, Ang-2 inhibitors thus include inhibitors binding Ang-2 and inhibitors binding Tie2. Examples of Ang-2 inhibitors include, without being limited to antibodies, in particular monoclonal antibodies, against Ang-2; Ang2-Blocking Antibody also referred to as ABA (Han et al., Sci Transl Med. 2016 Apr. 20; 8(335):335ra55); Ang2-Binding and Tie2-Activating Antibody also referred to as ABTAA (Han et al., Sci Transl Med. 2016 Apr. 20; 8(335):335ra55); nanobodies against Ang-2, including bispecific nanobodies that inhibit for example VEGF (vascular endothelial growth factor) and Ang-2; peptibodies against Ang-2, corresponding to the fusion of an inhibitory Ang-2 binding peptide and an Ig Fc domain; soluble decoy receptors also referred to as soluble ligand-trap receptors; oligonucleotides such as antisense RNAs; aptamers such as RNA aptamers specifically blocking Ang-2.

According to one embodiment, the therapy is an adrenomedullin (ADM) and adrenomedullin-targeted therapy.

Examples of adrenomedullin and adrenomedullin-targeted therapies include, without being limited to, adrenomedullin (ADM) such as, for example, a bolus of ADM or a continuous infusion of ADM; antibodies recognizing ADM (anti-AMD antibodies) including antibodies recognizing the biologically active ADM (anti-bio-ADM antibodies), in particular monoclonal antibodies including non-neutralizing antibodies such as Adrecizumab.

According to one embodiment, the therapy is a TREM-1 inhibitor. In other words, according to one embodiment, the therapy comprises or consists in the administration of a TREM-1 inhibitor.

According to the present invention, a TREM-1 inhibitor is an active agent able to inhibit TREM-1 function, activity or expression.

In one embodiment, the TREM-1 inhibitor is selected from the group consisting of peptides inhibiting the function, activity or expression of TREM-1; antibodies directed to TREM-1 and/or sTREM-1, or TREM-1 and/or sTREM-1 ligand; small molecules inhibiting the function, activity or expression of TREM-1; siRNAs directed to TREM-1; shRNAs directed to TREM-1; antisense oligonucleotides directed to TREM-1; ribozymes directed to TREM-1 and aptamers directed to TREM-1.

Accordingly, in one embodiment, the present invention relates to an in vitro method for identifying a human subject suffering from an inflammatory disorder, preferably SIRS, sepsis or septic shock, susceptible to respond to an administration of a TREM-1 inhibitor as described hereinabove, said method comprising:
  a) measuring the level of soluble Triggering Receptors Expressed on Myeloid cells-1 (sTREM-1) in a biological sample from the human subject;
  b) comparing the level of sTREM-1 measured at step a) to a predetermined sTREM-1 value as described hereinabove;
  c) identifying a human subject suffering from an inflammatory disorder, preferably SIRS, sepsis or septic shock with a level of sTREM-1 measured at step a) higher than the predetermined sTREM-1 value of step b) as susceptible to respond to an administration of a TREM-1 inhibitor as described hereinabove.

Examples of peptides inhibiting the function, activity or expression of TREM-1 include, without being limited to, peptides targeting TREM-1 ligand, such as, for example, TLT-1 peptides.

In one embodiment, the TREM-1 inhibitor is a peptide inhibiting TREM-1 through its binding to TREM-1 ligand.

In one embodiment, the TREM-1 inhibitor is a TLT-1 peptide.

In one embodiment, the TREM-1 inhibitor is a short TLT-1 peptide consisting of between 6 and 20 consecutive amino acids from the human TLT-1 having an amino acid sequence as set forth in SEQ ID NO: 7

```
                                            SEQ ID NO: 7
(MGLTLLLLLLLGLEGQGIVGSLPEVLQAPVGSSILVQCHYRLQDVKAQK

VWCRFLPEGCQPLVSSAVDRRAPAGRRTFLTDLGGGLLQVEMVTLQEEDA

GEYGCMVDGARGPQILHRVSLNILPPEEEEETHKIGSLAENAFSDPAGSA

NPLEPSQDEKSIPLIWGAVLLVGLLVAAVVLFAVMAKRKQGNRLGVCGRF

LSSRVSGMNPSSVVHHVSDSGPAAELPLDVPHIRLDSPPSFDNTTYTSLP

LDSPSGKPSLPAPSSLPPLPPKVLVCSKPVTYATVIFPGGNKGGGTSCGP

AQNPPNNQTPSS)
``` or a sequence having at least 60, 65, 70, 75, 80, 85 or 90% identity with the amino acid sequence as set forth in SEQ ID NO: 7.

In one embodiment, the TREM-1 inhibitor is a short TLT-1 peptide consisting of between 6 and 20 consecutive amino acids from the human TLT-1 having an amino acid sequence as set forth in SEQ ID NO: 7 or a function-conservative variant or derivative thereof.

In one embodiment, the TREM-1 inhibitor is a TLT-1 peptide consisting of 6 to 12, 13, 14, 15, 16, 17, 18, 19 or 20 amino acids and comprising an amino acid sequence as set forth in SEQ ID NO: 8 (LQEEDAGEYGCMVDGAR) also referred to as LR17, SEQ ID NO: 9 (LQEED-AGEYGCM) also referred to as LR12, SEQ ID NO: 10 (LQEEDA) also referred to as LR6-1, SEQ ID NO: 11 (EDAGEY) also referred to as LR6-2, or SEQ ID NO: 12 (GEYGCM) also referred to as LR6-3, or a sequence having at least 60, 65, 70, 75, 80, 85 or 90% identity with the amino acid sequence as set forth in SEQ ID NO: 8, SEQ ID NO: 9, SEQ ID NO: 10, SEQ ID NO: 11, or SEQ ID NO: 12, respectively.

In one embodiment, the TREM-1 inhibitor is a TLT-1 peptide consisting of 6 to 12, 13, 14, 15, 16, 17, 18, 19 or 20 amino acids and comprising an amino acid sequence as set forth in SEQ ID NO: 8, SEQ ID NO: 9, SEQ ID NO: 10, SEQ ID NO: 11, or SEQ ID NO: 12 or a function-conservative variant or derivative thereof.

In one embodiment, the TREM-1 inhibitor is a TLT-1 peptide comprising or consisting of an amino acid sequence as set forth in SEQ ID NO: 8, SEQ ID NO: 9, SEQ ID NO: 10, SEQ ID NO: 11, or SEQ ID NO: 12 or a sequence having at least 60, 65, 70, 75, 80, 85 or 90% identity with the amino acid sequence as set forth in SEQ ID NO: 8, SEQ ID NO: 9, SEQ ID NO: 10, SEQ ID NO: 11, or SEQ ID NO: 12, respectively.

In one embodiment, the TREM-1 inhibitor is a TLT-1 peptide comprising or consisting of an amino acid sequence as set forth in SEQ ID NO: 8, SEQ ID NO: 9, SEQ ID NO: 10, SEQ ID NO: 11, or SEQ ID NO: 12 or a function-conservative variant or derivative thereof.

In one embodiment, the TREM-1 inhibitor is a TLT-1 peptide having an amino acid sequence as set forth in SEQ ID NO: 8, SEQ ID NO: 9, SEQ ID NO: 10, SEQ ID NO: 11, or SEQ ID NO: 12 or a sequence having at least 60, 65, 70, 75, 80, 85 or 90% identity with the amino acid sequence as set forth in SEQ ID NO: 8, SEQ ID NO: 9, SEQ ID NO: 10, SEQ ID NO: 11, or SEQ ID NO: 12, respectively.

In one embodiment, the TREM-1 inhibitor is a TLT-1 peptide having an amino acid sequence as set forth in SEQ ID NO: 8, SEQ ID NO: 9, SEQ ID NO: 10, SEQ ID NO: 11, or SEQ ID NO: 12 or a function-conservative variant or derivative thereof.

In one embodiment, the TREM-1 inhibitor is a TLT-1 peptide having an amino acid sequence as set forth in SEQ ID NO: 9, also known as LR12 or nangibotide or motrem, or a sequence having at least 60, 65, 70, 75, 80, 85 or 90% identity with the amino acid sequence as set forth in SEQ ID NO: 9.

In one embodiment, the TREM-1 inhibitor is a TLT-1 peptide having an amino acid sequence as set forth in SEQ ID NO: 9, also known as LR12 or nangibotide or motrem, or a function-conservative variant or derivative thereof.

As used herein, the term "function-conservative variants" denotes peptides derived from the TLT-1 peptides as described hereinabove, in which a given amino acid residue in a peptide has been changed without altering the overall conformation and function of said TLT-1 peptides, including, but not limited to, replacement of an amino acid with one having similar properties (such as, for example, similar polarity, similar hydrogen bonding potential, acidic or basic amino acid replaced by another acidic or basic amino acid, hydrophobic amino acid replaced by another hydrophobic amino acid, aromatic amino acid replaced by another aromatic amino acid).

It is commonly known that amino acids other than those indicated as conserved may differ in a protein so that the percent of protein or amino acid sequence similarity between any two proteins of similar function may vary and may be, for example, from 70% to 99% as determined according to an alignment method such as by the Cluster Method, wherein similarity is based on the MEGALIGN algorithm.

A "function-conservative variant" also includes TLT-1 peptides which have at least 20%, 30%, 40%, 50%, or 60% amino acid identity with the TLT-1 peptides as described hereinabove, for example as determined by BLAST or FASTA algorithms, and which have the same or substantially similar properties or functions as the as the TLT-1 peptides as described hereinabove. Preferably "function-conservative variants" include TLT-1 peptides which have at least 60%, 65%, 70%, 75%, 80%, 85% or 90% amino acid identity with the TLT-1 peptides as described hereinabove and which have the same or substantially similar properties or functions as the TLT-1 peptides as described hereinabove.

As used herein, the term "derivative" refers to a variation of a peptide or of a function-conservative variant thereof that is otherwise modified in order to alter the in vitro or in vivo conformation, activity, specificity, efficacy or stability of the peptide. For example, said variation may encompass modification by covalent attachment of any type of molecule to the peptide or by addition of chemical compound(s) to any of the amino-acids of the peptide.

In one embodiment, the TLT-1 peptide or function-conservative variants or derivatives thereof as described hereinabove may have D- or L-configuration.

In one embodiment, the amino acid from the amino end of the TLT-1 peptide or function-conservative variant or derivative thereof as described hereinabove has an acetylated terminal amino group, and the amino acid from the carboxyl end has an amidated terminal carboxy group.

In addition, the TLT-1 peptide or function-conservative variant or derivative thereof as described hereinabove may undergo reversible chemical modifications in order to increase its bioavailability (including stability and fat solubility) and its ability to pass the blood-brain barrier and epithelial tissue. Examples of such reversible chemical modifications include esterification of the carboxy groups of glutamic and aspartic amino acids with an alcohol, thereby removing the negative charge of the amino acid and increasing its hydrophobicity. This esterification is reversible, as the ester link formed is recognized by intracellular esterases which hydrolyze it, restoring the charge to the aspartic and glutamic residues. The net effect is an accumulation of intracellular peptide, as the internalized, de-esterified peptide cannot cross the cell membrane.

Another example of such reversible chemical modifications includes the addition of a further peptide sequence, which allows the increase of the membrane permeability, such as a TAT peptide or Penetratin peptide (see—Charge-Dependent Translocation of the Trojan. A Molecular View on the Interaction of the Trojan Peptide Penetratin with the 15 Polar Interface of Lipid Bilayers. Biophysical Journal, Volume 87, Issue 1, 1 Jul. 2004, Pages 332-343).

The TLT-1 peptides or function-conservative variants or derivatives thereof as described hereinabove may be obtained through conventional methods of solid-phase chemical peptide synthesis, following Fmoc and/or Boc-based methodology (see Pennington, M. W. and Dunn, B. N. (1994). Peptide synthesis protocols. Humana Press, Totowa.).

Alternatively, the TLT-1 peptides or function-conservative variants or derivatives as described hereinabove may be obtained through conventional methods based on recombinant DNA technology, e.g., through a method that, in brief, includes inserting the nucleic acid sequence coding for the peptide into an appropriate plasmid or vector, transforming competent cells for said plasmid or vector, and growing said cells under conditions that allow the expression of the peptide and, if desired, isolating and (optionally) purifying the peptide through conventional means known to experts in these matters or eukaryotic cells that express the peptide. A review of the principles of recombinant DNA technology may be found, for example, in the text book entitled "Principles of Gene Manipulation: An Introduction to Genetic Engineering," R. W. Old & S. B. Primrose, published by Blackwell Scientific Publications, 4th Edition (1989).

According to one embodiment, the TREM-1 inhibitor is a TLT-1 peptide as described hereinabove, in particular a TLT-1 peptide having an amino acid sequence as set forth in SEQ ID NO: 9, also known as LR12 or nangibotide or motrem, or a sequence having at least 60, 65, 70, 75, 80, 85 or 90% identity with the amino acid sequence as set forth in SEQ ID NO: 9, and said TLT-1 peptide is to be administered to the human subject by continuous infusion, preferably by continuous intravenous infusion, at a dose ranging from about 0.1 mg per kg bodyweight per hour (mg/kg/h) to about 2.5 mg/kg/h, preferably from about 0.3 mg/kg/h to about 1 mg/kg/h, even more preferably from about 0.3 mg/kg/h to about 0.9 mg/kg/h. In one embodiment, said TLT-1 peptide is to be administered to the human subject by continuous infusion, preferably by continuous intravenous infusion, at a dose ranging from about 0.15 g/24h to about 4.5 g/24h, preferably from about 0.5 g/24h to about 2 g/24h, even more preferably from about 0.5 g/24h to about 1.5 g/24h.

In one embodiment, said TLT-1 peptide is to be administered to the human subject by continuous infusion, preferably by continuous intravenous infusion, at a dose of about 0.1, 0.2, 0.3, 0.4, 0.5, 0.6, 0.7, 0.8, 0.9 or 1 mg/kg/h, preferably at a dose of about 0.3 mg/kg/h. In one embodiment, said TLT-1 peptide is to be administered to the human subject by continuous infusion, preferably by continuous intravenous infusion, at a dose of about 0.3 mg/kg/h or about 1 mg/kg/h. In one embodiment, said TLT-1 peptide is to be administered to the human subject by continuous infusion, preferably by continuous intravenous infusion, at a dose of about 0.15, 0.30, 0.45, 0.60, 0.75, 0.90, 1.05, 1.2, 1.35, 1.5, 1.65, 1.8 or 2 g/24h.

In one embodiment, said TLT-1 peptide is to be administered to the human subject for at least 24 hours and/or for at most 5 days. In one embodiment, said TLT-1 peptide is to be administered to the human subject for 24 hours, 48 hours, 72 hours, 96 hours or 120 hours. Thus, in one embodiment, said TLT-1 peptide is to be administered to the human subject for 1 day, 2 days, 3 days, 4 days or 5 days.

In one embodiment, the continuous administration of a TLT-1 peptide as described hereinabove is to be preceded by the administration of a loading dose of TLT-1 peptide. In one embodiment, the loading dose of TLT-1 peptide is a dose ranging from about 0.5 mg/kg to about 5 mg/kg. In one embodiment, the loading dose of TLT-1 is a dose of about 0.5, 0.75, 1, 1.25, 1.5, 1.665, 1.75, 2, 2.25, 2.5, 2.75, 3, 3.25, 3.5, 3.75, 4, 4.25, 4.5, 4.75 or 5 mg/kg, preferably a dose of about 1.665 mg/kg or 5 mg/kg. In one embodiment, the loading dose of TLT-1 peptide as described hereinabove is to be administered over about 15 min, preferably by intravenous injection. Thus, in one embodiment, the loading dose of TLT-1 peptide is a dose ranging from about 2 mg/kg/h to about 20 mg/kg/h. In one embodiment, the loading dose of TLT-1 peptide is a dose of about 2, 3, 4, 5, 6, 6.66, 7, 8, 9, 10, 11, 12, 13, 14, 15, 16, 17, 18, 19 or 20 mg/kg/h, preferably at a dose of 6.66 or 20 mg/kg/h.

According to one embodiment, the therapy as described hereinabove is to be administered between the first 2 hours and the first 24 hours following the start of patient care, in particular following the start of vasopressor therapy.

In one embodiment, the therapy as described hereinabove is to be administered within the first 2, 3, 6, 9, 12, 15, 18, 21 or 24 hours following the start of patient care, in particular following the start of vasopressor therapy.

In one embodiment, the subject is a human patient who is awaiting the receipt of, or is receiving, medical care or was/is/will be the subject of a medical procedure or is monitored for the development or progression of a disease, such as an inflammatory disorder, preferably SIRS, sepsis or septic shock.

In one embodiment, the subject is a human patient who is hospitalized with septic shock.

In one embodiment, the subject is suffering from a documented or suspected infection.

In one embodiment, the subject is suffering from a community-acquired infection. In one embodiment, the subject is suffering from a hospital-acquired infection.

Examples of infections include, without being limited to, respiratory infections, abdominal infections and urinary tract infections (UTIs) meningitis, endocarditis, skin infections, bone infections, wound infections, catheter-related bloodstream infections, device-associated infections.

In one embodiment, the subject is a man. In another embodiment, the subject is a woman. In one embodiment, the subject is a pregnant woman.

In one embodiment, the subject is an adult. In one embodiment, the subject is an elderly subject. In one embodiment, the subject is a child. In one embodiment, the subject is an infant. In one embodiment, the subject is a newborn.

In one embodiment, the subject is not immunocompromised, immunosuppressed or immunodeficient. In another embodiment, the subject is immunocompromised, immunosuppressed or immunodeficient. In another embodiment, the subject is receiving an immunosuppressive therapy.

In one embodiment, the subject is afflicted with a chronic medical condition such as atrial fibrillation, cancer, chronic kidney disease, chronic lung disease, cirrhosis, coronary artery disease, deep vein thrombosis, diabetes, dyslipidemia, endocarditis, hypertension, influenza, malaria or any other protozoan parasitic disease, myocardial infarction, neurological disease, non-alcoholic fatty liver disease (NAFLD), non-alcoholic steatohepatitis (NASH), peripheral artery disease, pulmonary fibrosis, severe obesity and stroke.

According to one embodiment, the inflammatory disorder is selected from the group comprising or consisting of systemic inflammatory response syndrome (SIRS), sepsis, septic shock, sepsis-associated organ dysfunction, acute respiratory distress syndrome (ARDS), severe acute respiratory syndrome (SARS), acute kidney injury (AKI), pancreatitis, inflammatory bowel disease, pneumonia, endotoxemia and hemorrhagic shock.

According to one embodiment, the inflammatory disorder is an acute inflammatory disorder.

Examples of acute inflammatory disorders include, without being limited to, systemic inflammatory response syndrome (SIRS), sepsis, septic shock, acute respiratory distress syndrome (ARDS), acute kidney injury (AKI), pancreatitis and hemorrhagic shock.

In one embodiment, the acute inflammatory disorder is selected from the group comprising or consisting of systemic inflammatory response syndrome (SIRS), sepsis, septic shock, acute respiratory distress syndrome (ARDS), acute kidney injury (AKI), pancreatitis and hemorrhagic shock.

According to one embodiment, the inflammatory disorder is selected from the group comprising or consisting of systemic inflammatory response syndrome (SIRS), sepsis, septic shock, acute respiratory distress syndrome (ARDS) and acute kidney injury (AKI).

In one embodiment, the inflammatory disorder is systemic inflammatory response syndrome (SIRS), sepsis or septic shock.

In one embodiment, the inflammatory disorder is septic shock.

Systemic inflammatory response syndrome (SIRS) is characterized by systemic inflammation and widespread tissue injury. Clinically, SIRS is defined as fulfilling at least two of the following four criteria: fever >38.0° C. or hypothermia <36.0° C.; tachycardia >90 beats/minute; tachypnea >20 breaths/minute; and leukocytosis >12×10$^9$/L or leucopenia <4×10$^9$/L (Bone et al., Chest. 1992 June; 101 (6):1644-55). SIRS may occur as a response to a nonspecific insult of either infectious or non-infectious origin. Examples of insults of non-infectious origin include, without being limited to, trauma, thermal injury, pancreatitis, autoimmune disorders and surgery. Examples of insults of infectious origin include bacterial infections (e.g., respiratory infections, abdominal infections and urinary tract infections (UTIs), fungal infections (e.g., respiratory infections) and viral infections (e.g., respiratory infections).

As mentioned hereinabove, sepsis is defined as a life-threatening organ dysfunction caused by a dysregulated response of the human subject to infection (Singer et al., JAMA. 2016 Feb. 23; 315(8):801-10). Patients with sepsis can be clinically identified as patients suffering from a documented or suspected infection and from an organ dysfunction. In one embodiment, organ dysfunction in a human subject can be identified using an organ dysfunction score, i.e., a score used to assess organ dysfunction in a human subject, notably upon admission in ICU or emergency unit. Examples of organ dysfunction scores include, without being limited to, the SOFA score, the qSOFA score, the MODS (Multiple Organ Dysfunction Score), the P-MODS (Pediatric Multiple Organ Dysfunction Score) and the LODS (Logistic Organ Dysfunction System). In one embodiment, organ dysfunction in a human subject can be identified as an acute change in the total SOFA score of 2 points or greater, consequent to the infection (Singer et al., JAMA. 2016 Feb. 23; 315(8):801-10). The baseline SOFA score can be assumed to be zero in patients not known to have preexisting organ dysfunction (Singer et al., JAMA. 2016 Feb. 23; 315(8):801-10).

Septic shock is defined as a subset of sepsis, in which particularly profound circulatory, cellular, and metabolic abnormalities are associated with a greater risk of mortality than with sepsis alone. Thus, sepsis encompasses septic shock. Patients with septic shock can be clinically identified as patients suffering from sepsis and having (i) persisting hypotension requiring vasopressors to maintain their mean arterial pressure ≥65 mm Hg despite adequate volume resuscitation and (ii) a serum lactate level >2 mmol/L (18 mg/dL) (Sepsis-3 definition as described in Singer et al., JAMA. 2016 Feb. 23; 315(8):801-10). With these criteria, hospital mortality is in excess of 40%. (Singer et al., JAMA. 2016 Feb. 23; 315(8):801-10).

In one embodiment, the infection inducing the dysregulated response of the human subject suffering from SIRS, sepsis or septic shock is a bacterial, fungal or viral infection.

Examples of infections include, without being limited to, respiratory infections, abdominal infections and urinary tract infections (UTIs).

According to one embodiment, the human subject suffering from SIRS, sepsis or septic shock may be assessed using a severity score, i.e., a score used to assess the severity of the disease and/or the prognosis upon admission in ICU or emergency unit. Examples of severity scores include, without being limited to, the APACHE II score, the APACHE III score, the APACHE IV score, the SAPS score, the SAPS II score and the SAPS 3 score.

In one embodiment, the human subject suffering from SIRS, sepsis or septic shock may be assessed using the APACHE II (referring to "Acute Physiology And Chronic Health Evaluation II") scoring system. APACHE II is commonly used to assess the severity of disease in adult patients admitted in intensive care units and determine their prognostic. APACHE II uses a point score ranging from 0 to 71 that is based upon the initial values of 12 routine physiologic measurements, age, and previous health status to provide a general measure of severity of disease (Knaus et al., Crit Care Med. 1985 October; 13(10):818-29). The APACHE II score may be determined during the first 24h upon admission in intensive care unit (ICU) or emergency unit. A higher score is associated with a higher predicted mortality, with a score of 25 representing a predicted mortality of 50% and a score of over 35 representing a predicted mortality of 80%.

In one embodiment, the human subject suffering from SIRS, sepsis or septic shock has an APACHE II score lower than 34. In one embodiment, the human subject suffering from SIRS, sepsis or septic shock is not moribund.

In one embodiment, the human subject suffering from SIRS, sepsis or septic shock may be assessed using the APACHE III (referring to "Acute Physiology And Chronic Health Evaluation" III) scoring system. APACHE III was redefined from the APACHE II scoring system in order to more accurately predict hospital mortality risk for critically ill hospitalized adults (Knaus et al., Chest. 1991 December; 100(6):1619-36).

In one embodiment, the human subject suffering from SIRS, sepsis or septic shock may be assessed using the APACHE IV (referring to "Acute Physiology And Chronic Health Evaluation IV") scoring system. APACHE IV is an improved and updated model for estimating the risk of short-term mortality as well as predicting the length of intensive care unit (ICU) stay (Zimmerman et al., Crit Care Med. 2006 May; 34(5):1297-310). In the APACHE IV scoring system, a greater number of variables are considered, notably mechanical ventilation, thrombolysis, impact of sedation on Glasgow Coma Scale, rescaled Glasgow Coma Scale, $PaO_2/FiO_2$ ratio and disease-specific subgroups. APACHE IV uses a point score ranging from 0 to 286.

In one embodiment, the human subject suffering from SIRS, sepsis or septic shock may be assessed using the SAPS II (referring to "Simplified Acute Physiology Score II") scoring system. SAPS II is a scoring system for estimating in-hospital mortality in adult patients admitted to the intensive care unit (ICU). SAPS II include 17 variables: 12 physiology variables, age, type of admission, and 3 variables regarding underlying diseases (Le Gall et al., JAMA. 1993 Dec. 22-29; 270(24):2957-63). SAPS II uses a point score ranging from 0 to 163.

In one embodiment, the human subject suffering from SIRS, sepsis or septic shock may be assessed using the SAPS 3 (referring to "Simplified Acute Physiology Score III") scoring system. SAPS 3 is a scoring system for predicting hospital mortality of patients admitted to the intensive care unit (ICU) (Metnitz et al., Intensive Care Med. 2005 October; 31(10): 1336-1344 and Moreno et al., Intensive Care Med. 2005 October; 31(10):1345-55). SAPS 3 is based on 20 different variables.

As mentioned hereinabove, the presence of organ dysfunction associated with sepsis or septic shock may be assessed using an organ dysfunction score such as the SOFA score, the qSOFA score, the MODS (Multiple Organ Dysfunction Score), the P-MODS (Pediatric Multiple Organ Dysfunction Score) or the LODS (Logistic Organ Dysfunction System).

The Sequential Organ Failure Assessment (SOFA) score (originally referred to as the Sepsis-related Organ Failure Assessment, Vincent et al., Intensive Care Med. 1996 July;

22(7):707-10) is a scoring system commonly used to assess organ dysfunction in a human subject notably upon admission in ICU or emergency unit. The SOFA scoring system (Vincent et al., Crit Care Med. 1998 November; 26(11):1793-800) relies on the assessment of the respiratory system (i.e., $PaO_2/FiO_2$ (mmHg)), the nervous system (i.e., Glasgow coma scale), the cardiovascular system (i.e., mean arterial pressure or administration of vasopressors required), the liver function (i.e., bilirubin (mg/dL or µmol/L)), coagulation (i.e., platelet count), the kidney function (i.e., creatinine (mg/dL or µmol/L) or urine output (mL/d)).

The baseline SOFA score can be assumed to be zero in patients not known to have preexisting (acute or chronic) organ dysfunction before the onset of infection. A SOFA score of at least 2 points reflects an overall mortality risk of approximately 10% in a general hospital population with suspected infection (Singer et al., JAMA. 2016 Feb. 23; 315(8):801-10).

In one embodiment, the human subject is suffering from SIRS, sepsis or septic shock associated with a SOFA score of at least 2 points.

In one embodiment, the human subject is suffering from SIRS, sepsis or septic shock associated with an organ dysfunction defined as an acute change in his/her SOFA score of at least 2 points.

The presence of organ dysfunction associated with sepsis or septic shock may also be assessed using the quick SOFA score (also referred to as quickSOFA or qSOFA). The qSOFA scoring system relies on three criteria: respiratory rate ≥22 breaths/min; altered mentation (Glasgow coma scale <15); and systolic blood pressure ≥100 mm Hg (Seymour et al., JAMA. 2016 Feb. 23; 315(8):762-74).

In one embodiment, the human subject is suffering from SIRS, sepsis or septic shock associated with a qSOFA score of at least 2 points.

In one embodiment, the human subject is suffering from SIRS, sepsis or septic shock associated with an organ dysfunction defined as an acute change in his/her qSOFA score of at least 2 points.

According to one embodiment, the human subject is suffering from septic shock.

According to one embodiment, the human subject is suffering from SIRS, sepsis or septic shock, preferably septic shock, and receiving the standard of care. The standard of care, in particular the standard of care for septic shock, may include, without being limited to, fluid therapy, vasopressor therapy as described hereinabove, cardiovascular support, respiratory support (such as mechanical ventilation), renal support and/or sedation. Thus, in one embodiment, the human subject is suffering from suffering from SIRS, sepsis or septic shock, preferably septic shock, and receiving fluid therapy, vasopressor therapy as described hereinabove, cardiovascular support, respiratory support (such as mechanical ventilation), renal support and/or sedation.

According to the present invention, the human subjects suffering from an inflammatory disorder, preferably SIRS, sepsis or septic shock identified with the method as described hereinabove are susceptible to respond to an administration of a therapy, in particular of a TREM-1 inhibitor; as described hereinabove.

According to one embodiment, the aim of the method described hereinabove is to identify human subjects suffering from an inflammatory disorder, preferably SIRS, sepsis or septic shock who are "responder", i.e., who respond or are susceptible to respond to an administration of a therapy, in particular of a TREM-1 inhibitor, as described hereinabove.

Conversely, in the present invention, human subjects suffering from an inflammatory disorder, preferably SIRS, sepsis or septic shock, who are "non-responder" are human subjects who do not respond or are not susceptible to respond to an administration of a therapy, in particular of a TREM-1 inhibitor, as described hereinabove.

According to one embodiment, for a human subject suffering from an inflammatory disorder, preferably SIRS, sepsis or septic shock, a response to the administration of a therapy, in particular of a TREM-1 inhibitor, as described hereinabove is characterized by at least one of the following occurring after the administration of the TREM-1 inhibitor:

a reversal of a hypotensive shock, preferably within or after the administration period of the therapy, preferably a TREM-1 inhibitor, for example over the 6, 12, 18 or 24 hours following the end of said administration, wherein a shock reversal is defined as the absence of any vasopressor therapy during 24 hours (i.e., not requiring to restart a vasopressor therapy in the 24 hours following the end of a vasopressor therapy);

a decrease of a severity score used to assess the severity of the disease and/or the prognosis of a human subject suffering from an inflammatory disorder, preferably SIRS, sepsis or septic shock upon admission in ICU or emergency unit, such as the APACHE II score, the APACHE III score, the APACHE IV score, the SAPS score, the SAPS II score or the SAPS 3 score;

a decrease of an organ dysfunction score used to assess the presence of organ dysfunction in a human subject suffering from an inflammatory disorder, preferably SIRS, sepsis or septic shock upon admission in ICU or emergency unit, such as the SOFA score, the qSOFA score, the MODS (Multiple Organ Dysfunction Score), the P-MODS (Pediatric Multiple Organ Dysfunction Score) or the LODS (Logistic Organ Dysfunction System);

a decrease of the SOFA score and/or of the qSOFA score, in particular over the 1, 2, 3, 4, 5, 6 or 7 day(s) following the start of the administration of the therapy, preferably a TREM-1 inhibitor, preferably with reference to the SOFA score and/or the qSOFA score assessed upon admission in ICU or emergency unit or before the start of the administration of the therapy; in one embodiment, said decrease of the SOFA score is a decrease of at least 1 point (also referred as a delta of −1 point or ΔSOFA of −1 point), preferably of at least 1.5 point, in particular at day 3 or at day 5 following the start of the administration of the therapy, preferably with reference to the SOFA score and/or the qSOFA score assessed upon admission in ICU or emergency unit or before the start of the administration of the therapy;

a decrease in the requirement for cardiovascular support, for example a decrease in the use of vasopressor therapy, in particular over the 1, 2, 3, 4, 5, 6 or 7 day(s) following the start of the administration of the therapy, preferably a TREM-1 inhibitor, preferably with reference to the requirement for cardiovascular support upon admission in ICU or emergency unit or before the start of the administration of the therapy;

a decrease in the requirement for respiratory support, for example a decrease in the use of invasive mechanical ventilation (IMV), in particular over the 1, 2, 3, 4, 5, 6 or 7 day(s) following the start of the administration of the therapy, preferably a TREM-1 inhibitor, preferably with reference to the requirement for respiratory support upon admission in ICU or emergency unit or before the start of the administration of the therapy;

a decrease in the requirement for renal support, for example a decrease in the use of continuous or discontinuous renal replacement therapy also referred to as RRT (e.g., dialysis), in particular over the 1, 2, 3, 4, 5, 6 or 7 day(s) following the start of the administration of the therapy, preferably a TREM-1 inhibitor, preferably with reference to the requirement for renal support upon admission in ICU or emergency unit or before the start of the administration of the therapy;

a decrease in the risk of reinfection, in particular a decrease in the risk of reinfection in the 28, 90 or 365 days following the initial inflammatory disorder, in particular the initial infection responsible for an inflammatory disorder;

an absence of reinfection, in particular an absence of reinfection in the 28, 90 or 365 days following the initial inflammatory disorder, in particular the initial infection responsible for an inflammatory disorder;

a decrease in the risk of rehospitalization, in particular a decrease in the risk of reinfection in the 28, 90 or 365 days following the initial inflammatory disorder, in particular the initial infection responsible for an inflammatory disorder;

an absence of rehospitalization, in particular an absence of rehospitalization in the 28, 90 or 365 days following the first hospitalization;

an increase in the chance of survival, in particular 1-year, 2-year, 3-year, 4-year, 5-year, 6-year, 7-year, 8-year, 9-year or 10-year survival, following the start of the administration of the therapy, preferably a TREM-1 inhibitor; in one embodiment the chance of survival, in particular in a subject with multiple comorbidities, is assessed with the Charlson Comorbidity Index (CCI) and an increase in the chance of 10-year survival corresponds to a decrease of the Charlson Comorbidity Index, preferably with reference to CCI assessed upon admission in ICU or emergency unit or before the start of the administration of the therapy;

a decrease in the risk of sepsis-related death, in particular at day 5, day 28, day 90 or day 365 following the start of the administration of the therapy, preferably a TREM-1 inhibitor;

a decrease in the risk of the all-cause death, in particular at day 5, day 28, day 90 or day 365 following the start of the administration of the therapy, preferably a TREM-1 inhibitor;

a decrease in the risk of post-sepsis or post-shock morbidity, in particular at day 5, day 28, day 90 or day 365 following the start of the administration of the therapy, preferably a TREM-1 inhibitor;

an increase in the quality of life, in particular in the post-sepsis or post-shock quality of life that may be assessed for example through an evaluation of survival and quality-adjusted life years (QALYs), estimated from the EQ5D. For example, health-related quality of life (HRQoL) scores from the EQ 5D 5L may be calculated and converted to utility scores, in particular at 3 months, 6 months, 9 months, 12 months, 18 months, 24 months or 36 months following the start of the administration of the therapy;

a decrease in the level of an inflammatory marker, such as, for example, CRP or IL6, IL-8, IL-10, MCP-1 and TNF-α), in particular over the 1, 2, 3, 4, 5, 6 or 7 day(s) following the start of the administration of the therapy, preferably a TREM-1 inhibitor, preferably with reference to the level assessed upon admission in ICU or emergency unit or before the start of the administration of the therapy; or a decrease in the level of an endothelial injury marker, such as, for example, Ang-2, VCAM-1, VGEFR-1 and E-selectin, in particular over the 1, 2, 3, 4, 5, 6 or 7 day(s) following the start of the administration of the therapy, preferably a TREM-1 inhibitor, preferably with reference to the level assessed upon admission in ICU or emergency unit or before the start of the administration of the therapy.

In one embodiment, a human subject suffering from SIRS, sepsis or septic shock, preferably septic shock, susceptible to respond to the administration of a therapy, in particular of a TREM-1 inhibitor, as described hereinabove, i.e., a responder, is a human subject suffering from SIRS, sepsis or septic shock, preferably septic shock, susceptible to reverse a hypotensive shock, preferably within or after the administration period of the therapy, in particular of a TREM-1 inhibitor, for example over the 6, 12, 18 or 24 hours following the end of said administration, wherein a hypotensive shock reversal is defined as the absence of any vasopressor therapy during 24 hours (i.e., not requiring to restart a vasopressor therapy in the 24 hours following the end of a vasopressor therapy).

Conversely, in one embodiment, a human subject suffering from SIRS, sepsis or septic shock, preferably septic shock, not susceptible to respond to the administration of a therapy, in particular of a TREM-1 inhibitor, as described hereinabove, i.e., a non-responder, is a human subject suffering from SIRS, sepsis or septic shock preferably septic shock, unable to reverse a hypotensive shock, preferably within or after the administration period of the therapy, in particular of a TREM-1 inhibitor, for example over the 6, 12, 18 or 24 hours following the end of said administration, wherein a hypotensive shock reversal is defined as the absence of any vasopressor therapy during 24 hours, or is a human subject suffering from SIRS, sepsis or septic shock, preferably septic shock, requiring the restarting of a vasopressor therapy within the 6, 12, 18 or 24 hours following withdrawal of the therapy, in particular of a TREM-1 inhibitor.

In one embodiment, a responder is a human subject suffering from SIRS, sepsis or septic shock, who following the administration of a TREM-1 inhibitor as described hereinabove, is susceptible to have his/her sequential organ failure assessment (SOFA) score decrease.

In one embodiment, a responder is a human subject suffering from SIRS, sepsis or septic shock, who following the administration of a TREM-1 inhibitor as described hereinabove, is susceptible to have his/her sequential organ failure assessment (SOFA) score decrease with reference to the SOFA score assessed upon admission in ICU or emergency unit or before the start of the administration of the therapy.

As used herein, the difference in the SOFA score following the administration of a TREM-1 inhibitor, in particular with reference to the SOFA score assessed upon admission in ICU or emergency unit or before the start of the administration of the therapy, may also be referred to as the delta SOFA score or ΔSOFA score.

In one embodiment, a responder is a human subject suffering from SIRS, sepsis or septic shock, who following the administration of a TREM-1 inhibitor as described hereinabove, is susceptible to have his/her SOFA score decrease by at least 1 point, preferably by at least 1.5 point, in particular with reference to the SOFA score assessed upon admission in ICU or emergency unit or before the start of the administration of the therapy.

Thus, in one embodiment, a responder is a human subject suffering from SIRS, sepsis or septic shock, who following the administration of a TREM-1 inhibitor as described hereinabove, is susceptible to have a delta SOFA score (ΔSOFA score) of at least −1 point (minus 1 point), preferably at least −1.5 point (minus 1.5 point).

In one embodiment, said decrease of the SOFA score, in particular the decrease by at least 1 point, preferably at least 1.5 point, is the decrease assessed at day 1, 2, 3, 4, 5, 6 or 7 following the start of the administration of the therapy, preferably at day 3 or at day 5 following the start of the administration of the therapy.

Thus, in one embodiment, said delta SOFA score (ΔSOFA score) is the delta SOFA score assessed at day 1, 2, 3, 4, 5, 6 or 7 following the start of the administration of the therapy, preferably at day 3 or at day 5 following the start of the administration of the therapy.

With the present application, the Applicant shows that measuring the level of soluble TREM-1 (sTREM-1) in a biological sample from human subjects suffering from septic shock and comparing their measured level of sTREM-1 to a predetermined sTREM-1 value allows to identify the human subjects suffering from septic shock susceptible to respond to a TREM-1 inhibitor. In particular, the Applicant shows that human subjects suffering from septic shock with a circulatory level of sTREM-1 higher than the median sTREM-1 level predetermined in a reference population of human subjects suffering from septic shock are more likely to respond to, and thus benefit from, the administration of a TLT-1 peptide inhibiting TREM-1 activity.

A prompt patient care is critical for the prognosis of subjects suffering from SIRS, sepsis or septic shock.

Measuring the level of sTREM-1, in particular the level of sTREM-1 protein, can be carried out very rapidly, notably with a point-of-care testing (POCT) or bedside testing, or with a central laboratory assay (near-to-patient assay). The level of sTREM-1 may thus be measured shortly following the onset of SIRS, sepsis or septic shock; following the diagnosis of the human subject with SIRS, sepsis or septic shock; following the hospitalization, in particular the admission in ICU or emergency unit, of the human subject for SIRS, sepsis or septic shock; or following the start of vasopressor therapy. Results may be thus available within the first 2, 3, 6, 9, 12, 15, 18, 21 or 24 hours, and a care plan may be decided upon immediately thereafter.

EXAMPLES

The present invention is further illustrated by the following examples.

Example 1

Materials and Methods

Cell Culture and Stimulation

The human myelomonocytic cell lines U937 (Culture Collections, Public Health England No. 85011440) were cultured in RPMI 1640 Glutamax supplemented with 10% fetal calf serum, 25 mM Hepes, and 100 U/ml penicillin and streptomycin (all from Thermo Fisher Scientific, USA). For some experiments, U937 cells were cultured under the same conditions supplemented with 100 nM of 1,25-dihydroxyvitamin D3 (Sigma-Aldrich, USA) to induce upregulation of TREM-1 (U937-vitD cells). For shedding experiments, Pro-MMP-9 was activated by pre-incubation with 1 mM APMA for 24 h at 37° C. Cells were seeded at $0.5 \times 10^6$ cells/mL and stimulated with LPS from *Escherichia coli* 0127:B8 (10 pg/mL; Sigma-Aldrich), Pro-MMP-9 (1 µg/mL; R&D systems, Abingdon, UK), p-aminophenylmercuric acetate (APMA; 1 mM; Sigma-Aldrich), and APMA-activated MMP-9 (1 µg/mL) at 37° C. for 30 min. Cell supernatants were collected and sTREM-1 was measured using Human TREM-1 Quantikine ELISA Kit (Biotechne, R&D Systems) according to the manufacturer's instructions.

FACS Analysis

TREM-1 expression was detected by FACS after staining with 5 µL allophycocyanin (APC) conjugated mouse monoclonal anti-human TREM-1 or the corresponding isotype-APC antibodies (Miltenyi Biotec, Germany) for 30 min at 4° C. in dark. After washing with PBS twice, cells were re-suspended and fixed with 4% paraformaldehyde. Accuri C6 flow cytometer (Becton Dickinson, San Jose, CA, USA) was used for analysis.

Confocal Microscopy

Cells were seeded at $0.3 \times 10^6$ cells/well and stimulated with LPS from *Escherichia coli* 0127:B8 (1 µg/mL; Sigma-Aldrich) on LabTek chambers (Thermo Fisher Scientific) for 1 h. After stimulation, cells were washed and fixed with paraformaldehyde (4%) for 20 min and permeabilized with Triton 0.1% for 30 min prior to incubation with the primary antibodies (anti-hTREM-1-AF488; Bioss, USA) at 4° C. overnight. Nuclei were stained with TO-PRO-3 (1 µg/mL; Invitrogen, USA) for 1 h at 37° C. After washing, coverslips were mounted using a solution of Vectashield (Vector Laboratories, USA). Confocal images were obtained using a Leica SP5 confocal lasers canning microscope system (Leica, Germany) fitted with appropriated filter sets and acquired in sequential scan mode.

Results sTRFM-1 is a Marker of TREM-1 Activation.

Figure 1B:
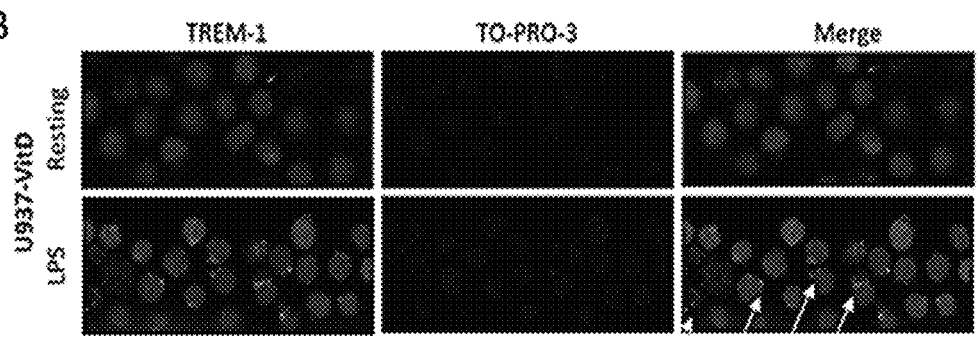
Figure 1C:
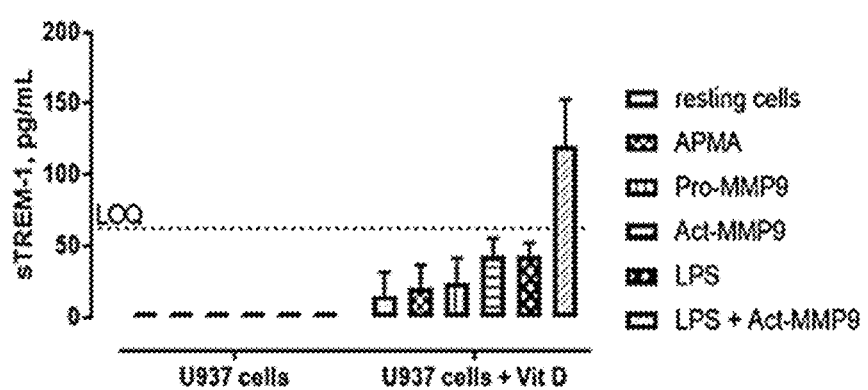

We had previously described that TREM-1 dimerization is essential for its activation on innate immune cells (Carrasco et al., Cell Mol Immunol. 2018 Mar. 22). It is triggered by the initial engagement of TLRs. Indeed, stimulation of human primary monocytes and neutrophils was able to induce the mobilization and clustering of TREM-1 at the membrane. The dimeric configuration of TREM-1 was thus identified to be the active conformation of the receptor, able to bind its endogenous ligand and able to induce activation of downstream intracellular pathway. It has been previously demonstrated that metalloproteinases are responsible for shedding of the TREM-1 ectodomain through proteolytic cleavage of its long juxtamembrane linker (Gomez-Piña et al., J Immunol. 2007 Sep. 15; 179(6):4065-73). We demonstrated here that this shedding necessitates TREM-1 dimerization, suggesting that the release of sTREM-1 is only possible when the receptor is in its active conformation. TREM-1 is expressed at very low levels on resting U937 cells, and it is upregulated when vitamin D is added to the culture media (FIG. 1A). To investigate whether the proteolytic cleavage of TREM-1 and subsequent release of sTREM-1 was linked to the active conformation of TREM-1, we measured sTREM-1 in the supernatant of U937 and U937-vitD cells, after 15-min incubation with LPS and/or Act-MMP9. TREM-1 expression was diffuse at the membrane of resting U937-vitD cells, and LPS was able to induce the clustering and dimerization of TREM-1 at the membrane (FIG. 1B, white arrows). No sTREM-1 was detectable in the supernatant of U937 cells, neither after LPS stimulation nor addition of activated-MMP9 (Act-MMP9). Incubation of U937-vitD cells with LPS or Act-MMP9 alone was not associated with a release of sTREM-1. Interestingly, sTREM-1 was released by U937-vitD cells only in the condition where U937-vitD were co-stimulated with LPS and Act-MMP9 (FIG. 1C). These results confirm that the MMP9-induced proteolytic cleavage of TREM-1 is only possible when TREM-1 is in its dimeric state, which is the active conformation of the receptor. sTREM-1 may thus be a reliable biomarker of TREM-1 receptor activation.

Example 2

Materials and Methods sTREM-1 Measurements: Validated EISA Method for the Quantitative Determination of sTREM-1 in Human $K_2$-EDTA Plasma The quantitative determination of sTREM-1 was carried out using a commercial kit (Human TREM-1 Quantikine ELISA, BioTechne, R&D Systems) and quality control (QC) samples at 3 concentration levels: QC Low (101 pg/mL), QC Mid (532 pg/mL) and QC High (1080 pg/mL) for routine assay.

A pre-study assay qualification was performed to determine the intra-run precision and accuracy of the assay. A pre-study assay qualification run consists in calibration standards and QC samples at 5 concentration levels (LLOQ (41.3 pg/mL), Low, Mid, High and ULOQ (1440 pg/mL), each QC samples must be processed in sextuplate per assay. For each concentration level, the final calculation of intra-run imprecision and inaccuracy must not use less than 5 out of the 6 values. The intra-run imprecision must be less than or equal to 20% (25% at the LLOQ and ULOQ) and the intra-run inaccuracy must be within ±20% (25% at the LLOQ and ULOQ). Pre-study assays must be validated 3 times before starting routine assays.

Standard (STD) samples were prepared freshly each analysis day using Calibrator diluent RD5-18 and the Human TREM-1 standard from the kit. STD samples were prepared to obtain 10 points in the calibration curve: 3000, 2000, 1000, 750, 500, 250, 125, 62.5, 31.3 and 15.6 pg/mL. Calibration standards at 3000 and 15.6 pg/mL were used as anchoring points (Lowest calibration standard (LCS) and Higher calibration standard (HCS) of the calibration curve.

100 µL of Assay Diluent RD1-27 were added to each well. 50 µL of Standard, QC or Samples were then added per well. Plate are incubated for 2 hours at room temperature on a microplate shaker at 450 rpm. After that 2-hour incubation, plates were manually washed 3 times with Wash Buffer, and 200 µL of Human TREM-1 Conjugate were added to each well. Plate were incubated for 2 supplementary hours at room temperature on a microplate shaker at 450 rpm. After washing, 200 µL of Substrate Solution were added to each well. Plate were incubated for 30 minutes at room temperature in the dark. Optical Density (OD) was read at 650 nm (pre-read), and when the OD(650 nm) of HCS was about 1.0, 50 µL of Stop Solution were added to each well. Then, the OD(450 nm) of each well within 30 minutes was measured.

The calibration curve was obtained by plotting the optical density versus the concentrations of the calibration standards, using the logistic curve (4-PL) and 1/y2 weighting factor.

Calibration standards from 2000 to 31.3pg/mL were excluded from the final calibration curve only if the back-calculated inaccuracy was outside ±20% (±25% at the LCS and HCS), or for reasons of instrument failure, or for a documented problem during preparation or assay, or if the coefficient of variation (CV %) on concentration on replicate determination (n=2 wells per calibration standard) was higher than 20%. No more than 30% of these calibration standards may be excluded from each series of calibration standards and the final calibration curve must contain at least 6 non-zero calibration concentration levels including the LCS and the HCS. Blank (0.00 pg/mL), which consisted in Calibrator Diluent RD5-18, was not used for the calculation of the calibration curve.

Each routine run included 6 QC samples (n=2 in duplicate at 3 concentration levels). At least 4 of the 6 QC samples must be within acceptance criteria (with at least one value within acceptance criteria for each concentration level). Acceptance criteria were defined as follows: the individual inaccuracy calculated on the concentration from duplicate determination (n=2 wells per sample) must be within ±20% compared to the nominal value. The coefficient of variation (CV %) on the concentration of replicate determination must be less than or equal to 20%.

The coefficient of variation (CV %) on the concentration of replicate determination (n=2 wells per test sample) of test samples must also be less than or equal to 20%.

Evaluation of sTREM-1 in the AdrenOSS Cohort (NCT02393781)

This study was an ancillary investigation of septic shock patients from the AdrenOSS study (NCT02393781), a European prospective, observational, multinational study in 24 centers from 5 countries (France, Belgium, the Netherlands, Italy, and Germany). Patients were recruited from June 2015 to May 2016. The study protocol was approved by the local ethical committees and conducted in accordance with Directive 2001/20/EC, as well as Good Clinical Practices (I.C.H. version 4 of May 1, 1996 and Decision of Nov. 24, 2006) and the Declaration of Helsinki. The patients who were enrolled were 18 years and older and were (i) admitted to the ICU for sepsis or septic shock or (ii) transferred from another ICU in the state of sepsis and septic shock within less than 24 hours after primary admission. If patients were treated with vasopressors, they were considered eligible only if treatment had been started within a maximum of 24 hours after the primary admission before ICU admission. When patients were included, they were stratified by severe sepsis and septic shock based on the definitions for sepsis and organ failure from 2001. Exclusion criteria were pregnancy, vegetative coma, and participation in an interventional trial in the preceding month. Informed consent was obtained from all patients or their lawful representatives prior to enrollment in the study. Patients were treated according to current guidelines, and all treatments and procedures were registered. sTREM-1 was measured in blood samples withdrawn at baseline (also referred to as day 1 or d1), day 2 (d2) and day 3 (d3).

Statistical Analysis for the AdrenOSS Cohort

Analysis was performed on 293 septic shock patients. The demographic and baseline characteristics are summarized in a descriptive fashion within each population: categorical variables were summarized by contingency tables (frequencies and percentages). Continuous variables were summarized by their mean, standard deviation, standard error, median, quartiles and range, minimum and maximum values. sTREM-1 levels at day 1 (independently referring to baseline, or entry to ICU) were also described (mean, standard deviation, standard error, median, quartiles and range, minimum and maximum values) and separately within the population and subgroups as defined. 28-day mortality rates were estimated within each quartile of the distribution of sTREM-1 levels at day 1. Time to death was analyzed in a proportional hazards COX regression model. A ROC Area Under Curve (AUC) with its 95% CI to predict 28-day mortality from sTREM-1 day 1 levels was calculated. An optimal sTREM-1 cut-off was estimated based i) on the minimization of the distance between the point (0,1) on the upper left-hand corner of ROC space and any point on ROC curve and ii) on the Youden index. Boxplots of sTREM-1 by survivor/non-survivors and RRT (renal replacement therapy) were plotted. When necessary, sTREM-1 data were log transformed. The association of sTREM-1 levels at day 1 and 28-day mortality was assessed in univariable and multivariable logistic regression models adjusted for sTREM-1 at baseline (day 1) as well as adjusted for other prognostic factors (age, gender, cardiac comorbidities, non-cardiac comorbidities and lactate (maximum or minimum on day 1), SOFA at D1, APACHE II at D1, SAPS II at D1.

Results sTRFM-1 is a Prognostic Marker in Septic Shock Patients: Results from the AdrenOSS Cohort The demographics and general baseline characteristics of patients in the whole population, and in each sTREM-1 quartiles are depicted in Table 1 below. No significant differences were observed in patients between the four sTREM-1 quartile groups (Q1, Q2, Q3 and Q4) for baseline characteristics, age, gender, BMI (Body Mass Index), type of ICU admission, origin of sepsis, medical history, and physiological values at admission. The first quartile group, i.e., Q1, comprises patients who had a sTREM-1 level lower than the first quartile value (299 pg/mL), that is to say patients who had a sTREM-1 level between 42 and 299 pg/mL. The second quartile group, i.e., Q2, comprises patients who had a sTREM-1 level between the first quartile value (299 pg/mL) and the second quartile value (497 pg/mL), that is to say patients who had a sTREM-1 level between 299 pg/mL and 497 pg/mL. The third quartile group, i.e., Q3, comprises patients who had a sTREM-1 level between the second quartile value (497 pg/mL) and the third quartile value (809 pg/mL), that is to say patients who had a sTREM-1 level between 497 pg/mL and 809 pg/mL. The fourth quartile group, i.e., Q4, comprises patients who had a sTREM-1 level higher than the third quartile value (809 pg/mL), that is to say patients who had a sTREM-1 level between 809 pg/mL and 5540 pg/mL. There was a significant correlation between sTREM-1 values and lactate levels, arterial pH, creatinine levels, urea levels and PCT levels at baseline. sTREM-1 levels were also correlated with renal replacement therapy (RRT), SOFA, SAPS II and APACHE II scores at baseline, as well as with 28-day and 90-day mortality. 28-day mortality rates were 12.2%, 30.1%, 37% and 49.3% in quartiles Q1, Q2, Q3 and Q4, respectively. Overall mortality rate was 32%. These results confirm that the level of TREM-1 pathway activation at entry to ICU, assessed through the measurement of plasma sTREM-1, is associated with a more complicated outcome in septic shock patients.

TABLE 1

Demographic and General Characteristics, comorbidities, chronic medications, clinical signs at admission of patients from the Adreno's cohort. SOFA.4 = SOFA score without liver and CNS component

| Characteristics | all n = 293 | STREM-1 Q1 (42,299] n = 74 | STREM-1 Q2 (299,497] n = 73 | STREM-1 Q3 (497,809] n = 73 | STREM-1 Q4 (809,5540] n = 73 | p-value |
|---|---|---|---|---|---|---|
| STREM-1 at admission (pg/ml) | 497 [299-809] | | | | | |
| Age (year) | 67.2 [57.8-77.1] | 63.2 [52.5-70.0] | 69.8 [60.0-76.4] | 69.9 [58.7-81.1] | 66.7 [60.4-77.1] | 0.0055 |
| Females (No. %) | 106 (36.2) | 22 (29.7) | 27 (37) | 28 (38.4) | 29 (39.7) | 0.5931 |
| Body Mass Index (kg/m2) | 25.9 [23.0-30.4] | 25.9 [22.9-29.6] | 25.4 [22.5-29.0] | 26.7 [23.3-30.0] | 28.4 [23.9-33.3] | 0.1056 |
| Type of ICU admission: | | | | | | 0.1452 |
| Medical | 215 (73.4) | 55 (74.3) | 53 (72.6) | 54 (74) | 53 (72.6) | |
| Surgical-emergency procedure | 67 (22.9) | 19 (25.7) | 14 (19.2) | 15 (20.5) | 19 (26) | |
| Surgical-elective procedure | 11 (3.8) | 0 (0) | 6 (8.2) | 4 (5.5) | 1 (1.4) | |
| Origin of sepsis: | | | | | | 0.4141 |
| Lung | 81 (27.6) | 26 (35.1) | 24 (32.9) | 16 (21.9) | 15 (20.5) | |
| Blood stream | 40 (13.7) | 5 (6.8) | 8 (11) | 14 (19.2) | 13 (17.8) | |
| Urinary tract | 50 (17.1) | 9 (12.2) | 13 (17.8) | 14 (19.2) | 14 (19.2) | |
| Catheter | 19 (6.5) | 4 (5.4) | 4 (5.5) | 8 (11) | 3 (4.1) | |
| Peritonitis | 17 (5.8) | 4 (5.4) | 3 (4.1) | 6 (8.2) | 4 (5.5) | |
| Endocarditis | 18 (6.1) | 6 (8.1) | 4 (5.5) | 3 (4.1) | 5 (6.8) | |
| Bile duct infection | 4 (1.4) | 1 (1.4) | 1 (1.4) | 2 (2.7) | 0 (0) | |
| CNS | 3 (1) | 2 (2.7) | 0 (0) | 0 (0) | 1 (1.4) | |
| Other | 61 (20.8) | 17 (23) | 16 (21.9) | 10 (13.7) | 18 (24.7) | |
| Medical history OR specific diseases (COPD, DMII, immunodysfunction, chronic renal failure, ischemic or congestive heart disease) | | | | | | |
| any cardiac comorbidity (yes) | 213 (72.7) | 47 (63.5) | 49 (67.1) | 59 (80.8) | 58 (79.5) | 0.0386 |
| any non-cardiac comorbidity (yes) | 226 (77.1) | 56 (75.7) | 59 (80.8) | 56 (76.7) | 55 (75.3) | 0.8513 |
| any chronic medication (yes) | 204 (69.6) | 51 (68.9) | 53 (72.6) | 52 (71.2) | 48 (65.8) | 0.8182 |
| Physiological values at admission | | | | | | |
| Temperature (° C.) | 37.1 [36.1-38] | 37.4 [36.6-38.3] | 37.15 [36.27-37.92] | 37.1 [36.3-37.9] | 36.6 [35.8-37.4] | 0.0052 |
| Mean blood pressure (mmHg) | 103 [89.25-124.75] | 106.5 [92-135.75] | 106 [92.5-120] | 102 [85-118] | 100 [83-125.5] | 0.3179 |
| Heart rate (bpm) | 56 [46-68] | 61.5 [48-71.75] | 56 [48-68] | 54 [45-68] | 53 [43.75-65] | 0.2095 |
| Central Venous pressure (mmHg) | 71 [60-84] | 72.5 [65-93] | 73 [64-82] | 71.5 [56-79.75] | 66 [58-82.5] | 0.0636 |
| Glasgow score | 21 [18-26.5] | 21 [18-27] | 22 [17.75-27] | 21 [18-26] | 22 [18-26] | 0.9260 |
| Fluid Balance (ml) | 105 [92-121.25] | 109.5 [95-124.5] | 99.5 [92-116.25] | 105 [86-124] | 105 [86-121] | 0.5021 |
| PaO2/FiO2 | 205 [128-326] | 217 [123-354] | 225.5 [134.5-287.75] | 179.5 [132.25-294.75] | 228.5 [121.5-330.5] | 0.5418 |

TABLE 1-continued

Demographic and General Characteristics, comorbidities, chronic medications, clinical signs at admission of patients from the Adreno's cohort. SOFA.4 = SOFA score without liver and CNS component

| Characteristics | all n = 293 | STREM-1 Q1 (42,299] n = 74 | STREM-1 Q2 (299,497] n = 73 | STREM-1 Q3 (497,809] n = 73 | STREM-1 Q4 (809,5540] n = 73 | p-value |
|---|---|---|---|---|---|---|
| *Laboratory values at admission* | | | | | | |
| Lactate (mmol/L) | 3.0 [2.0-5.2] | 2.5 [1.5-3.4] | 2.7 [2.0-4.7] | 3.5 [2.0-5.7] | 4.2 [2.7-9.7] | <0.0001 |
| Arterial pH | 7.35 [7.27-7.42] | 7.4 [7.33-7.46] | 7.36 [7.29-7.43] | 7.32 [7.26-7.4] | 7.29 [7.18-7.38] | <0.0001 |
| Bilirubin (µmol/L) | 11 [6-21] | 10.5 [7-18.25] | 11 [7-22.5] | 10 [6-19] | 12 [6-21.5] | 0.9628 |
| Platelets (109/L) | 190 [114-269] | 186 [108.25-251] | 210 [122-287] | 191 [123-239] | 159 [107-291] | 0.6676 |
| Creatinine (mg/dL) | 1.65 [1.06-2.72] | 0.93 [0.68-1.3] | 1.4 [1.06-1.96] | 2.08 [1.53-3.27] | 2.66 [1.79-4.21] | <0.0001 |
| BUN or Urea (mg/dL) | 72 [45.65-120] | 52.25 [33.03-67.2] | 64.26 [44.44-102.11] | 92 [60.06-130.931] | 111.11 [60.66-149] | <0.0001 |
| Hematocrit (%) | 34 [29-38] | 32 [28-36] | 32.5 [28.75-37] | 35 [29-39] | 34 [29-39] | 0.1827 |
| White blood count (per mm3) | 12550 [6270-18700] | 10940 [6467-16827] | 12000 [7135-17000] | 11945 [5135-18287] | 14600 [8300-221201 | 0.2185 |
| Troponin T, maximum on day 1 | 55 [25-232.5] | 37.86 [17.25-160] | 33.5 [20.75-160.51 | 54 [39-200.5] | 133.1 [68-245.5] | 0.1605 |
| Troponin I, maximum on day 1 | 130 [48.5-395.5] | 175 [52.5-381.57] | 63.1 [31.55-192.45] | 232.95 [113.72-612.02] | 84.7 [39.28-583.25] | 0.1402 |
| PCT, maximum on day 1 (ng/mL) | 17.66 [4.49-66.61] | 8.03 [2.59-25.88] | 7.51 [3.92-24] | 31 [8.42-84] | 57 [17.62-113.5] | <0.0001 |
| BNP, maximum on day 1 | 383 [112-1262] | 210.3 [102.25-580.251 | 179.8 [87-257] | 1639 [1260.05-2208.851 | 376.2 [138.5-881] | 0.0091 |
| NT-proBNP, maximum on day 1 | 7957 [2764-16926] | 4162 [519-10203] | 5428 [2783-13924] | 9757 [4170-19402] | 11108 [7209-22440] | 0.0399 |
| *Organ support at admission* | | | | | | |
| Mechanical ventilation: | | | | | | 0.1110 |
| invasive | 149 (50.9) | 34 (45.9) | 34 (46.6) | 36 (49.3) | 45 (61.6) | |
| non-invasive | 47 (16) | 8 (10.8) | 12 (16.4) | 14 (19.2) | 13 (17.8) | |
| none | 97 (33.1) | 32 (43.2) | 27 (37) | 23 (31.5) | 15 (20.5) | |
| Renal replacement therapy (yes) | 38 (13) | 1 (1.4) | 5 (6.8) | 9 (12.3) | 23 (31.5) | <0.0001 |
| *Organ dysfunction scores* | | | | | | |
| SOFA (points) | 9 [7-11] | 7 [6-10] | 9 [7-11] | 10 [8.5-12] | 11 [9-13] | <0.0001 |
| SOFA.4 (points) | 8 [7-10] | 7 [6-8.75] | 8 [6-9] | 9 [7-10] | 10 [8-11] | <0.0001 |
| SAPS2 (points) | 58 [46-71] | 52 [42.25-60] | 55 [44-69] | 59 [48-71] | 65 [57-77] | <0.0001 |
| APACHE 2 (points) | 18 [13-22] | 15 [11-18.75] | 15 [12-20] | 18 [15-23] | 21 [17-24] | <0.0001 |
| *Mortality (%)* | | | | | | |
| 28-day, deaths | 94 (32.1) | 9 (12.2) | 22 (30.1) | 27 (37) | 36 (49.3) | <0.0001 |
| 90-day, deaths | 116 (39.6) | 14 (18.9) | 24 (32.9) | 36 (49.3) | 42 (57.5) | <0.0001 |

*p-value from non-parametric Kruskal-Wallis or Chi$^2$ test, respectively.

Figure 2A:
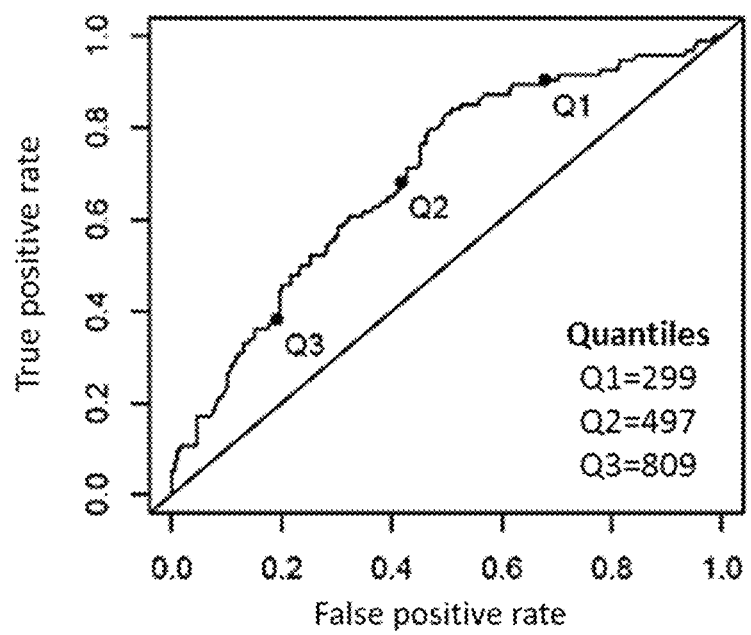
FIGS. 2A-2B are a set of graphs showing that TREM-1 at baseline is correlated to 28-day mortality. ROC plot (FIG. 2A) and Kaplan-Meier plot (FIG. 2B) by quartiles for 28-day mortality. Mortality rates (at day 28) per quartile are 12%, 30%, 37% and 49% for Q1-Q4, respectively. Overall mortality rate is 32%. Optimal cut point was determined to be at 408 pg/mL.
Figure 2B:
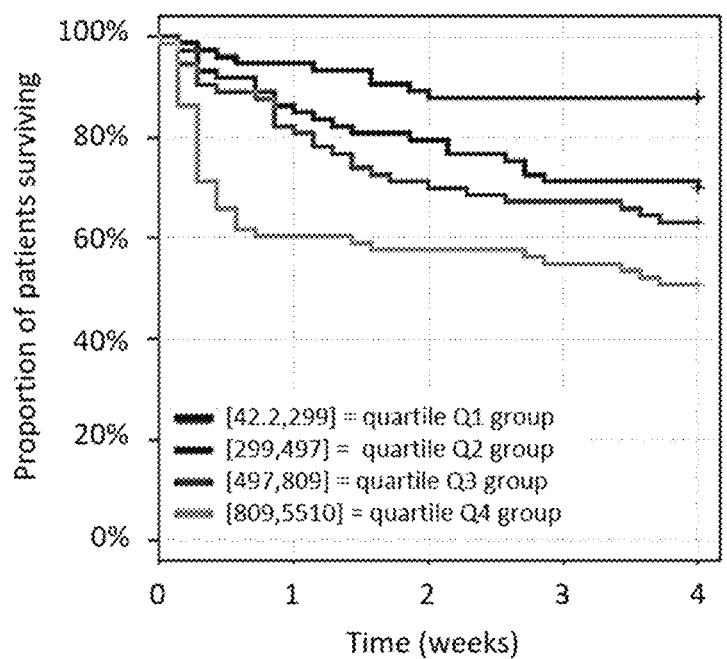

FIG. 2A depicts the ROC plot. FIG. 2B describes the survival of the patients over time in form of a Kaplan-Meier Curve. Patients with the lowest sTREM-1 values (Q1 quartile group) had a better survival at 28-day than patients with the highest sTREM-1 values (Q2 to Q4 quartile groups). The survival rates within the sTREM-1 quartile groups were 87.8%, 69.9%/, 63%, and 50.7% from Q1 to Q4, respectively. An optimal cutoff value was calculated at 408 pg/mL for predicting mortality from the data presented in Table 2 below.

TABLE 2

Cut off shifting: sensitivity and specificity for last timepoint (28 days) based on Nearest Neighbor Estimation (NNE) and Kaplan-Meier (KM) method.

| Cutoff | Quantile | NNE.Sens | NNE. Spec | sumNNE | KM.Sens | KM.Spec | sumKM |
|---|---|---|---|---|---|---|---|
| −Inf | 0 | 100 | 0 | 100 | 100 | 0 | 100 |
| 121 | 1.7 | 99.1 | 2 | 101.1 | 98.9 | 2 | 100.9 |
| 155 | 3.4 | 98.3 | 4.1 | 102.4 | 98.9 | 4.5 | 103.4 |
| 178 | 5.5 | 97.5 | 6.7 | 104.2 | 96.8 | 6.5 | 103.3 |
| 186 | 7.5 | 96.6 | 9.2 | 105.8 | 95.7 | 9 | 104.7 |
| 201 | 9.6 | 95.5 | 11.6 | 107.1 | 95.7 | 12.1 | 107.8 |
| 210 | 11.3 | 94.6 | 13.6 | 108.2 | 95.7 | 14.6 | 110.3 |
| 231 | 13.7 | 93.8 | 16.6 | 110.4 | 94.7 | 17.6 | 112.3 |
| 241 | 16.4 | 92.8 | 20.1 | 112.9 | 92.6 | 20.6 | 113.2 |
| 254 | 19.1 | 91.8 | 23.5 | 115.3 | 91.5 | 24.1 | 115.6 |
| 268 | 20.8 | 91.1 | 25.6 | 116.7 | 91.5 | 26.6 | 118.1 |
| 282 | 22.5 | 90.3 | 27.7 | 118 | 91.5 | 29.1 | 120.6 |
| 296 | 24.9 | 89.5 | 30.7 | 120.2 | 90.4 | 32.2 | 122.6 |
| 307 | 27 | 88.7 | 33.2 | 121.9 | 89.4 | 34.7 | 124.1 |
| 323 | 28.7 | 87.9 | 35.3 | 123.2 | 89.4 | 37.2 | 126.6 |
| 330 | 30.7 | 86.7 | 37.7 | 124.4 | 87.2 | 39.2 | 126.4 |

TABLE 2-continued

Cut off shifting: sensitivity and specificity for last timepoint (28 days) based on Nearest Neighbor Estimation (NNE) and Kaplan-Meier (KM) method.

| Cutoff | Quantile | NNE.Sens | NNE. Spec | sumNNE | KM.Sens | KM.Spec | sumKM |
|---|---|---|---|---|---|---|---|
| 340 | 33.4 | 85.1 | 40.9 | 126 | 87.2 | 43.2 | 130.4 |
| 349 | 35.5 | 83.6 | 43.2 | 126.8 | 85.1 | 45.2 | 130.3 |
| 372 | 38.2 | 81.3 | 46.1 | 127.4 | 84 | 48.7 | 132.7 |
| 380 | 40.3 | 79.4 | 48.2 | 127.6 | 81.9 | 50.8 | 132.7 |
| 396 | 42.3 | 77.5 | 50.3 | 127.8 | 79.8 | 52.8 | 132.6 |
| 409 | 44 | 75.7 | 51.9 | 127.6 | 76.6 | 53.8 | 130.4 |
| 444 | 46.1 | 73.1 | 53.8 | 126.9 | 72.3 | 54.8 | 127.1 |
| 467 | 48.1 | 70.4 | 55.5 | 125.9 | 71.3 | 57.3 | 128.6 |
| 490 | 49.8 | 68 | 57 | 125 | 68.1 | 58.3 | 126.4 |
| 515 | 51.9 | 65.3 | 58.8 | 124.1 | 64.9 | 59.8 | 124.7 |
| 536 | 53.6 | 63.2 | 60.3 | 123.5 | 63.8 | 61.8 | 125.6 |
| 553 | 56 | 60.3 | 62.5 | 122.8 | 61.7 | 64.3 | 126 |
| 577 | 58 | 57.9 | 64.4 | 122.3 | 60.6 | 66.8 | 127.4 |
| 616 | 60.1 | 55.7 | 66.4 | 122.1 | 58.5 | 68.8 | 127.3 |
| 628 | 61.8 | 53.8 | 68 | 121.8 | 56.4 | 70.4 | 126.8 |
| 648 | 64.5 | 50.7 | 70.6 | 121.3 | 52.1 | 72.4 | 124.5 |
| 665 | 66.2 | 48.5 | 72.1 | 120.6 | 52.1 | 74.9 | 127 |
| 690 | 67.9 | 46.2 | 73.6 | 119.8 | 50 | 76.4 | 126.4 |
| 723 | 70 | 43.3 | 75.3 | 118.6 | 47.9 | 78.4 | 126.3 |
| 732 | 71.7 | 40.8 | 76.7 | 117.5 | 45.7 | 79.9 | 125.6 |
| 763 | 73.4 | 38.4 | 78.1 | 116.5 | 41.5 | 80.4 | 121.9 |
| 809 | 75.1 | 35.9 | 79.5 | 115.4 | 38.3 | 81.4 | 119.7 |
| 825 | 76.8 | 33.3 | 80.8 | 114.1 | 36.2 | 82.9 | 119.1 |
| 847 | 78.8 | 30.1 | 82.4 | 112.5 | 34 | 84.9 | 118.9 |
| 866 | 80.5 | 27.5 | 83.8 | 111.3 | 33 | 86.9 | 119.9 |
| 925 | 82.3 | 24.8 | 85.1 | 109.9 | 29.8 | 87.9 | 117.7 |
| 1010 | 84.6 | 20.9 | 86.9 | 107.8 | 26.6 | 89.9 | 116.5 |
| 1100 | 87.4 | 16.3 | 88.9 | 105.2 | 21.3 | 91.5 | 112.8 |
| 1210 | 91.1 | 11.7 | 92.3 | 104 | 17 | 95 | 112 |
| 1300 | 93.9 | 8.7 | 94.9 | 103.6 | 10.6 | 96 | 106.6 |
| 1600 | 95.6 | 6.7 | 96.5 | 103.2 | 10.6 | 98.5 | 109.1 |
| 2100 | 97.3 | 4.8 | 98.1 | 102.9 | 7.4 | 99.5 | 106.9 |
| 2560 | 99 | 2.9 | 99.7 | 102.6 | 3.2 | 100 | 103.2 |

No interaction was observed between the sTREM-1 level and age, gender, lactate, cardiac comorbidities, non-cardiac comorbidities, SOFA, SOFAA4, APACHE2, or SAPS2 (all interactions p>0.1). sTREM-1 was an independent predictor of 28-day mortality and provided additional information to all tested covariates (all p<0.001).

Figure 3A:
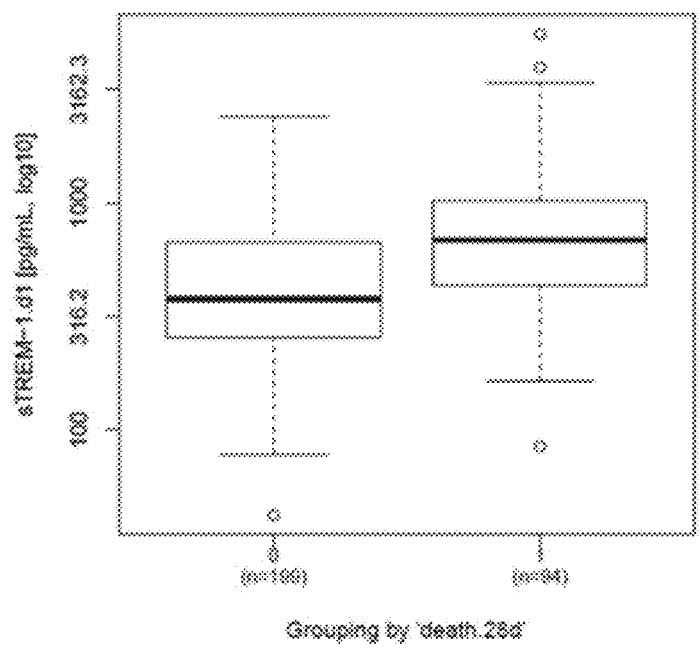
FIGS. 3A-3B are a set of boxplots of sTREM-1 at baseline (day 1) for 28-day mortality (FIG. 3A) and 90-day mortality (FIG. 3B). Chi$^2$ of Kruskal-Wallis test is 28.8 and 29.5, respectively (both p<0.0001).
Figure 3B:
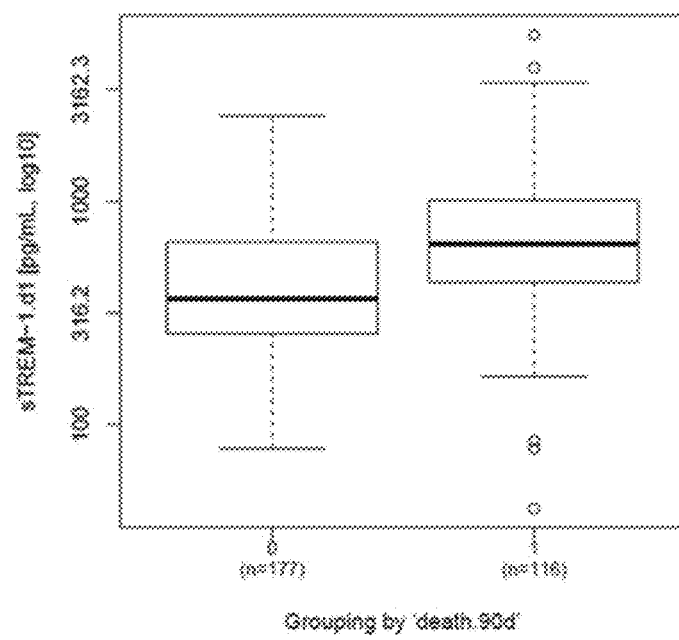
Figure 4A:
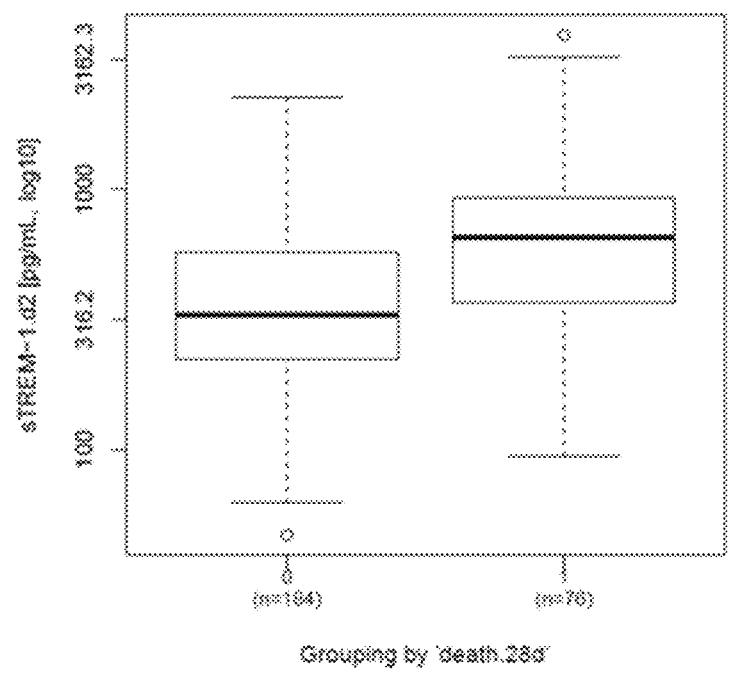
FIGS. 4A-4B are a set of boxplots of sTREM-1 at day 2 for 28-day mortality (FIG. 4A) and 90-day mortality (FIG. 4B). Chi$^2$ of Kruskal-Wallis test is 30.2 and 30.8, respectively (both p<0.0001).
Figure 4B:
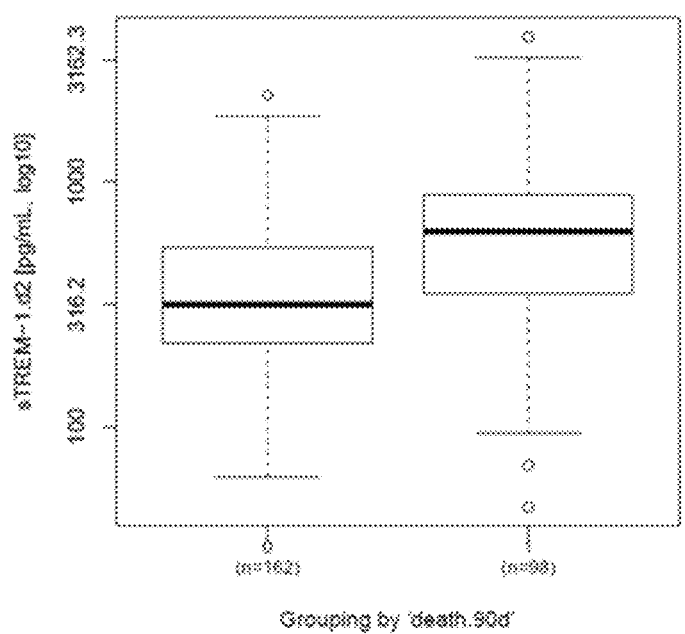
Figure 5A:
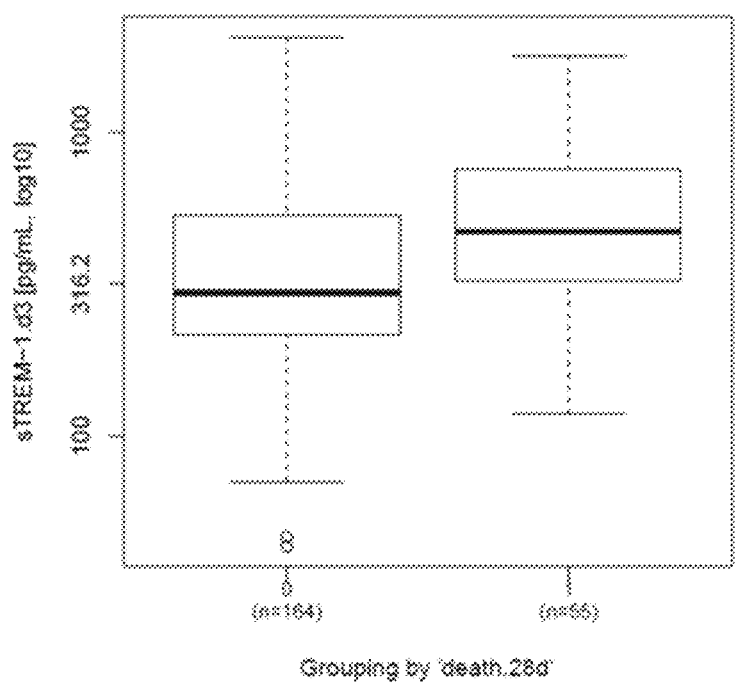
FIGS. 5A-5B are a set of boxplots of sTREM-1 at day 3 for 28-day mortality (FIG. 5A) and 90-day mortality (FIG. 5B). Chi$^2$ of Kruskal-Wallis test is 16.9 (p=0.0001) and 19.1 (p=0.0002).
Figure 5B:
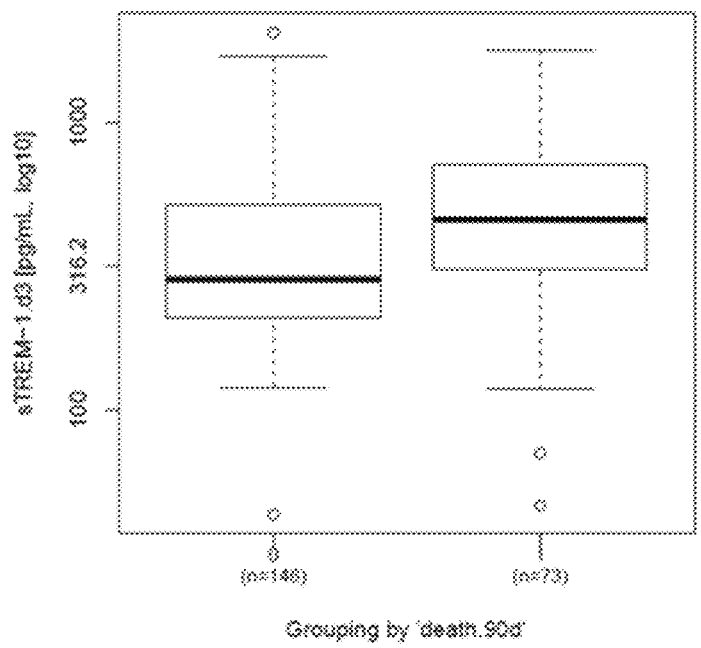
Figure 6A:
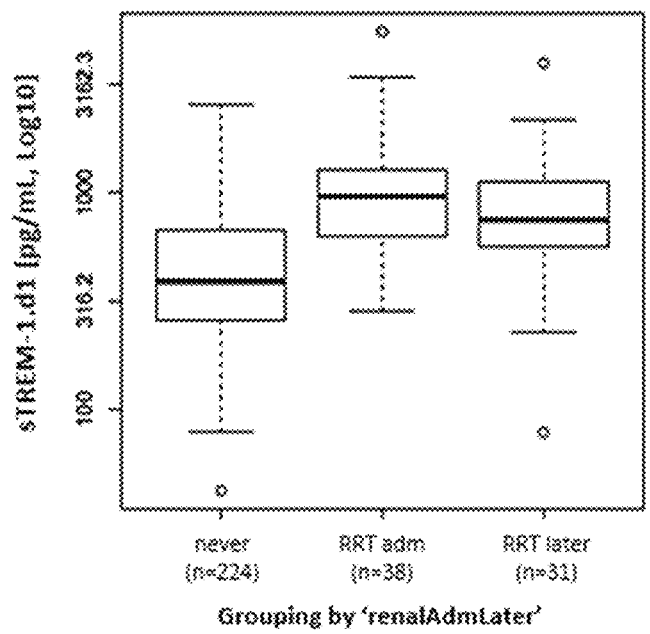
FIGS. 6A-6C are a set of boxplots of sTREM-1 at day 1 (FIG. 6A), day 2 (FIG. 6B), day 3 (FIG. 6C) for renal replacement therapy (RRT) at admission (RRT adm) and during ICU stay (RRT later). Chi$^2$ of Kruskal-Wallis test is 54.7 (p<0.0001) and 68.7 (p<0.0001) and 44 (p<0.0001) respectively.
Figure 6B:
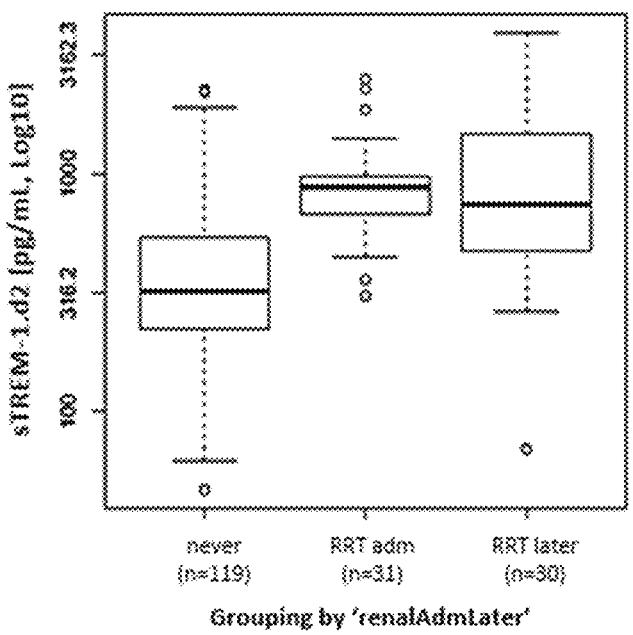
Figure 6C:
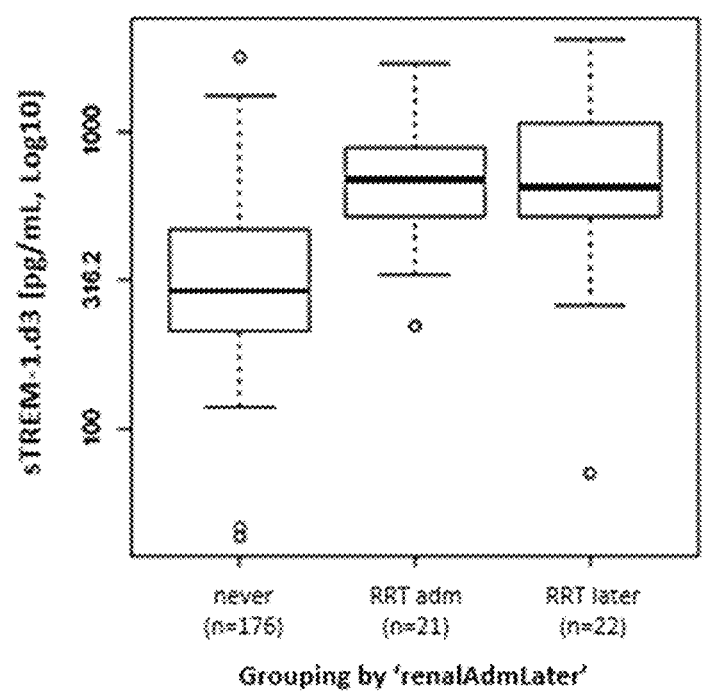

28-day and 90-day non-survivors showed sTREM-1 levels that were significantly elevated at baseline when compared to the sTREM-1 levels at baseline of 28-day and 90-day survivors (FIG. 3A-B). Interestingly, sTREM-1 values at day 1 were correlated with sTREM-1 values at day 2 and day 3 (Spearman rank correlation r=0.91 (CI: 0.88, 0.93; p<0.001; n=260) and Spearman rank correlation r=0.86 (CI: 0.81, 0.9); p<0.001; n=219)), and sTREM-1 values at day 2 were correlated with sTREM-1 values at day 3 (Spearman r=0.96 (CI: 0.95, 0.97; p<0.001, n=213)). sTREM-1 values at day 2 and day 3 were still found to be elevated in 28-day and 90-day non-survivors as compared to the sTREM-1 values at day 2 and day 3 in 28-day and 90-day survivors (FIG. 4A-B and FIG. 5A-B). sTREM-1 values at day 1, day 2 and day 3 were also associated with renal replacement therapy (RRT) at admission and during the length of stay (FIGS. 6A-C).

Among all parameters tested, sTREM-1 showed to be better correlated to SOFA score (Spearman rank correlation r=0.42, p<0.001; n=254).

All these results tend to demonstrate that the sTREM-1 level is associated with severity, renal replacement therapy and mortality. These results thus confirm that the sTREM-1 level may be used as a reliable biomarker for the identification of patients at risk of complicated outcome.

Example 3

Materials and Methods sTREM-1 Measurements: Validated EISA Method for the Quantitative Determination of sTREM-1 in Human $K_2$-EDTA Plasma The quantitative determination of sTREM-1 was carried out using the method described in Example 2.

Evaluation of sTREM-1 in a Phase Ha Clinical Trial with Nangibotide in Septic Shock Patients (NCT03158948)

This was a European prospective, observational, multinational study in 14 centers from 4 countries (France, Belgium, the Netherlands, and Spain). Patients were recruited from July 2017 to June 2018. The study was conducted in accordance with the principles set forth in the Declaration of Helsinki and subsequent amendments, the Guidelines of the International Conference on Harmonization on GCP, as well as the requirements of national drug and data protection laws and other applicable regulatory requirements.

This was a randomized, double-blind, two-stage, placebo-controlled study. As described in FIG. 7, the study was composed of 2 stages with a similar treatment regimen, in which 0.3, 1.0 or 3.0 mg/kg/h of nangibotide (corresponding to peptide LR12, having an amino acid sequence as set forth in SEQ ID NO: 9, also known as motrem) was tested versus placebo. All patients with a diagnosis of septic shock were considered for study participation. All potential study patients underwent standard care management procedures. Patients with evidence of septic shock according to the Sepsis-3 definition (Singer et al, JAMA 2016) were considered for inclusion (i.e., patients suffering from sepsis and having (i) persisting hypotension requiring vasopressors to maintain their mean arterial pressure ≥65 mm Hg and (ii) a serum lactate level >2 mmol/L (18 mg/dL) despite adequate volume resuscitation).

Exclusion criteria were previous episode of septic shock (vasopressor administration) within current hospital stay, underlying concurrent immunodepression, solid organ transplant requiring immunosuppressive therapy, known pregnancy, prolonged QT syndrome (QTc ≥440 ms), shock of any other cause, e.g., hypotension related to gastrointestinal bleeding, ongoing documented or suspected endocarditis, history of prosthetic heart valves, end-stage neurological disease, end-stage cirrhosis (Child Pugh Class C), acute Physiology And Chronic Health Evaluation (APACHE) II score ≥34, end stage chronic renal disease requiring chronic dialysis, home oxygen therapy on a regular basis for >6 h/day, severe obesity (body mass index [BMI]≥40), recent cardiopulmonary resuscitation (within current hospital stay), moribund patients and decision to limit full care taken before obtaining informed consent.

After screening for eligibility, patients were randomized to one of the treatment arms. Then, they received either a 5 mg/kg loading dose of nangibotide over 15 minutes followed by a continuous intravenous (i.v.) infusion of nangibotide or a matching placebo on top of standard of care. Treatment with study drug was initiated as early as possible, but no later than 24 hours after the onset of septic shock, defined by the start of vasopressor therapy. Patients were treated until 12 (±2) hours after the resolution of their septic shock (defined as vasopressor withdrawal) with a maximum treatment duration of 5 days (120 hours).

Stage 1 was performed to investigate ascending doses of nangibotide or placebo in a sequential design in cohorts of 4 patients (3:1 randomization). After completion of a cohort, safety and PK data were reviewed by an independent data safety monitoring board (DSMB) and the study could progress to the next cohort/stage. Stage 2 investigated 3 doses of nangibotide in a randomized, balanced, parallel-group design involving up to 3 doses of nangibotide and a placebo arm. Only dose arms of nangibotide considered to be safe and well tolerated during Stage 1 were administered in Stage 2.

PK Analytical Method for Phase IIa with Nangibotide

Blood nangibotide concentrations were determined by a validated LC-MS/MS method in accordance with European Medicines Agency (EMA) guidelines on bioanalytical method validation EMEA/CHMP/EWP/192217/2009, version EMA/275542/2014. The peptide was stabilized in the blood samples by treatment with a 10% trichloroacetic acid solution (1500 mg/mL, 4° C.) and centrifugation (3500 g, 10 min, 4° C.) to collect and freeze the supernatant before analysis. The lower limit of quantification (LLOQ) and upper limit of quantification (ULOQ) were 5 ng/mL and 1000 ng/mL respectively. Standard curve was linear over the range 5 ng/mL to 1000 ng/mL with a correlation coefficient greater than 0.995. Within-run and between-run precision and accuracy within +/−20% LLOQ and +/−15% (other levels up to ULOQ) were achieved during a 3-run validation for quality controls (QCs) for nangibotide.

Immunogenicity Evaluations

Anti-nangibotide antibodies in serum were evaluated at baseline, day 8 and day 28, by an indirect ELISA method validated according to methods described by Shankar et al. (J Pharm Biomed Anal. 2008 Dec. 15; 48(5):1267-81) and EMA guidance on immunogenicity assessment of biotechnology-derived therapeutic proteins (EMEA/CHMP/BMWP/14327/2006 issued on April 2008). Screening samples determined as positive were further assessed using the confirmatory assay where the cut point was established to have 0.1% of false positive samples (Shankar et al., J Pharm Biomed Anal. 2008 Dec. 15; 48(5):1267-81). Validation of the method showed no drug interference. The sensitivity of the assay was established to be 0.3125 pg/mL.

Statistical Analysis for the Phase IIa with Nangibotide

Adverse events (AEs) were coded using the MedDRA dictionary version 18.1. Treatment-emergent adverse events (TEAEs) were summarized and listed. Analysis was performed in 49 septic shock patients. The demographic and baseline characteristics were summarized in a descriptive fashion within each population: categorical variables were summarized by contingency tables (frequencies and percentages). sTREM-1 levels at day 1 were also described (mean, standard deviation, standard error, median, quartiles and range, minimum and maximum values). Mortality rates were reported by frequency and percentage. For continuous endpoints, i.e., the sequential organ failure assessment (SOFA), missing data were imputed using LOCF (Last Observation Carry-Forward). For time-to-event analyses, i.e., duration of invasive mechanical ventilation (IMV), duration of continuous renal replacement therapy (CRRT), survival, censored data techniques were utilized. In addition, a sensitivity analysis of time to event data (except survival) was performed using censoring at maximum limit for the corresponding observation period (i.e., either day 28 or day 90). The number of days alive and free from any vasopressor, IMV (Invasive Mechanical Ventilation) or CRRT (Continuous Renal Replacement Therapy) use was calculated as the total number of calendar days from the start of treatment (day 0) to day-28 visit when a subject is alive and does not require any vasopressor, IMV or CRRT treatment. The following comparisons were made: each nangibotide dose arm to placebo, all nangibotide doses combined versus placebo, and dose-response using an ordinal trend test. Exploratory composite endpoint: incidence (number and proportion) of patients alive at day 28 and free of vasopressor, free of IMV and free of CRRT were summarized by treatment and compared between treatments with a Fisher's exact test. For pharmacodynamic markers, log transformed data were represented as percentage change from baseline at day 5 or End of Infusion (EOI) if end of infusion was stopped before day 5. High sTREM-1 and low sTREM-1 patients were defined as patients who displayed a sTREM-1 blood concentration at entry to ICU (baseline, or day 0) below and above the median of the population, i.e., 433 pg/mL, respectively. "All nangibotide" refers to analyses obtained by pooling data from 0.3, 1 and 3 mg/kg/h nangibotide-treated groups.

Results

Patient Disposition and Baseline Characteristics 50 patients were randomized and 49 treated (one patient died before dosing). As shown in FIG. 8, twelve patients were randomized in each group and one additional patient was added to the 0.3 mg/kg/h group. All discontinuations were due to death. Thirty-six patients survived until day 90. All groups were well-balanced in terms of baseline characteristics (age, gender, race, weight, height, and BMI not shown). Average age was 64 (±13). On average, patients were under vasopressors for 15 hours (ranging from 3h to 24h) before starting the treatment with no significant differences between groups; 15 patients out of 49 were treated after receiving vasopressors between 3 and 12h (30.6%). The demographics and general baseline characteristics of the patients are depicted in Table 3 below.

TABLE 3

| Demographics and baseline characteristics of patients of the phase IIa with nangibotide | | | | | |
|---|---|---|---|---|---|
| | Placebo N = 12 | 0.3 mg/kg/h N = 13 | 1.0 mg/kg/h N = 12 | 3.0 mg/kg/h N = 12 | Total N = 49 |
| Primary type of infection at screening, number (%) | | | | | |
| Bacterial Gram-positive | 2 (16.7%) | 5 (38.5%) | 5 (41.7%) | 6 (50.0%) | 18 (36.7%) |
| Bacterial Gram-negative | 4 (33.3%) | 5 (38.5%) | 6 (50.0%) | 1 (8.3%) | 16 (32.7%) |
| Viral | — | — | — | 1 (8.3%) | 1 (2.0%) |
| Unknown[1] | 5 (41.7%) | 3 (23.1%) | — | 2 (16.7%) | 10 (20.4%) |
| Other[2] | 1 (8.3%) | — | 1 (8.3%) | 2 (16.7%) | 4 (8.2%) |
| Site of infection, number (%) | | | | | |
| Abdominal cavity | 5 (41.7%) | 8 (61.5%) | 4 (33.3%) | 4 (33.3%) | 21 (42.9%) |
| Lung | 6 (50.0%) | 5 (38.5%) | 6 (50.0%) | 8 (66.7%) | 25 (51.0%) |
| Urinary tract | 1 (8.3%) | — | 2 (16.7%) | — | 3 (6.1%) |
| Vasopressor duration, h, mean (SD) | 16.4 (6.3) | 16.9 (6.5) | 14.2 (4.8) | 13.4 (5.9) | 15.3 (5.9) |
| IMV, number (%) | 9 (75.0%) | 10 (76.9%) | 11 (91.7%) | 9 (75%) | 39 (79.6%) |
| CRRT, number (%) | — | 2 (15.4%) | 2 (16.7%) | 1 (8.3%) | 5 (10.2%) |
| APACHE II, mean (SD) | 22.3 (7.8) | 22.5 (4.9) | 25.1 (9.2) | 24.4 (5.6) | 23.6 6.9) |
| SOFA, mean (SD) | 10.1 (3.6) | 9.7 (3.0) | 10.9 (3.6) | 10.2 (2.6) | 10.2 (3.) |
| Lactate[3], mmol/L, mean (SD) | 3.9 (2.5) | 4.0 (2.4) | 4.3 (1.8) | 3.6 (1.4) | 4.0 (2.0) |
| NED[3], μg/kg/min, mean (SD) | 0.4 (0.4) | 0.4 (0.6) | 0.4 (0.3) | 0.8 (0.6) | 0.5 (0.5) |

[1]From unknown primary type of infections (10 patients), during the study 4 patients got negative cultures (3 in placebo and 1 in 3 mg/kg/h); 3 had mixed infections (1 in placebo, 1 in 0.3 mg/kg/h and 1 in 3 mg/kg/h); 1 had a gram-positive infection (placebo); and 2 had a gram-negative infection (2 in 0.3 mg/kg/h).
[2]Two correspond to 1 viral and gram-negative infection (placebo); 1 viral and gram-positive infection (1 mg/kg/h); 1 mixed gram-positive and gram-negative infection (3 mg/kg/h) and 1 misclassified patient having a gram-positive infection (3 mg/kg/h).
[3]Data from the Clinical Coordinating Center data base.
IMV: invasive mechanical ventilation;
CRRT: continuous renal replacement therapy;
NED: norepinephrine equivalent dose.

Safety

No adverse events (AEs) led to treatment withdrawal. The number of serious adverse events/adverse events (SAEs/AEs) and number of patients with SAEs/AEs was comparable between the nangibotide groups and the placebo group. Proportionally, the number of SAEs and patients with SAEs was higher in the placebo group. The number of AEs and patients with AEs with a severe intensity was comparable between treatment groups but proportionally higher in the placebo group. The numbers of AEs by system organ classes were comparable between treatment groups. AEs related to infections and cardiac disorders were proportionally higher in the nangibotide groups. The most frequent (>10%) AEs were atrial fibrillation, anemia, pleural effusion and thrombocytopenia. The incidence of atrial fibrillation and thrombocytopenia was proportionally higher in the nangibotide groups. Two suspected unexpected serious adverse reactions (SUSARs) without obvious explanation were reported and they were both in the nangibotide-treated group. There was no definitive explanation pointing towards relation to nangibotide treatment. As shown in Table 4 below, nangibotide was safe and well tolerated up to 3 mg/kg/h.

TABLE 4

| Treatment emergent adverse events (TEAEs) | | | | | |
|---|---|---|---|---|---|
| All TEAEs | Placebo N = 61 | 0.3 mg/kg/h N = 56 | 1.0 mg/kg/h N = 56 | 3.0 mg/kg/h N = 61 | Total N = 234 |
| All TEAEs with intensity severe | 17 (27.9%) | 12 (21.4%) | 13 (23.2%) | 8 (13.1%) | 50 (21.4%) |
| All TEAEs related to study drug (by investigator) | 4 (6.6%) | 0 (0.0%) | 4 (7.1%) | 0 (0.0%) | 8 (3.4%) |
| All serious TEAEs (including death) | 9 (14.8%) | 5 (8.9%) | 3 (5.4%) | 5 (8.2%) | 22 (9.4%) |
| All TEAEs leading to treatment withdrawal | 0 (0.0%) | 0 (0.0%) | 0 (0.0%) | 0 (0.0%) | 0 (0.0%) |

Pharmacokinetics

Figure 9A:
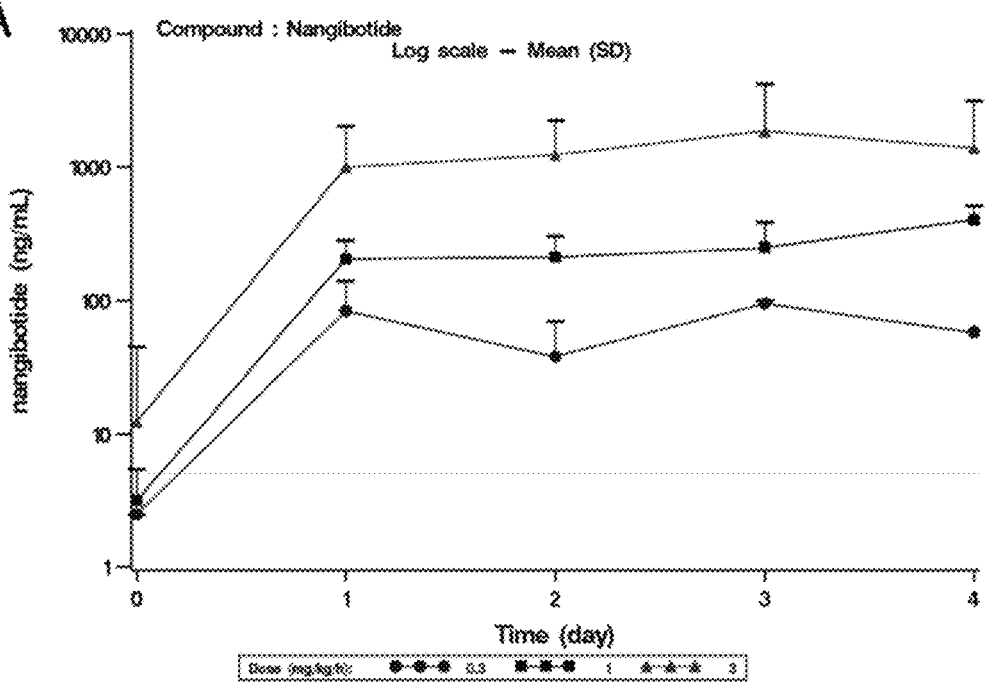
FIGS. 9A-9B are a set of graphs depicting the pharmacokinetics of nangibotide.
Figure 9B:
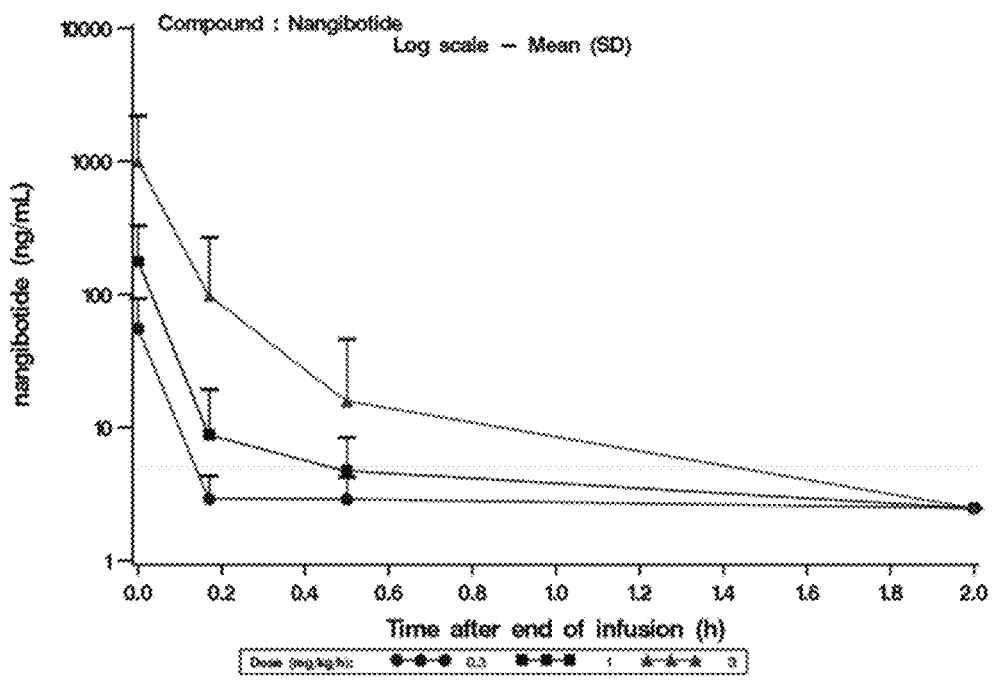

For all subjects in all groups, the pre-dose sample (blood sample withdrawn before the start of nangibotide infusion, i.e., baseline sample) did not contain quantifiable nangibotide. Mean nangibotide blood concentrations over time obtained from each group (i.e., patients who received 0.3 mg/kg/h, patients who received 1.0 mg/kg/h and who received 3.0 mg/kg/h) from the start of the intravenous infusion are shown in FIG. 9A. Nangibotide showed a linear behavior from the start to the end of intravenous infusion. Nangibotide blood concentration was found to be proportional with the dose. After the end of infusion, the product was quickly cleared (FIG. 9B) and showed a similar pattern of pharmacokinetics similar to that previously observed in healthy volunteers. No drug was detectable in blood 2 hours after the end of infusion, therefore no persistent pharmacological effect is foreseen after this period.

Mortality

There was a consistent trend in the proportion of death patients in favor of nangibotide-treated groups versus placebo. Indeed, all-cause mortality at day-28 was 14% (5/37) in pooled nangibotide groups and 25% (3/12) in placebo group (see Table 5 below).

TABLE 5

Mortality in the whole population

|  |  | Placebo (N = 12) | Nangibotide 0.3 mg/kg/h (N = 13) | Nangibotide 0.3 mg/kg/h (N = 12) | Nangibotide 0.3 mg/kg/h (N = 12) | Nangibotide pooled (N = 37) |
|---|---|---|---|---|---|---|
| All-cause mortality at 28 days | Number of death (%) | 3 (25%) | 2 (15%) | 1 (8.3%) | 3 (25%) | 6 (16%) |
| | p-value vs. Placebo | | 0.5483 | 0.2613 | 1.0000 | 0.5273 |
| All-cause mortality at 5 days | Number of death (%) | 2 (17%) | 1 (7.7%) | 1 (8.3%) | 2 (17%) | 4 (11%) |
| | p-value vs. Placebo | | 0.4919 | 0.5340 | 1.0000 | 0.6230 |
| All-cause mortality at 90 days | Number of death (%) | 3 (25%) | 4 (32%) | 2 (17%) | 4 (33%) | 10 (27%) |

In the subgroup with sTREM-1 levels at baseline above the median, i.e., above 433 pg/mL, all deaths were related to sepsis. In this group, all deaths occurred during the first week of the study. The day-5 mortality was calculated as 40% (2/5) and 20% (4/20) in placebo and nangibotide groups respectively (see Table 6 below).

TABLE 6

Mortality in the subgroup with sTREM-1 levels at baseline above the median (433pg/mL)

|  |  | Placebo (N = 5) | Nangibotide 0.3 mg/kg/h (N = 6) | Nangibotide 0.3 mg/kg/h (N = 6) | Nangibotide 0.3 mg/kg/h (N = 8) | Nangibotide pooled (N = 20) |
|---|---|---|---|---|---|---|
| Sepsis-related mortality at 28 days | Number of death (%) | 2 (40%) | 1 (17%) | 1 (17%) | 2 (25%) | 4 (20%) |
| | p-value vs Placebo | | 0.3819 | 0.3819 | 0.5748 | 0.3982 |
| Sepsis-related mortality at 5 days | Number of death (%) | 2 (40%) | 1 (17%) | 1 (17%) | 2 (25%) | 4 (20%) |
| | p-value vs Placebo | | 0.3819 | 0.3819 | 0.5748 | 0.3982 |
| Sepsis-related mortality at 90 days | Number of death (%) | 2 (40%) | 1 (17%) | 1 (17%) | 2 (25%) | 4 (20%) |
| | p-value vs Placebo | | 0.3819 | 0.3819 | 0.5748 | 0.3982 |

Organ Failure Parameters

Although no statistically significant differences were seen in clinical parameters between nangibotide-treated groups in comparison to the placebo group, a consistent numerical trend in favor of nangibotide was observed on SOFA score decrease during the first 5 days (additional decrease in treated groups versus placebo group). For example, as shown in Table 7 below, the difference in SOFA score in the "all nangibotide" group as compared to the "placebo" group was −0.70 (95% CI: −2.41, 1.01), ranging from −1.66 (95% CI: −3.73, 0.40) to 0.34 (95% CI: −1.76, 2.44) from 0.3 to 3 mg/kg/h doses.

TABLE 7

SOFA score evolution and difference between treatment arms and placebo in the whole population

| | | | Comparison vs. placebo | | | |
|---|---|---|---|---|---|---|
| Day | Treatment | LSMean (SE) | Estimated difference (SE) | 95% Confidence interval | p-value vs. placebo | p-value dose-response |
| Day 1 | Placebo | −0.92 (0.54) | | | | |
| | Nangibotide 0.3 mg/kg/h | −0.65 (0.52) | 0.26 (0.75) | (−1.25, 1.78) | 0.7273 | |
| | Nangibotide 1.0 mg/kg/h | −0.39 (0.54) | 0.53 (0.77) | (−1.01, 2.07) | 0.4926 | |
| | Nangibotide 3.0 mg/kg/h | −0.33 (0.54) | 0.59 (0.76) | (−0.95, 2.13) | 0.4454 | |
| | All nangibotide | −0.45 (0.31) | 0.46 (0.62) | (−0.79, 1.71) | 0.4628 | 0.4049 |
| Day 2 | Placebo | −1.33 (0.65) | | | | |
| | Nangibotide 0.3 mg/kg/h | −2.27 (0.63) | −0.94 (0.91) | (−2.76, 0.89) | 0.3079 | |
| | Nangibotide 1.0 mg/kg/h | −1.97 (0.65) | −0.64 (0.92) | (−2.50, 1.22) | 0.4941 | |
| | Nangibotide 3.0 mg/kg/h | −0.91 (0.65) | 0.42 (0.92) | (−1.44, 2.28) | 0.6497 | |
| | All nangibotide | −1.72 (0.37) | −0.38 (0.75) | (−1.90, 1.13) | 0.6118 | 0.5942 |
| Day 3 | Placebo | −1.25 (0.70) | | | | |
| | Nangibotide 0.3 mg/kg/h | −2.67 (0.68) | −1.42 (0.98) | (−3.40, 0.55) | 0.1534 | |
| | Nangibotide 1.0 mg/kg/h | −1.87 (0.71) | −0.62 (1.00) | (−2.63, 1.39) | 0.5363 | |
| | Nangibotide 3.0 mg/kg/h | −0.91 (0.70) | 0.34 (1.00) | (−1.67, 2.35) | 0.7337 | |
| | All nangibotide | −1.82 (0.40) | −0.57 (0.81) | (−2.20, 1.07) | 0.4872 | 0.5652 |
| Day 4 | Placebo | −1.41 (0.69) | | | | |
| | Nangibotide 0.3 mg/kg/h | −2.91 (0.67) | −1.50 (0.96) | (−3.44, 0.45) | 0.1280 | |
| | Nangibotide 1.0 mg/kg/h | −1.95 (0.70) | −0.53 (0.98) | (−2.51, 1.45) | 0.5912 | |
| | Nangibotide 3.0 mg/kg/h | −1.16 (0.69) | 0.26 (0.98) | (−1.72, 2.23) | 0.7931 | |
| | All nangibotide | −2.00 (0.40) | −0.59 (0.80) | (−2.20, 1.02) | 0.4640 | 0.5772 |
| Day 5 | Placebo | −1.25 (0.74) | | | | |
| | Nangibotide 0.3 mg/kg/h | −2.91 (0.71) | −1.66 (1.03) | (−3.73, 0.40) | 0.1115 | |
| | Nangibotide 1.0 mg/kg/h | −2.03 (0.74) | −0.78 (1.04) | (−2.88, 1.32) | 0.4594 | |
| | Nangibotide 3.0 mg/kg/h | −0.90 (0.74) | 0.34 (1.04) | (−1.76, 2.44) | 0.7441 | |
| | All nangibotide | −1.95 (0.42) | −0.70 (0.85) | (−2.41, 1.01) | 0.4133 | 0.5645 |

Interestingly, these differences were more important in the baseline high sTREM-1 subgroup (patients with a sTREM-1 level at baseline above the median, i.e., above 433 pg/mL). Indeed, as shown in Table 8 below, the difference in SOFA score in the "all nangibotide" group as compared to the "placebo" group was −1.5 (95% CI: −3.83, 0.84), ranging from −2.85 (95% CI: −5.68, −0.02; p=0.0487) to −0.16 (95% CI: −2.80, 2.48) from 0.3 to 3 mg/kg/h doses.

TABLE 8

SOFA score evolution and difference between treatment arms and placebo in patients with high sTREM-1 at baseline

| | | | Comparison vs. placebo | | | |
|---|---|---|---|---|---|---|
| Day | Treatment | LSMean (SE) | Estimated difference (SE) | 95% Confidence interval | p-value vs. placebo | p-value dose-response |
| Day 1 | Placebo | 0.02 (0.66) | | | | |
| | Nangibotide 0.3 mg/kg/h | 0.16 (0.60) | 0.14 (0.90) | (−1.73, 2.01) | 0.8793 | |
| | Nangibotide 1.0 mg/kg/h | −0.50 (0.59) | −0.52 (0.89) | (−2.37, 1.33) | 0.5655 | |
| | Nangibotide 3.0 mg/kg/h | −0.38 (0.51) | −0.40 (0.84) | (−2.14, 1.35) | 0.6415 | |
| | All nangibotide | −0.24 (0.33) | −0.26 (0.74) | (−1.80, 1.29) | 0.7306 | 0.4930 |
| Day 2 | Placebo | −0.37 (0.89) | | | | |
| | Nangibotide 0.3 mg/kg/h | −1.52 (0.80) | −1.14 (1.21) | (−3.66, 1.38) | 0.3566 | |
| | Nangibotide 1.0 mg/kg/h | −2.00 (0.80) | −1.63 (1.19) | (−4.12, 0.87) | 0.1887 | |
| | Nangibotide 3.0 mg/kg/h | −0.50 (0.69) | −0.13 (1.13) | (−2.49, 2.23) | 0.9094 | |
| | All nangibotide | −1.34 (0.44) | −0.97 (1.00) | (−3.05, 1.12) | 0.3450 | 0.8084 |
| Day 3 | Placebo | −0.09 (0.98) | | | | |
| | Nangibotide 0.3 mg/kg/h | −2.73 (0.89) | −2.64 (1.34) | (−5.43, 0.16) | 0.0631 | |
| | Nangibotide 1.0 mg/kg/h | −2.00 (0.89) | −1.90 (1.32) | (−4.67, 0.86) | 0.1655 | |
| | Nangibotide 3.0 mg/kg/h | −0.39 (0.77) | −0.30 (1.25) | (−2.91, 2.31) | 0.8128 | |
| | All nangibotide | −1.71 (0.49) | −1.61 (1.11) | (−3.92, 0.69) | 0.1601 | 0.9662 |

TABLE 8-continued

SOFA score evolution and difference between treatment arms and placebo in patients with high sTREM-1 at baseline

| Day | Treatment | LSMean (SE) | Comparison vs. placebo | | | p-value dose-response |
|---|---|---|---|---|---|---|
| | | | Estimated difference (SE) | 95% Confidence interval | p-value vs. placebo | |
| Day 4 | Placebo | −0.52 (1.03) | | | | |
| | Nangibotide 0.3 mg/kg/h | −3.22 (0.94) | −2.70 (1.41) | (−5.63, 0.24) | 0.0697 | |
| | Nangibotide 1.0 mg/kg/h | −1.83 (0.93) | −1.31 (1.39) | (−4.21, 1.59) | 0.3558 | |
| | Nangibotide 3.0 mg/kg/h | −0.51 (0.81) | 0.00 (1.31) | (−2.74, 2.75) | 0.9976 | |
| | All nangibotide | −1.85 (0.52) | −1.34 (1.16) | (−3.76, 1.09) | 0.2639 | 0.7397 |
| Day 5 | Placebo | −0.35 (1.00) | | | | |
| | Nangibotide 0.3 mg/kg/h | −3.20 (0.90) | −2.85 (1.36) | (−5.68, −0.02) | 0.0487 | |
| | Nangibotide 1.0 mg/kg/h | −1.83 (0.90) | −1.48 (1.34) | (−4.28, 1.31) | 0.2813 | |
| | Nangibotide 3.0 mg/kg/h | −0.51 (0.78) | −0.16 (1.27) | (−2.80, 2.48) | 0.9007 | |
| | All nangibotide | −1.85 (0.50) | −1.50 (1.12) | (−3.83, 0.84) | 0.1963 | 0.8270 |

Conversely, these differences were less important in the baseline low sTREM-1 subgroup (patients with a sTREM-1 level at baseline below the median, i.e., below 433 pg/mL). Indeed, as shown in Table 9 below, the difference in SOFA score in the "all nangibotide" group as compared to the "placebo" group at day 5 was −0.18 (95% CI: −2.95, 2.59), ranging from −0.71 (95% CI: −3.97, 2.54) to 0.12 (95% CI: −3.70, 3.94) from 0.3 to 3 mg/kg/h doses.

TABLE 9

SOFA score evolution and difference between treatment arms and placebo in patients with low sTREM-1 at baseline

| Day | Treatment | LSMean (SE) | Comparison vs. placebo | | | p-value dose-response |
|---|---|---|---|---|---|---|
| | | | Estimated difference (SE) | 95% Confidence interval | p-value vs. placebo | |
| Day 1 | Placebo | −1.68 (0.80) | | | | |
| | Nangibotide 0.3 mg/kg/h | −1.40 (0.80) | 0.29 (1.13) | (−2.09, 2.66) | 0.8036 | |
| | Nangibotide 1.0 mg/kg/h | −0.01 (0.88) | 1.67 (1.20) | (−0.85, 4.19) | 0.1814 | |
| | Nangibotide 3.0 mg/kg/h | −0.35 (1.06) | 1.33 (1.33) | (−1.45, 4.11) | 0.3285 | |
| | All nangibotide | −.059 (0.53) | 1.10 (0.96) | (−0.92, 3.11) | 0.2692 | 0.2117 |
| Day 2 | Placebo | −2.13 (0.92) | | | | |
| | Nangibotide 0.3 mg/kg/h | −2.99 (0.92) | −0.86 (1.30) | (−3.58, 1.87) | 0.5181 | |
| | Nangibotide 1.0 mg/kg/h | −1.62 (1.02) | 0.51 (1.38) | (−2.39, 3.40) | 0.7189 | |
| | Nangibotide 3.0 mg/kg/h | −1.87 (1.22) | 0.26 (1.53) | (−2.93, 3.46) | 0.8653 | |
| | All nangibotide | −2.16 (0.61) | −0.03 (1.11) | (−2.35, 2.29) | 0.9789 | 0.6582 |
| Day 3 | Placebo | −2.11 (1.02) | | | | |
| | Nangibotide 0.3 mg/kg/h | −2.68 (1.02) | −0.57 (1.44) | (−3.59, 2.45) | 0.6963 | |
| | Nangibotide 1.0 mg/kg/h | −1.51 (1.13) | 0.61 (1.53) | (−2.60, 3.81) | 0.6971 | |
| | Nangibotide 3.0 mg/kg/h | −2.10 (1.35) | 0.01 (1.69) | (−3.53, 3.55) | 0.9950 | |
| | All nangibotide | −2.10 (0.67) | 0.02 (1.23) | (−2.55, 2.58) | 0.9903 | 0.8219 |
| Day 4 | Placebo | −2.13 (0.94) | | | | |
| | Nangibotide 0.3 mg/kg/h | −2.70 (0.94) | −0.57 (1.32) | (−3.34, 2.20) | 0.6709 | |
| | Nangibotide 1.0 mg/kg/h | −1.79 (1.03) | 0.34 (1.41) | (−2.61, 3.29) | 0.8122 | |
| | Nangibotide 3.0 mg/kg/h | −2.62 (1.24) | −0.49 (1.55) | (−3.74, 2.76) | 0.7569 | |
| | All nangibotide | −2.37 (0.62) | −0.24 (1.13) | (−2.60, 2.12) | 0.8335 | 0.9109 |
| Day 5 | Placebo | −1.99 (1.10) | | | | |
| | Nangibotide 0.3 mg/kg/h | −2.71 (1.10) | −0.71 (1.56) | (−3.97, 2.54) | 0.6513 | |
| | Nangibotide 1.0 mg/kg/h | −1.93 (1.21) | 0.06 (1.65) | (−3.40, 3.53) | 0.9692 | |
| | Nangibotide 3.0 mg/kg/h | −1.87 (1.46) | 0.12 (−1.82) | (−3.70, 3.94) | 0.9480 | |
| | All nangibotide | −2.17 (0.73) | −0.18 (1.32) | (−2.95, 2.59) | 0.8954 | 0.8441 |

Figure 10A:
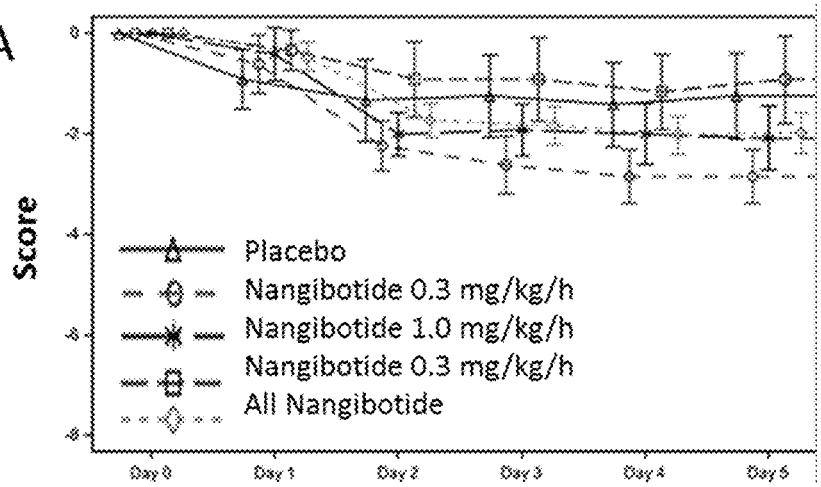
FIGS. 10A-10C are a set of graphs depicting the SOFA evolution over time change versus baseline (LOCF) in the whole population (FIG. 10A), patients with low sTREM-1 at baseline (below the median 433 pg/mL) (FIG. 10B), patients with high sTREM-1 at baseline (above the median 433 pg/mL) (FIG. 10C).
Figure 10B:
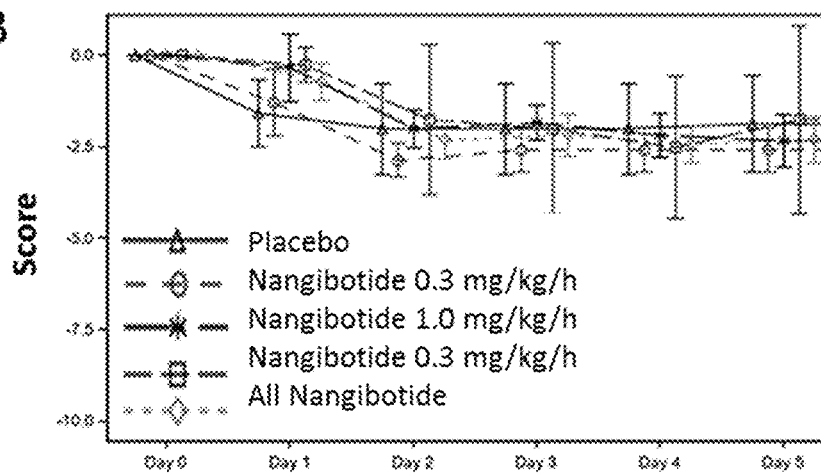
Figure 10C:
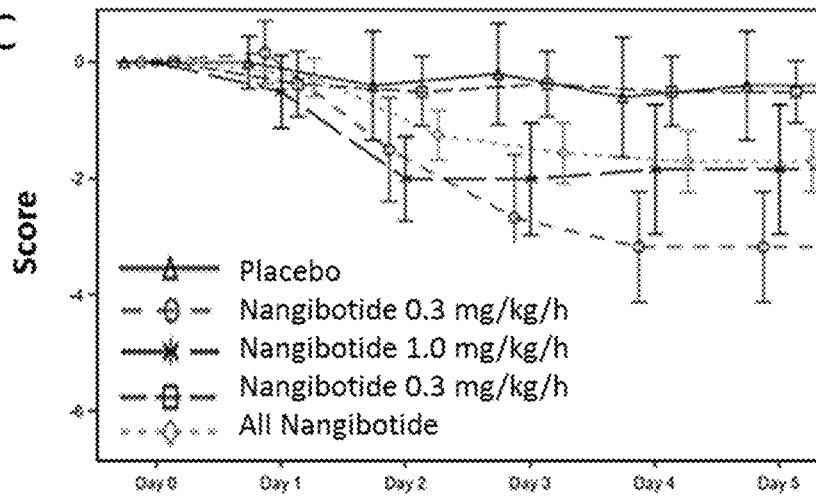

Unexpectedly, as shown on FIG. 10, an inverse dose response was observed, with a more pronounced difference in the low dose group 0.3 mg/kg/h (−2.85, p=0.0487) as compared to the high dose group 3 mg/kg/h (−0.16, p=0.9007).

These results show that the overall treatment-related decrease in SOFA score observed in the whole population was driven by a decrease in SOFA score in patients with the highest sTREM-1 baseline values (above the median, i.e., above 433 pg/mL), and no in-between group was observed in groups of patients with low baseline sTREM-1 values (below the median, i.e., below 433 pg/mL).

Similarly, although no statistically significant differences were seen in clinical parameters between nangibotide-treated groups in comparison to the placebo group, a consistent numerical trend in favor of nangibotide was observed on vasopressor use, on invasive mechanical ventilation (IMV) use and on renal replacement therapy (RRT) use.

In the baseline low sTREM-1 subgroup, the difference in the number of vasopressor free days alive in the "all nangibotide" group as compared to the "placebo" group was 0.64 (95% CI: −5.78, 7.07; p=0.8368), ranging from 2.29 (95% CI: −5.30, 9.87; p=0.5369) to 0.07 (95% CI: −8.83, 8.97; p=0.9868) from 0.3 to 3 mg/kg/h doses. In the baseline high sTREM-1 subgroup, the difference in the number of vasopressor free days alive in the "all nangibotide" group as compared to the "placebo" group was 2.94 (95% CI: −9.36, 15.25; p=0.6243), ranging from 4.07 (95% CI: −10.81, 18.94; p=0.5757) to −0.48 (95% CI: −14.48, 13.53; p=0.9444) from 0.3 to 3 mg/kg/h doses.

In the whole population, the difference in the number of IMV (invasive mechanical ventilation) free days alive in the "all nangibotide" group as compared to the "placebo" group was 1.33 (95% CI: −6.20, 8.89; p=0.7240), ranging from 2.32 (95% CI: −6.75, 11.40; p=0.6091) to −2.08 (95% CI: −11.34, 7.17; p=0.6524) from 0.3 to 3 mg/kg/h doses. In the baseline low sTREM-1 subgroup, the difference in the number of IMV (invasive mechanical ventilation) free days alive in the "all nangibotide" group as compared to the "placebo" group was −1.30 (95% CI: −9.92, 7.32; p=0.7568), ranging from 3 (95% CI: −7.18, 13.18; p=0.5455) to −6.32 (95% CI: −18.25, 5.61; p=0.2823) from 0.3 to 3 mg/kg/h doses. In the baseline high sTREM-1 subgroup, the difference in the number of IMV (invasive mechanical ventilation) free days alive in the "all nangibotide" group as compared to the "placebo" group was 5.63 (95% CI: −7.24, 18.51; p=0.3732), ranging from 2.63 (95% CI: −12.93, 18.20; p=0.7285) to 4.30 (95% CI: −10.35, 18.95; p=0.5483) from 0.3 to 3 mg/kg/h doses.

In the whole population, the difference in the number of CRRT (continuous renal replacement therapy) free days alive in the "all nangibotide" group as compared to the "placebo" group was 2.70 (95% CI: −4.46, 9.86; p=0.4516), ranging from 4.10 (95% CI: −4.53, 12.73; p=0.3435) to 1.50 (95% CI: −7.30, 10.30; p=0.7330) from 0.3 to 3 mg/kg/h doses. In the baseline low sTREM-1 subgroup, the difference in the number of CRRT (continuous renal replacement therapy) free days alive in the "all nangibotide" group as compared to the "placebo" group was 0.77 (95% CI: −4.72, 6.25; p=0.7738), ranging from 1.43 (95% CI: −5.04, 7.90; p=0.6502) to 0.89 (95% CI: −6.70, 8.48; p=0.8086) from 0.3 to 3 mg/kg/h doses. In the baseline high sTREM-1 subgroup, the difference in the number of CRRT (continuous renal replacement therapy) free days alive in the "all nangibotide" group as compared to the "placebo" group was 7.85 (95% CI: −5.22, 20.91; p=0.2254), ranging from 8.67 (95% CI: −7.13, 24.46; p=0.2666) to 7.37 (95% CI: −7.49, 22.24; p=0.3140) from 0.3 to 3 mg/kg/h doses.

Figure 11A:
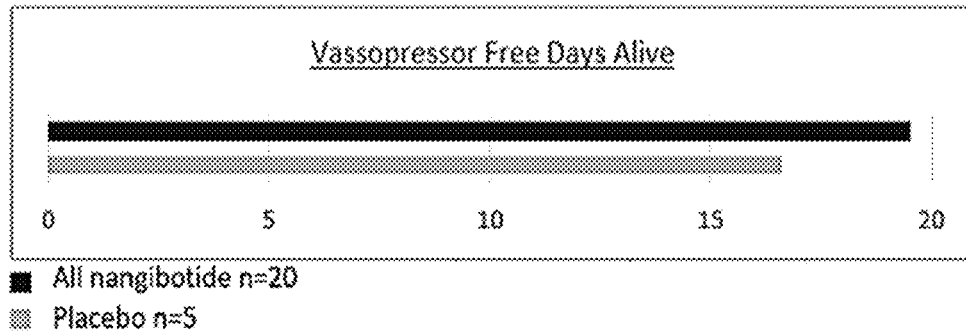
FIGS. 11A-11C are a set of graphs depicting organ support free days in patients with high levels of sTREM-1 at baseline (above the median 433 pg/mL): vasopressor free days alive (11A), invasive mechanical ventilation (IMV) free days alive (FIG. 11B), renal failure and continuous renal replacement therapy (CRRT) free days alive (FIG. 11C).
Figure 11B:
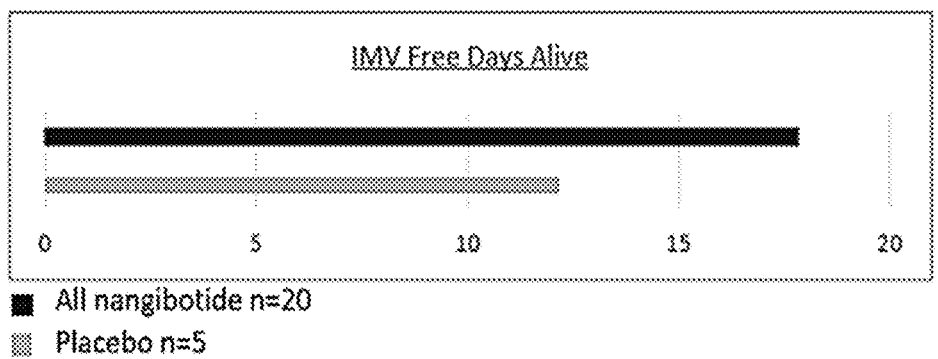
Figure 11C:
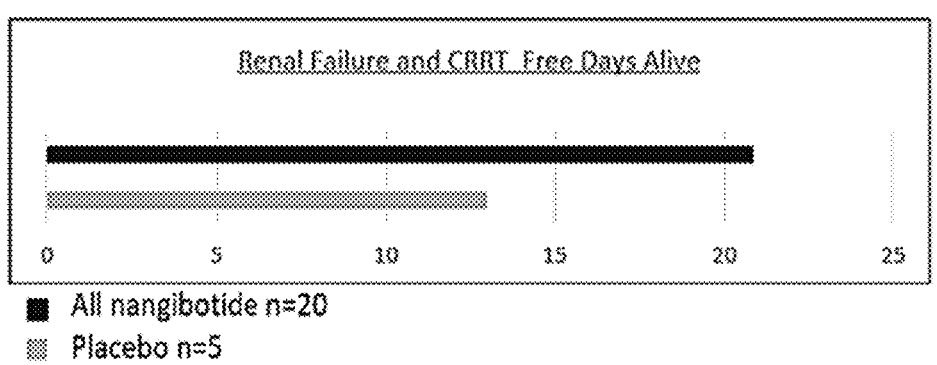

As shown in FIG. 11, these trends were magnified in patients with high levels of circulating sTREM-1 at baseline (above the median, i.e., above 433 pg/mL). In addition, in the "all nangibotide" group, the proportion of patients who were alive and free of any medical support at day 28 was 70% versus 40% in the "placebo" group.

Markers

Figure 12A:
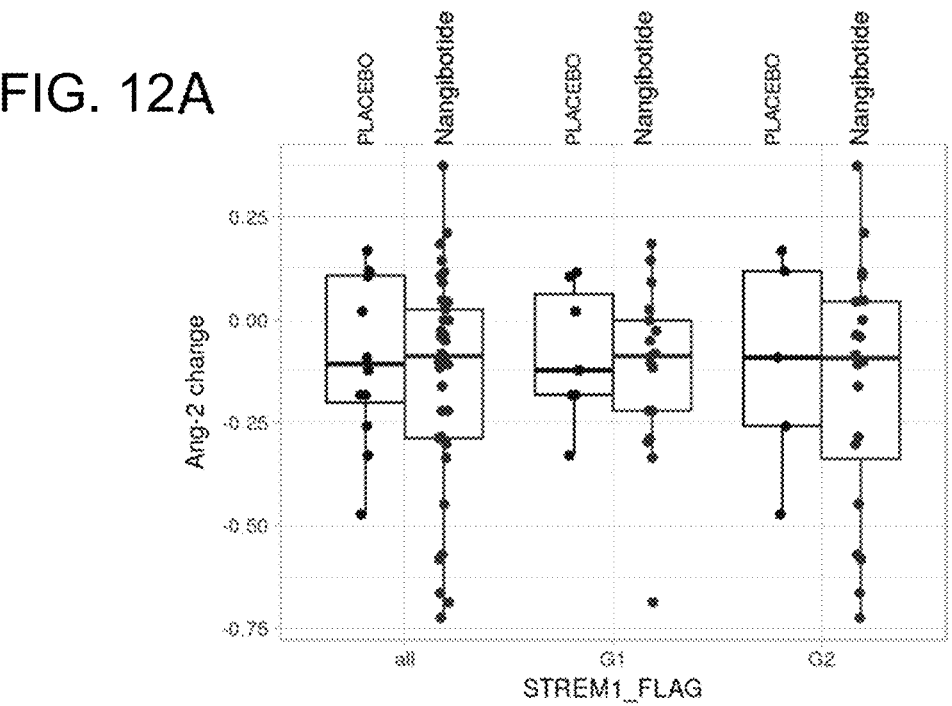
FIGS. 12A-12B are a set of graphs depicting Ang-2 concentration change from baseline at day 3 (FIG. 12A) and day 5 (FIG. 12B), in "all" (corresponding to the whole population), in the "G1" subgroup (corresponding to patients with low sTREM-1 at baseline, i.e., below the median 433 pg/mL), and "the G2" subgroup (corresponding to patients with high sTREM-1 at baseline, i.e., above the median 433 pg/mL).
Figure 12B:
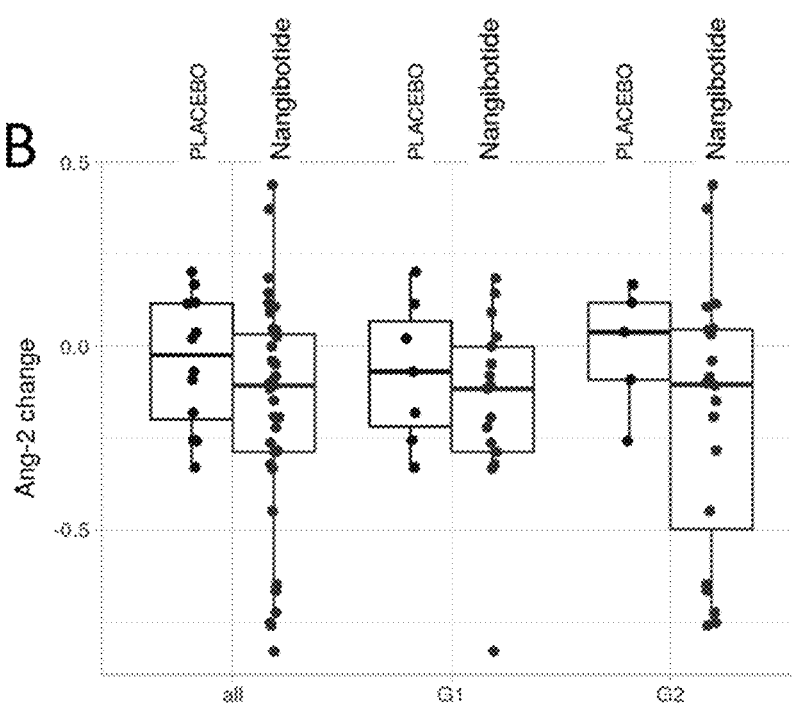
Figure 13A:
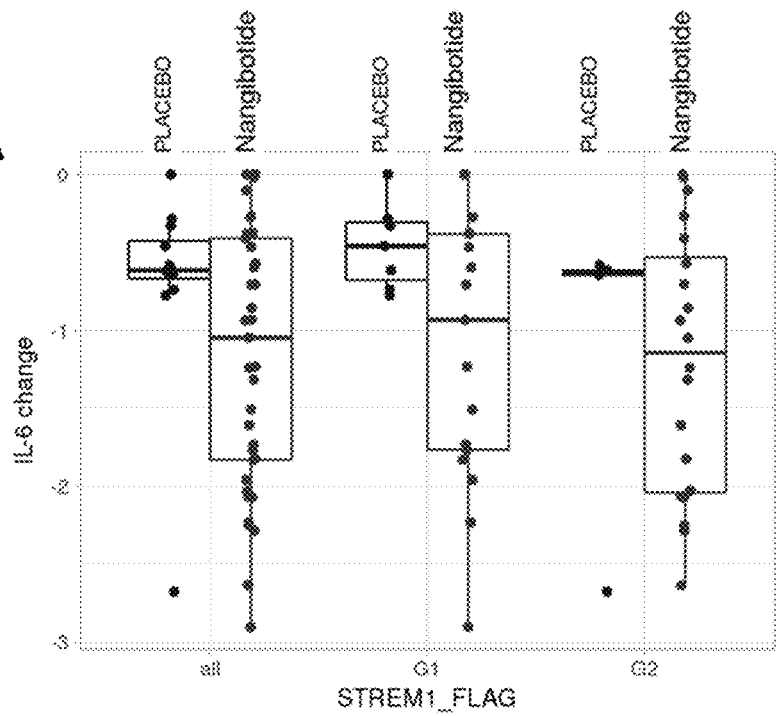
FIGS. 13A-13B are a set of graphs depicting IL-6 concentration change from baseline at Day 3 (FIG. 13A) and Day 5 (FIG. 13B), in "all" (corresponding to the whole population), in the "G1" subgroup (corresponding to patients with low sTREM-1 at baseline, i.e., below the median 433 pg/mL), and "the G2" subgroup (corresponding to patients with high sTREM-1 at baseline, i.e., above the median 433 pg/mL).
Figure 13B:
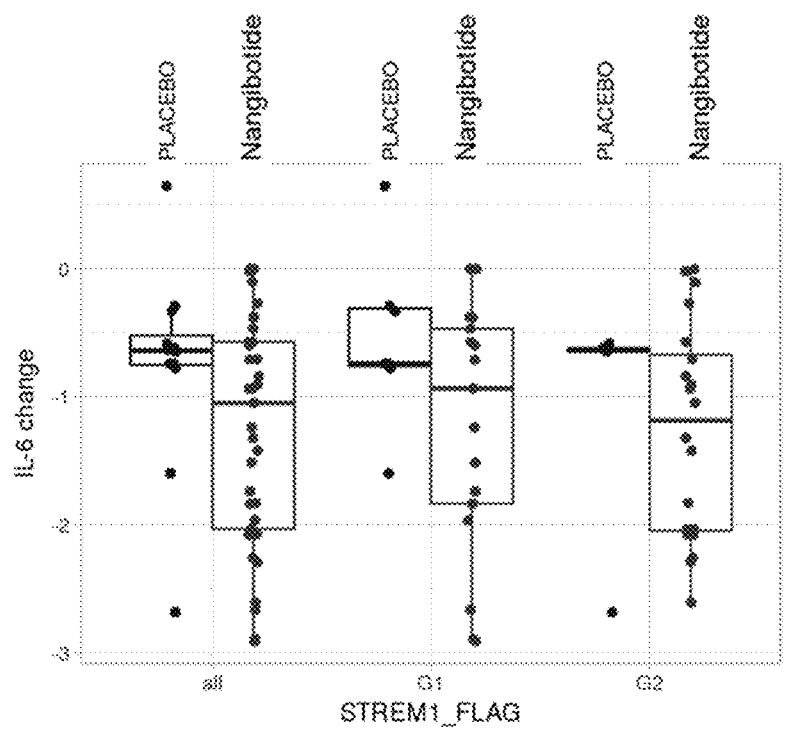

A trend towards a decrease during the treatment in circulating levels of endothelial injury markers (Ang-2, VCAM-1, VGEFR-1 and E-selectin), inflammatory markers (IL-8, IL-10, MCP-1, TNF-α and IL-10) and sTREM-1 was observed in nangibotide-treated patients, being more pronounced in patients with a high sTREM-1 level at baseline for Ang-2, IL-6 and sTREM-1. For example, when no apparent treatment effect was observed on the Ang-2 level in the whole population, a trend toward a more pronounced decrease was observed in the "G2" subgroup (i.e., patients with baseline sTREM-1 above the median 433 pg/mL) as compared to the whole population "all" and the "G1" subgroup (i.e., patients with baseline sTREM-1 below the median 433 pg/mL) (see FIG. 12). As shown on FIG. 13, the same trend was observed for the IL-6 level.

sTRFM-1 as an Efficacy Marker

Figure 14A:
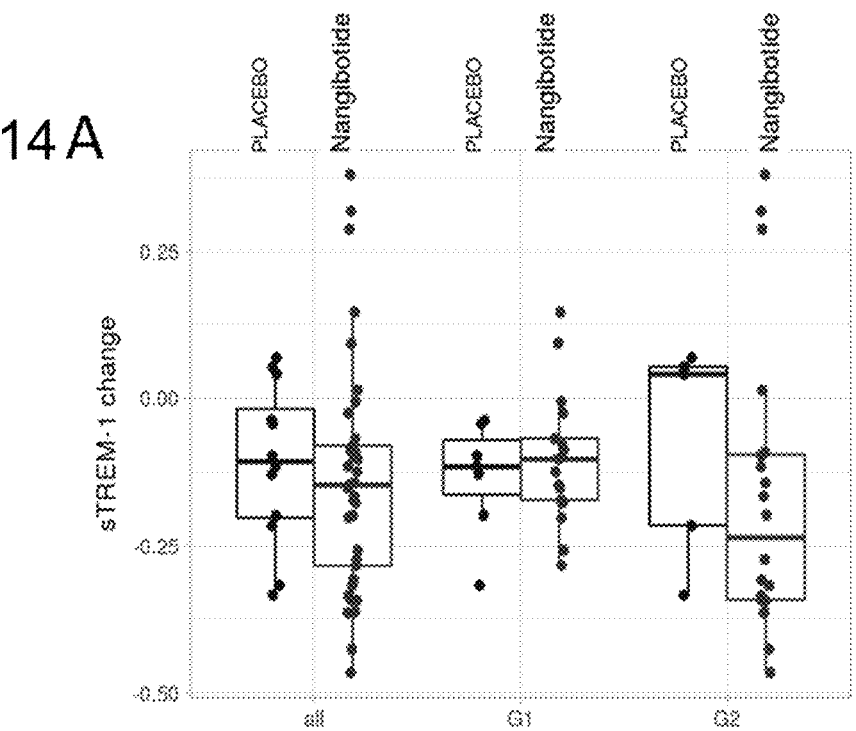
FIGS. 14A-14B are a set of graphs.
Figure 14B:
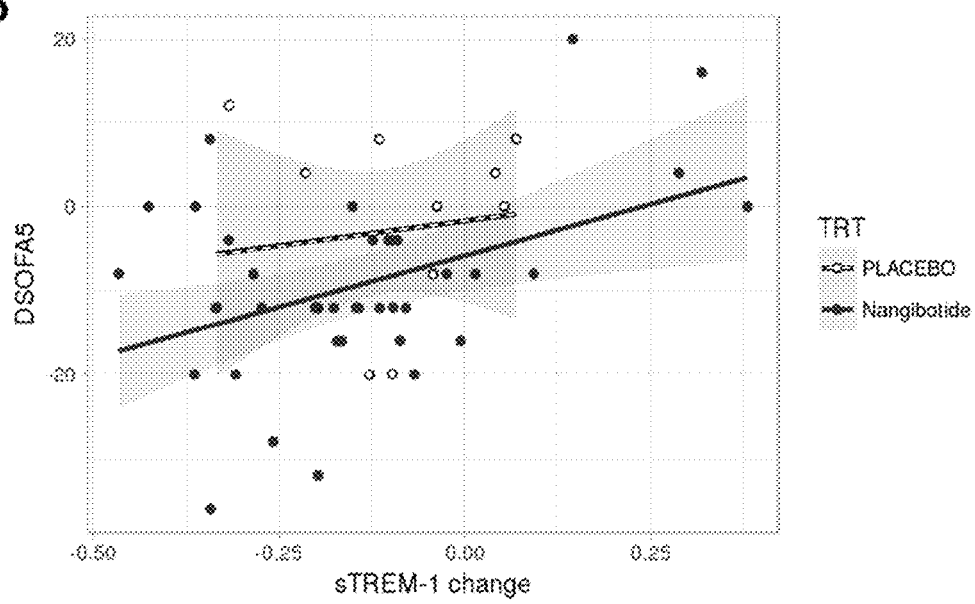

Besides its value as an inclusion biomarker, sTREM-1 was also evaluated as a marker for nangibotide efficacy in this phase IIa study. The impact of nangibotide treatment on the kinetics of sTREM-1 over time were evaluated. As shown in FIG. 14A, there were no apparent changes over time observed in the whole population, however a trend towards a decrease in sTREM-1 was observed in the subgroup of patients with high baseline sTREM-1 values. Interestingly, patients with the highest sTREM-1 change displayed the highest SOFA decrease at day 5/EOI (end of infusion) (FIG. 14B).

Conclusion

Nangibotide was shown to be safe and well-tolerated in septic shock patients. In this small exploratory study, a non-significant lower mortality was observed in the nangibotide group. Strikingly, clinical parameters and mortality showed a clearer tendency towards a beneficial effect of nangibotide in patients with a high circulating level of sTREM-1 at baseline.

Highly variable and controversial results have been published about the use of sTREM-1 as a prognostic marker in septic shock patients. This may be partly due to the lack of validated and reproducible quantitative assay. We have validated such a method, in accordance with the European Medicines Agency guideline: Committee for Medicinal Products for Human Use (CHMP) (2011), Guideline on bioanalytical method validation EMEA/CHMP/EWP/192217/2009 Rev. 1 Corr. 2. The validated method is described in the hereinabove (see Materials and Methods), and was used for the retrospective measurements of sTREM-1 levels in the two independent clinical cohorts (AdrenOSS cohort and the cohort from the phase IIa clinical study with nangibotide).

Interestingly, as shown in Table 10 below, comparable data were obtained in these two independent European cohorts of 293 and 49 patients.

TABLE 10 sTREM-1 general descriptive in the AdrenOSS cohort and in the phase IIa clinical trial with nangibotide

| AdrenOSS | Samples | Median | Q1 | Q2 | Q3 | Q4 |
| --- | --- | --- | --- | --- | --- | --- |
| STREM-1 (pg/mL) [min, max] | June 2015 to May 2016 N = 293 patients | 497 | 226 [42, 299] | 372 [300, 497] | 635 [500, 8091] | 1110 [810, 5540] |
| All-Cause Mortality at 28 days (%) | | | 12 | 30 | 37 | 49 |
| Phase IIa nangibotide | Samples | Median | Q1 | Q2 | Q3 | Q4 |
| STREM-1 (pg/mL) [min, max] | July 2017 to March 2018 N = 49 patients | 433 | 250 [154, 302] | 354 [304, 412] | 552 [433, 693] | 990 [719, 1960] |
| All-Cause Mortality at 28 days (%) | | | 8 | 17 | 8 | 42 | sTREM-1 values at baseline were associated with 28-day mortality: 12% and 8% mortality rates were observed in sTREM-1 quartile Q1 subgroup, and 49% and 42% mortality rates were observed in sTREM-1 quartile Q4 subgroup. The median values were 497 pg/mL in the AdrenOSS cohort, and 433 pg/mL in the phase IIa with nangibotide, with min/max values (in pg/mL) at 42/5540 and 154/1960 pg/mL, respectively, which suggest a similar distribution between the two cohorts.

These results confirm the need for a validated method for the collection of reliable data between different cohorts.

They also confirm that, with such a method, a reference value from a reference population can be used for the derivation of a predetermined sTREM-1 value, which can be used in further studies.

Overall, this study aimed to evaluate the value of sTREM-1 level assessment for patient selection before nangibotide administration. Indeed, discordant data from the literature showed that high sTREM-1 values at baseline were associated with complicated outcome (Charles et al., BMC Infect Dis. 2016 Oct. 12; 16(1):559) despite previous clinical data where low sTREM-1 values at baseline were associated with complicated outcome (Gibot et al., Crit Care Med. 2005 April; 33(4):792-6.). It therefore remained unclear whether sTREM-1 values were associated with severity and clinical outcome. The mechanism of sTREM-1 release was also unclear.

In this study, we demonstrated for the first time that sTREM-1 release depends on TREM-1 activation. Therefore, sTREM-1 may be used as a reliable surrogate of TREM-1 pathway activation. It may thus allow to identify the patients who will most likely benefit from an anti-TREM-1 therapeutic approach such as nangibotide (corresponding to peptide LR12, having an amino acid sequence as set forth in SEQ ID NO: 9).

We also have demonstrated, with a validated method in accordance with the guidelines, that high sTREM-1 values were correlated with severity and mortality in septic shock patients, using two independent cohorts. Therefore, we confirmed that sTREM-1 is a reliable biomarker of severity, and may allow the identification of patients at risk of complicated outcome. Indeed, baseline sTREM-1 blood concentration, i.e., within 24 hours following the diagnostic of septic shock, was found to be correlated with severity.

We also performed a subgroup analysis in the phase IIa clinical trial assessing the safety and tolerability of nangibotide in septic shock patients, in which the efficacy of nangibotide was compared between patients with baseline sTREM-1 values below a predetermined sTREM-1 value, herein defined as the median, and patients with baseline sTREM-1 values above this predetermined sTREM-1 value. We confirmed that nangibotide efficacy was more pronounced in patients with baseline sTREM-1 above the predetermined sTREM-1 value, i.e., above the median (above 433 pg/mL). This was observed on pharmacodynamic parameters (endothelium and inflammatory biomarkers), on the use of medical support (IMV, CRRT, vasopressors), and on the SOFA score.

The lower pharmacological activity of nangibotide in patients with a baseline sTREM-1 level below the predetermined sTREM-1 value cannot be explained by toxicity and side effects, since nangibotide was well-tolerated at all doses tested, and no adverse events related to nangibotide treatment were observed at the highest dose. No anti-nangibotide antibodies were found in the serum of patients, which also indicate that this apparent lower pharmacological activity in these patients cannot be related to the presence of anti-nangibotide neutralizing antibodies that would have been able to inhibit nangibotide. The blood concentrations of nangibotide were proportional with the dose, and within the same range previously observed in healthy volunteers, meaning that there was no abnormal pharmacokinetic profile of nangibotide in patients that may have also explained the in-between groups differences. The product was quickly cleared after the end of infusion, which also means that no persistent pharmacological activity may explain these differences.

Overall, these results confirm that sTREM-1 is a reliable companion diagnostic marker for patient inclusion and for TREM-1 inhibitor (e.g., nangibotide) administration.

NUMBERED EMBODIMENTS

Embodiments disclosed herein include embodiments A1 to A15, as follows:

Embodiment A1. An in vitro method for identifying a human subject suffering from an inflammatory disorder susceptible to respond to a therapy, preferably to a TREM-1 inhibitor, said method comprising:
  a) measuring the level of soluble Triggering Receptors Expressed on Myeloid cells-1 (sTREM-1) in a biological sample from the human subject;
  b) comparing the level of sTREM-1 measured at step a) to a predetermined sTREM-1 value;
  c) identifying a human subject suffering from an inflammatory disorder with a level of sTREM-1 measured at step a) higher than the predetermined sTREM-1 value of step b) as susceptible to respond to a therapy, preferably to a TREM-1 inhibitor.

Embodiment A2. The in vitro method according to Embodiment A1, wherein the predetermined sTREM-1 value of step b) is obtained from a reference population.

Embodiment A3. The in vitro method according to Embodiment A2, wherein the reference population is a population of human patients suffering from an inflammatory disorder, preferably systemic inflammatory response syndrome (SIRS), sepsis or septic shock.

Embodiment A4. The in vitro method according to Embodiment A2 Embodiment A3, wherein the predetermined sTREM-1 value of step b) is the sTREM-1 median in the reference population or the sTREM-1 third quartile in the reference population.

Embodiment A5. The in vitro method according to any one of Embodiments A1 to A4, wherein the level of sTREM-1 measured at step a) is a level measured before the beginning of the therapy, preferably before the administration of a TREM-1 inhibitor.

Embodiment A6. The in vitro method according to any one of Embodiments A1 to A5, wherein the level of sTREM-1 measured at step a) is measured within the first 24 hours following the diagnosis or the hospitalization of the human subject for an inflammatory disorder.

Embodiment A7. The in vitro method according to any one of Embodiments A1 to A6, wherein the biological sample is a blood sample, a serum sample or a plasma sample.

Embodiment A8. The in vitro method according to any one of Embodiments A1 to A7, wherein the level of sTREM-1 measured at step a) is a protein level, preferably measured by ELISA, electrochemiluminescence immunoassay (ECLIA) or enzyme-linked fluorescent assay (ELFA).

Embodiment A9. The in vitro method according to any one of Embodiments A1 to A8, wherein the therapy is a TREM-1 inhibitor selected from the group consisting of peptides inhibiting the function, activity or expression of TREM-1; antibodies directed to TREM-1 and/or sTREM-1, or TREM-1 and/or sTREM-1 ligand; small molecules inhibiting the function, activity or expression of TREM-1; siRNAs directed to TREM-1; shRNAs directed to TREM-1; antisense oligonucleotide directed to TREM-1; ribozymes directed to TREM-1 and aptamers directed to TREM-1.

Embodiment A10. The in vitro method according to Embodiment A9, wherein the TREM-1 inhibitor is a peptide inhibiting the function, activity or expression of TREM-1 by targeting TREM-1 ligand, preferably a peptide having an amino acid sequence selected from the group consisting of SEQ ID NO: 8, SEQ ID NO: 9, SEQ ID NO: 10, SEQ ID NO: 11, and SEQ ID NO: 12.

Embodiment A11. The in vitro method according to Embodiment A9 or Embodiment A10, wherein the TREM-1 inhibitor is a peptide having an amino acid sequence as set forth in SEQ ID NO: 9.

Embodiment A12. The in vitro method according to any one of Embodiments A1 to A11, wherein the inflammatory disorder is selected from the group comprising systemic inflammatory response syndrome (SIRS), sepsis and septic shock, preferably the inflammatory disorder is septic shock.

Embodiment A13. The in vitro method according to any one of Embodiments A1 to A12, wherein the human subject is suffering from an organ dysfunction defined as an acute change in his/her sequential organ failure assessment (SOFA) score of at least 2 points.

Embodiment A14. The in vitro method according to Embodiments A12 or A13, wherein a human subject suffering from SIRS, sepsis or septic shock susceptible to respond to a therapy, preferably to a TREM-1 inhibitor, is a human subject susceptible to have his/her sequential organ failure assessment (SOFA) score decrease following the administration of the therapy, preferably following the administration of a TREM-1 inhibitor.

Embodiment A15. The in vitro method according to Embodiments A12 or A13, wherein a human subject suffering from septic shock susceptible to respond to a therapy, preferably to a TREM-1 inhibitor, is a human subject suffering from septic shock susceptible to reverse a hypotensive shock within or after the administration period of the therapy, preferably of a TREM-1 inhibitor, wherein a hypotensive shock reversal is defined as the absence of any vasopressor therapy during 24 hours.

The invention claimed is:

1. A method of treating septic shock in a human subject in need thereof, the method comprising:
administering to the subject who has a blood, serum, or plasma concentration above 433 pg/mL of soluble Triggering Receptors Expressed on Myeloid cells-1 (sTREM-1) an effective amount of nangibotide thereby to treat the septic shock.

2. The method of claim 1, wherein the nangibotide is administered to the subject at a dose range of about 0.1 mg per kg body weight per hour (mg/kg/hr) to about 2.5 mg/kg/hr by continuous intravenous infusion.

3. The method of claim 2, wherein the nangibotide is administered to the subject at a dose range of about 0.3 mg/kg/hr to about 1 mg/kg/hr.

4. The method of claim 3, wherein the nangibotide is administered to the subject at a dose of about 1 mg/kg/hr.

5. The method of claim 1, wherein the nangibotide is administered by continuous infusion for at least 24 hours.

6. The method of claim 1, wherein the concentration of sTREM-1 is in the range of from about 500 pg/mL to about 1,500 pg/mL.

7. The method of claim 1, wherein the concentration of sTREM-1 is measured by an enzyme-linked immunosorbent assay (ELISA).

8. The method of claim 1, wherein the concentration of sTREM-1 is measured by an electrochemiluminescence immunoassay (ECLIA).

9. The method of claim 1, wherein administration of nangibotide results in a decrease in sequential organ failure assessment (SOFA) score.

10. The method of claim 5, wherein the infusion is continuous intravenous infusion.

11. The method of claim 10, wherein the nangibotide is administered to the subject at a dose of about 0.3 mg/kg/hr to about 1 mg/kg/hr.

12. The method of claim 11, wherein the nangibotide is administered to the subject for up to 5 days.

13. The method of claim 12, wherein the concentration of sTREM-1 is in the range of from about 500 pg/mL to about 1,500 pg/mL.

14. The method of claim 10, wherein the nangibotide is administered to the subject at a dose of about 1 mg/kg/hr.

15. The method of claim 14, wherein the nangibotide is administered to the subject for up to 5 days.

16. The method of claim 15, wherein the concentration of sTREM-1 is in the range of from about 500 pg/mL to about 1,500 pg/mL.

* * * * *

UNITED STATES PATENT AND TRADEMARK OFFICE
CERTIFICATE OF CORRECTION

| | | |
|---|---|---|
| PATENT NO. | : 12,364,733 B1 | Page 1 of 1 |
| APPLICATION NO. | : 18/766845 | |
| DATED | : July 9, 2024 | |
| INVENTOR(S) | : Derive et al. | |

It is certified that error appears in the above-identified patent and that said Letters Patent is hereby corrected as shown below:

In the Claims

At Column 86, Line 65-66 replace "The method of claim 1, wherein the concentration of sTREM-1is" with --The method of claim 1, wherein the concentration of sTREM-1 is--.

At Column 87, Lines 1-2 replace "The method of claim 1, wherein the concentration of sTREM-1is" with --The method of claim 1, wherein the concentration of sTREM-1 is--.

At Column 87, Lines 4-5 replace "The method of claim 1, wherein the concentration of sTREM-1is" with --The method of claim 1, wherein the concentration of sTREM-1 is--.

Signed and Sealed this
Second Day of September, 2025

Coke Morgan Stewart
*Acting Director of the United States Patent and Trademark Office*